United States Patent
Paulson et al.

(10) Patent No.: US 8,507,243 B2
(45) Date of Patent: *Aug. 13, 2013

(54) ALPHA-AMYLASE BLENDS AND METHODS FOR USING SAID BLENDS

(75) Inventors: Bradley A. Paulson, Brodhead, WI (US); Vivek Sharma, North Liberty, IA (US); Jayarama K. Shetty, Pleasanton, CA (US)

(73) Assignee: Danisco US Inc., Palo Alto, CA (US)

( * ) Notice: Subject to any disclaimer, the term of this patent is extended or adjusted under 35 U.S.C. 154(b) by 73 days.

This patent is subject to a terminal disclaimer.

(21) Appl. No.: 13/119,953

(22) PCT Filed: Sep. 11, 2009

(86) PCT No.: PCT/US2009/056613
§ 371 (c)(1),
(2), (4) Date: Jun. 16, 2011

(87) PCT Pub. No.: WO2010/036515
PCT Pub. Date: Apr. 1, 2010

(65) Prior Publication Data
US 2011/0244526 A1 Oct. 6, 2011

Related U.S. Application Data

(60) Provisional application No. 61/100,092, filed on Sep. 25, 2008, provisional application No. 61/238,891, filed on Sep. 1, 2009.

(51) Int. Cl.
*C12N 9/26* (2006.01)
(52) U.S. Cl.
USPC .......................................................... 435/201
(58) Field of Classification Search
USPC .......................................................... 435/201
See application file for complete search history.

(56) References Cited

U.S. PATENT DOCUMENTS

| | | | |
|---|---|---|---|
| 3,912,590 A | 10/1975 | Slott et al. | |
| 4,106,991 A | 8/1978 | Markussen et al. | |
| 4,316,956 A | 2/1982 | Lutzen | |
| 4,335,208 A | 6/1982 | Norman | |
| 4,435,307 A | 3/1984 | Barbesgaard et al. | |
| 4,536,182 A | 8/1985 | Tatin | |
| 4,643,736 A | 2/1987 | Cholley | |
| 4,661,452 A | 4/1987 | Markussen et al. | |
| 4,683,202 A | 7/1987 | Mullis | |
| 4,689,297 A | 8/1987 | Good et al. | |
| 4,753,748 A | 6/1988 | Laitem et al. | |
| 4,760,025 A | 7/1988 | Estell et al. | |
| 4,933,279 A | 6/1990 | Carroll et al. | |
| 5,112,518 A | 5/1992 | Klugkist | |
| 5,141,664 A | 8/1992 | Corring et al. | |
| 5,231,017 A | 7/1993 | Lantero et al. | |
| 5,240,632 A | 8/1993 | Brumbaugh | |
| 5,281,526 A | 1/1994 | Good et al. | |
| 5,324,649 A | 6/1994 | Arnold et al. | |
| 5,457,046 A | 10/1995 | Woldike et al. | |
| 5,648,263 A | 7/1997 | Schulein et al. | |
| 5,686,593 A | 11/1997 | Woldike et al. | |
| 5,691,178 A | 11/1997 | Schulein et al. | |
| 5,763,254 A | 6/1998 | Woldike et al. | |
| 5,776,757 A | 7/1998 | Schulein et al. | |
| 5,814,501 A | 9/1998 | Becker et al. | |
| 5,879,920 A | 3/1999 | Dale et al. | |
| 5,958,739 A | 9/1999 | Mitchinson et al. | |
| 6,017,867 A | 1/2000 | Baillely et al. | |
| 6,077,316 A | 6/2000 | Lund et al. | |
| 6,093,562 A | 7/2000 | Bisgard-Frantzen et al. | |
| 6,143,708 A | 11/2000 | Svendsen et al. | |
| 6,207,149 B1 | 3/2001 | Fuglsang et al. | |
| 6,287,841 B1 | 9/2001 | Mulleners et al. | |
| 6,297,038 B1 | 10/2001 | Bisgard-Frantzen et al. | |
| 6,403,355 B1 | 6/2002 | Hagihara et al. | |
| 6,423,524 B1 | 7/2002 | Hagen et al. | |
| 6,475,762 B1 | 11/2002 | Stafford et al. | |
| 6,528,298 B1 | 3/2003 | Svendsen et al. | |
| 6,562,612 B2 | 5/2003 | Jones et al. | |
| 6,867,031 B2 | 3/2005 | Bisgård-Frantzen et al. | |
| 7,498,158 B2 | 3/2009 | Svendsen et al. | |
| 7,541,026 B2 | 6/2009 | Power et al. | |
| 7,713,723 B1 | 5/2010 | Thisted et al. | |
| 8,153,412 B2 | 4/2012 | Shaw et al. | |
| 2002/0155574 A1 | 10/2002 | Thisted et al. | |
| 2005/0250663 A1 | 11/2005 | Thisted et al. | |
| 2006/0014265 A1 | 1/2006 | Ferrari et al. | |
| 2007/0212768 A1 | 9/2007 | Bessler et al. | |

(Continued)

FOREIGN PATENT DOCUMENTS

| CA | 2006687 | 6/1990 |
|---|---|---|
| DE | 3833047 | 4/1990 |

(Continued)

OTHER PUBLICATIONS

U.S. Appl. No. 10/576,331, filed Jul. 18, 2007, Jones et al.
U.S. Appl. No. 10/630,203, filed Nov. 10, 2005, Thisted et al.
U.S. Appl. No. 11/581,102, filed Nov. 27, 2008, Shaw et al.
U.S. Appl. No. 11/583,334, filed Oct. 19, 2006, Aehle et al.
U.S. Appl. No. 11/714,487, filed Sep. 11, 2008, Cervin et al.
Altschul, et al, "Gapped BLAST and PSI-BLAST: a new generation of protein database search programs" Nucleic Acids Res, (1997), 25:3389-402.
Beaucage, et al., "Deoxynucleoside phosphoramidites—A new class of key intermediates for deoxypolynucleotide synthesis" Tetrahedron Lett, (1981), 22:1859-62.
Boel, et al., "Glucoamylases G1 and G2 from Aspergillus niger are synthesized from two different but closely related mRNAs", EMBO J, (1984), 3:1097-102.
Broun, et al., "Catalytic plasticity of fatty acid modification enzymes underlying chemical diversity of plant lipids", Science, (1998), 282:1315-7.

(Continued)

*Primary Examiner* — Maryam Monshipouri
(74) *Attorney, Agent, or Firm* — Danisco US Inc.

(57) ABSTRACT

The present invention relates to an alpha-amylase blend, including a *B. stearothermophilus* alpha-amylase (AmyS) wherein the amino acid at position S242 is substituted and a *B. licheniformis* alpha-amylase The invention also relates to processes using the alpha-amylase blends for starch liquefaction and saccharification, ethanol production, and a sweetener production.

13 Claims, 20 Drawing Sheets

(56) References Cited

U.S. PATENT DOCUMENTS

| | | |
|---|---|---|
| 2008/0220498 A1 | 9/2008 | Cervin et al. |
| 2008/0293610 A1 | 11/2008 | Shaw et al. |
| 2009/0117642 A1 | 5/2009 | Power et al. |
| 2009/0143270 A1 | 6/2009 | Svendsen et al. |
| 2009/0238923 A1 | 9/2009 | Shaw et al. |
| 2009/0252828 A1 | 10/2009 | Cascao-Pereira et al. |
| 2009/0280527 A1 | 11/2009 | Bisgard-Frantzen et al. |
| 2009/0314286 A1 | 12/2009 | Cuevas et al. |
| 2010/0021587 A1 | 1/2010 | Chang et al. |
| 2010/0048446 A1 | 2/2010 | Cascao-Pereira et al. |
| 2010/0099597 A1 | 4/2010 | Bisgard-Frantzen et al. |
| 2010/0099598 A1 | 4/2010 | Bisgard-Frantzen et al. |

FOREIGN PATENT DOCUMENTS

| | | |
|---|---|---|
| EP | 0063909 A2 | 11/1982 |
| EP | 0218272 A1 | 4/1987 |
| EP | 0238023 A2 | 9/1987 |
| EP | 0238216 A1 | 9/1987 |
| EP | 0252666 A2 | 1/1988 |
| EP | 0252730 A2 | 1/1988 |
| EP | 0258068 A2 | 3/1988 |
| EP | 0260105 A2 | 3/1988 |
| EP | 0271155 | 6/1988 |
| EP | 0271156 | 6/1988 |
| EP | 0305216 A1 | 3/1989 |
| EP | 0318204 | 5/1989 |
| EP | 0318279 | 5/1989 |
| EP | 0331376 A2 | 9/1989 |
| EP | 0346136 | 12/1989 |
| EP | 0346137 | 12/1989 |
| EP | 0407225 A1 | 1/1991 |
| EP | 0414197 | 2/1991 |
| EP | 0429124 | 5/1991 |
| EP | 0481547 | 4/1992 |
| EP | 0495257 A1 | 7/1992 |
| EP | 0516553 | 12/1992 |
| EP | 0516555 | 12/1992 |
| EP | 0518719 | 12/1992 |
| EP | 0518720 | 12/1992 |
| EP | 0518721 | 12/1992 |
| EP | 0530635 | 3/1993 |
| EP | 0530870 | 3/1993 |
| EP | 0533239 | 3/1993 |
| EP | 0554943 | 8/1993 |
| EP | 0516554 | 9/1993 |
| EP | 0561446 | 9/1993 |
| EP | 0561452 | 9/1993 |
| EP | 1199356 | 4/2002 |
| EP | 1538155 | 6/2005 |
| GB | 1296839 A | 11/1972 |
| GB | 1372034 A | 10/1974 |
| GB | 1483591 A | 8/1977 |
| GB | 2200132 | 7/1988 |
| GB | 2228945 | 9/1990 |
| GB | 2234980 | 2/1991 |
| JP | 64-074992 A | 3/1989 |
| WO | WO89/06270 A1 | 7/1989 |
| WO | WO89/06279 A1 | 7/1989 |
| WO | WO89/09259 | 10/1989 |
| WO | WO91/00353 A2 | 1/1991 |
| WO | WO91/16422 A1 | 10/1991 |
| WO | WO91/17243 A1 | 11/1991 |
| WO | WO92/05249 A1 | 4/1992 |
| WO | WO92/06154 | 4/1992 |
| WO | WO92/06157 | 4/1992 |
| WO | WO92/06165 A1 | 4/1992 |
| WO | WO92/06221 A1 | 4/1992 |
| WO | WO92/08777 | 5/1992 |
| WO | WO92/19708 A1 | 11/1992 |
| WO | WO92/19709 A1 | 11/1992 |
| WO | WO92/19729 A1 | 11/1992 |
| WO | WO93/03129 | 2/1993 |
| WO | WO93/04153 | 3/1993 |
| WO | WO93/10210 | 5/1993 |
| WO | WO93/17089 | 9/1993 |
| WO | WO93/18129 | 9/1993 |
| WO | WO93/21297 | 10/1993 |
| WO | WO93/21299 | 10/1993 |
| WO | WO93/24618 A1 | 12/1993 |
| WO | WO93/25651 | 12/1993 |
| WO | WO94/01541 A1 | 1/1994 |
| WO | WO94/02597 A1 | 2/1994 |
| WO | WO94/07998 | 4/1994 |
| WO | WO94/18314 A1 | 8/1994 |
| WO | WO91/17244 | 11/1994 |
| WO | WO94/25578 A1 | 11/1994 |
| WO | WO94/25583 A1 | 11/1994 |
| WO | WO95/02044 | 1/1995 |
| WO | WO95/06720 A1 | 3/1995 |
| WO | WO95/10602 A1 | 4/1995 |
| WO | WO95/14783 A1 | 6/1995 |
| WO | WO95/14807 A1 | 6/1995 |
| WO | WO95/21247 A1 | 8/1995 |
| WO | WO95/22615 A1 | 8/1995 |
| WO | WO95/22625 A1 | 8/1995 |
| WO | WO95/24471 | 9/1995 |
| WO | WO95/26397 A1 | 10/1995 |
| WO | WO95/30744 A2 | 11/1995 |
| WO | WO95/35381 A1 | 12/1995 |
| WO | WO96/00292 A1 | 1/1996 |
| WO | WO96/00343 | 1/1996 |
| WO | WO96/11262 | 4/1996 |
| WO | WO96/12012 A1 | 4/1996 |
| WO | WO96/13580 A1 | 5/1996 |
| WO | WO96/23873 A1 | 8/1996 |
| WO | WO96/27002 A1 | 9/1996 |
| WO | WO96/28567 A1 | 9/1996 |
| WO | WO96/29397 | 9/1996 |
| WO | WO96/34108 | 10/1996 |
| WO | WO96/39528 A2 | 12/1996 |
| WO | WO97/00324 A1 | 1/1997 |
| WO | WO97/04079 A1 | 2/1997 |
| WO | WO97/06775 | 2/1997 |
| WO | WO97/07202 A1 | 2/1997 |
| WO | WO97/07205 A1 | 2/1997 |
| WO | WO97/42825 | 11/1997 |
| WO | WO97/43424 A1 | 11/1997 |
| WO | WO98/08940 | 3/1998 |
| WO | WO98/12307 | 3/1998 |
| WO | WO98/15257 A1 | 4/1998 |
| WO | WO98/20115 | 5/1998 |
| WO | WO98/20116 A1 | 5/1998 |
| WO | WO98/23732 A2 | 6/1998 |
| WO | WO98/34946 A1 | 8/1998 |
| WO | WO99/01544 | 1/1999 |
| WO | WO99/19467 A1 | 4/1999 |
| WO | WO99/20770 A2 | 4/1999 |
| WO | WO99/25846 | 5/1999 |
| WO | WO99/28448 | 6/1999 |
| WO | WO99/15124 | 9/1999 |
| WO | WO99/49740 A1 | 10/1999 |
| WO | WO00/04136 | 1/2000 |
| WO | WO00/32758 | 6/2000 |
| WO | WO00/60060 A2 | 10/2000 |
| WO | WO01/04273 | 1/2001 |
| WO | WO01/14629 | 3/2001 |
| WO | WO01/34899 | 5/2001 |
| WO | WO02/10355 | 2/2002 |
| WO | WO02/14490 A2 | 2/2002 |
| WO | WO02/092797 | 11/2002 |
| WO | WO2004/091544 A | 8/2004 |
| WO | WO2004/113551 | 12/2004 |
| WO | WO2005/056783 | 6/2005 |
| WO | WO2005111203 | 11/2005 |
| WO | WO2006/002643 A2 | 1/2006 |
| WO | WO2006/037483 | 4/2006 |
| WO | WO2006/043178 | 4/2006 |
| WO | WO2006/043178 A2 | 4/2006 |
| WO | WO2006/060062 | 6/2006 |
| WO | WO2007/079938 B1 | 7/2007 |
| WO | WO2008/097620 A1 | 8/2008 |
| WO | WO2008/153925 A2 | 12/2008 |

| | | | |
|---|---|---|---|
| WO | WO2009/061378 | | 5/2009 |
| WO | WO 2009/061379 | * | 5/2009 |
| WO | WO2009/061379 | | 5/2009 |

OTHER PUBLICATIONS

Cayot, et al., "The quantification of protein amino groups by the trinitrobenzenesulfonic acid method: a reexamination", Anal Biochem, (1997), 249:184-200.

Chica, et al., " Semi-rational approaches to engineering enzyme activity: combining the benefits of directed evolution and rational design", Curr Opin Biotechnol, (2005), 16:378-84.

Conti, et al., "Capillary isoelectric focusing: the problem of protein solubility", Journ Chrom, (1997) 757:237-45.

Dartois, et al., "Cloning, nucleotide sequence and expression in Escherichia coli of a lipase gene from Bacillus subtilis 168", Biochim Biophys Acta, (1992), 1131:253-60.

Devos, et al., "Practical limits of function prediction", Proteins, (2000), 41:98-107.

Engelen, et al., "Simple and rapid determination of phytase activity", J AOAC Int, (1994), 77:760-4.

Fogarty, et al., Progress in Industrial Microbiology, vol. 15, pp. 112-115, 1979.

Freire, et al., "Differential Scanning Calorimetry", Methods Mol Biol, (1995), 40:191-218.

Gaboriaud, et al., "Hydrophobic cluster analysis: an efficient new way to compare and analyse amino acid sequences", FEBS Letters, (1987), 224:149-55.

Gray, et al., "Structural Genes Encoding the Termophiliic .alpha.-amylase of *Bacillus stearothermophilus* and *Bacillus licheniformis*", Journal of Bacteriology, (1986), 166:635-43.

Hage, et al., "Efficient manganese catalysts for low-temperature bleaching", Nature, (1994), 369:637-9.

Hahn, et al., "Regulatory inputs for the synthesis of ComK, the competence transcription factor of *Bacillus subtilis*", Molecular Microbiology, (1996), 21:763-75.

Holm, et al., "Random mutagenesis used to probe the structure and function of *Bacillus stearothermophilus* alpha-amylase", Protein Eng, (1990), 3:181-91.

Huber, et al., "Protein fold recognition without Boltzmann statistics or explicit physical basis", Protein Sci, (1998), 7:142-9.

Kaushik et al., "Why is trehalose an exceptional protein stabilizer? An analysis of the thermal stability of proteins in the presence of the compatible osmolyte trehalose", J Biol Chem, (2003), 278: 26458-65.

Kim, et al., "Changes in Optimum PH and Thermostability of Alpha-Amylase from *Bacillus Licheniformis* by Site-Directed Mutagenesis of his 235 and ASP 328" Bulletin of the Korean Chemical Society, (1994), 15:832-5.

Lin, et al., "A gene encoding for an alpha-amylase from thermophilic *Bacillus sp*. strain TS-23 and its expression in *Escherichia coli*", J Appl Microbiol, (1997), 82:325-34.

Matthes, H.W.D. et al. "Simultaneous rapid chemical synthesis of over one hundred oligonucleotides on a microscale." *EMBO J.* 3(4): 801-805, Apr. 1984.

McKenzie, T. et al. "The nucleotide sequence of pUB110: some salient features in relation to replication and its regulation." *Plasmid* 15(2): 93-103, Mar. 1986.

Miller, "Use of dinitrosalicylic acid reagent for determination of reducing sugar", Anal. Chem., (1959) 31:426-428.

Morinaga, Y. et al. "Improvement of Oligonucleotide-Directed Site-Specific Mutagenesis Using Double-Stranded Plasmid DNA." *Bio/Technology* 2(7): 636-639, Jul. 1984.

Morris, et al., "The effect of wash temperature on removal of particulate and oily soil from fabrics of varying fiber content", Textile Research Journal, (1982), 52:280-6.

Needleman, S.B. et al. "A general method applicable to the search for similarities in the amino acid sequence of two proteins." J. Mol. Biol 48(3): 443-53, Mar. 1970.

Neidhardt, F.C. et al. "Culture Medium for Enterobacteria." *J. Bacteriol*. 119(3): 736-747, Sep. 1, 1974.

Nelson, R.M. et al. "A general method of site-specific mutagenesis using a modification of the Thermus aquaticus polymerase chain reaction." *Analytical Biochemistry* 180(1): 147-151, Jul. 1989.

Nielsen J.E. et al. "Protein Engineering of bacterial Alpha-amylases", Biochimica et Biophysica Acta, Amsterdam, vol. 1543, No. 2, Dec. 29, 2000, pp. 253-274, XP 000984337, ISSN 0006-30002.

Pearson, W.R. et al. "Improved Tools for Biological Sequence Comparison." *Proc. Natl. Acad. Sci. USA* 85(8): 2444-2448, Apr. 15, 1988.

Q12N92: Database UnitProt [Online], Aug. 22, 2006 "Subname: Full=Alpha amylase, catalytic region; Flags: Precursor;" XP 00254542 Retrieved from FBO, accession No. UNIPROT:Q12N92 Database accession No. Q12N92, http://www.uniprot.org/uniprot/Q12N92.

Russell et al., "Rational modification of enzyme catalysis by engineering surface charge," Nature 328: 496-500 (1987).

Saiki, R.K. et al. "Primer-directed enzymatic amplification of DNA with a thermostable DNA polymerase." Science 239(4839): 487-491, Jan. 29, 1988.

Seffernick et al., Melamine deaminase and Atrazine chlorohydrolase: 98 percent identical but functionally different. J. Bacteriol., 2001, vol. 183 (8): 2405-2410.

Sen et al. "Developments in Directed Evolution for Improving Enzyme Functions," Appl. Biochem. Biotechnol. 143(3):212-223, 2007.

Suzuki, et al., "Amino acid residues stabilizing a Bacillus alpha-amylase against irreversible thermoinactivation", J Biol Chem, (1989), 264:18933-8.

Tomazic S J et al. "Why is one Bacillus Alpha-Amylase more resistant against irreversible thermoinactivation than another?" Journal of Biological Chemistry, American Society of Biolochmical Biologists, Birmingham, US, vol. 263, No. 7, Mar. 5, 1988, pp. 3092-3096, XP 001015592, ISSN 0021,-9258.

Tsukamoto, A. et al. "Nucleotide sequence of the maltohexaose-producing amylase gene from an alkalophilic *Bacillus sp*. #707 and structural similarity to liquefying type alpha-amylases." *Biochemical and Biophysical Research Communications* 151(1): 25-31, Feb. 29, 1988.

Vogtentanz, G. et al. "A *Bacillus subtilis* fusion protein system to produce soybean Bowman-Birk protease inhibitor." *Protein Expression and Purification* 55(1): 40-52, Sep. 2007.

Whisstock et al., Prediction of protein function from protein sequence and structure. Q. Rev. Biophysics., 2003, vol. 36 (3): 307-340.

Witkowski et al., Conversion of b-ketoacyl synthase to a Malonyl Decarboxylase by replacement of the active cysteine with glutamine. Biochemistry, 1999, vol. 38: 11643-11650.

International Search Report for PCT/US2008/012410, mailed May 13, 2009.

International Search Report for PCT/US2008/012411, mailed Jul. 7, 2009.

International Search Report for PCT/US2008/012412, mailed Jul. 21, 2009.

International Search Report for PCT/US2008/012413, mailed Sep. 30, 2009.

* cited by examiner

```
                        1                                                50
SEQID No  1    (1)  -AAPFNGTMMQYFEWYLPDDGTLWTKVANEANNLSSLGITALWLPPAYKG
SEQID No  2    (1)  -AAPFNGTMMQYFEWYLPDDGTLWTKVANEANNLSSLGITALWLPPAYKG
SEQID No  3    (1)  -AAPFNGTMMQYFEWYLPDDGTLWTKVANEANNLSSLGITALWLPPAYKG
SEQID No  4    (1)  -AAPFNGTMMQYFEWYLPDDGTLWTKVANEANNLSSLGITALWLPPAYKG
SEQID No  5    (1)  -AAPFNGTMMQYFEWYLPDDGTLWTKVANEANNLSSLGITALWLPPAYKG
SEQID No  6    (1)  HHNGTNGTMMQYFEWYLPNDGNHWNRLNSDASNLKSKGITAVWIPPAWKG
SEQID No  7    (1)  --ANLNGTLMQYFEWYMPNDGQHWKRLQNDSAYLAEHGITAVWIPPAYKG
SEQID No  8    (1)  --ANLNGTLMQYFEWYMPNDGQHWRRLQNDSAYLAEHGITAVWIPPAYKG
SEQID No  9    (1)  ----VNGTLMQYFEWYTPNDGQHWKRLQNDAEHLSDIGITAVWIPPAYKG
SEQID No 10    (1)  HHNGTNGTMMQYFEWYLPNDGNHWNRLRSDASNLKDKGISAVWIPPAWKG
SEQID No 11    (1)  HHNGTNGTMMQYFEWHLPNDGNHWNRLRDDASNLRNRGITAIWIPPAWKG
SEQID No 12    (1)  HHNGTNGTMMQYFEWHLPNDGNHWNRLRDDAANLKSKGITAVWIPPAWKG
SEQID No 13    (1)  --DGLNGTMMQYYEWHLENDGQHWNRLHDDAAALSDAGITAIWIPPAYKG
SEQID No 14    (1)  --DGLNGTMMQYYEWHLENDGQHWNRLHDDAEALSNAGITAIWIPPAYKG
SEQID No 15    (1)  -AAPFNGTMMQYFEWYLPDDGTLWTKVANEANNLSSLGITALWLPPAYKG
Consensus      (1)     A  NGTMMQYFEWYLPNDGQHW RL NDA NLSS GITALWIPPAYKG
                        51                                               100
SEQID No  1   (50)  TSRSDVGYGVYDLYDLGEFNQKGTVRTKYGTKAQYLQAIQAAHAAGMQVY
SEQID No  2   (50)  TSRSDVGYGVYDLYDLGEFNQKGTVRTKYGTKAQYLQAIQAAHAAGMQVY
SEQID No  3   (50)  TSRSDVGYGVYDLYDLGEFNQKGTVRTKYGTKAQYLQAIQAAHAAGMQVY
SEQID No  4   (50)  TSRSDVGYGVYDLYDLGEFNQKGTVRTKYGTKAQYLQAIQAAHAAGMQVY
SEQID No  5   (50)  TSRSDVGYGVYDLYDLGEFNQKGTVRTKYGTKAQYLQAIQAAHAAGMQVY
SEQID No  6   (51)  ASQNDVGYGAYDLYDLGEFNQKGTVRTKYGTRSQLQAAVTSLKNNGIQVY
SEQID No  7   (49)  TSQADVGYGAYDLYDLGEFHQKGTVRTKYGTKGELQSAIKSLHSRDINVY
SEQID No  8   (49)  TSQADVGYGAYDLYDLGEFHQKGTVRTKYGTKGELQSAIKSLHSRDINVY
SEQID No  9   (47)  LSQSDNGYGPYDLYDLGEFQQKGTVRTKYGTKSELQDAIGSLHSRNVQVY
SEQID No 10   (51)  ASQNDVGYGAYDLYDLGEFNQKGTIRTKYGTRNQLQAAVNALKSNGIQVY
SEQID No 11   (51)  TSQNDVGYGAYDLYDLGEFNQKGTVRTKYGTRSQLESAIHALKNNGVQVY
SEQID No 12   (51)  TSQNDVGYGAYDLYDLGEFNQKGTVRTKYGTRSQLQGAVTSLKNNGIQVY
SEQID No 13   (49)  NSQADVGYGAYDLYDLGEFNQKGTVRTKYGTKAQLERAIGSLKSNDINVY
SEQID No 14   (49)  NSQADVGYGAYDLYDLGEFNQKGTVRTKYGTKAQLERAIGSLKSNDINVY
SEQID No 15   (50)  TSRSDVGYGVYDLYDLGEFNQKGTVRTKYGTKAQYLQAIQAAHAAGMQVY
Consensus     (51)  TSQSDVGYGAYDLYDLGEFNQKGTVRTKYGTKAQL  AI ALHA GIQVY
                        101                                              150
SEQID No  1  (100)  ADVVFDHKGGADGTEWVDAVEVNPSDRNQEISGTYQIQAWTKFDFPGRGN
SEQID No  2  (100)  ADVVFDHKGGADGTEWVDAVEVNPSDRNQEISGTYQIQAWTKFDFPGRGN
SEQID No  3  (100)  ADVVFDHKGGADGTEWVDAVEVNPSDRNQEISGTYQIQAWTKFDFPGRGN
SEQID No  4  (100)  ADVVFDHKGGADGTEWVDAVEVNPSDRNQEISGTYQIQAWTKFDFPGRGN
SEQID No  5  (100)  ADVVFDHKGGADGTEWVDAVEVNPSDRNQEISGTYQIQAWTKFDFPGRGN
SEQID No  6  (101)  GDVVMNHKGGADATEMVRAVEVNPNNRNQEVTGEYTIEAWTRFDFPGRGN
SEQID No  7   (99)  GDVVINHKGGADATEDVTAVEVDPADRNRVISGEHLIKAWTHFHFPGRGS
SEQID No  8   (99)  GDVVINHKGGADATEDVTAVEVDPADRNRVISGEHLIKAWTHFHFPGRGS
SEQID No  9   (97)  GDVVLNHKAGADATEDVTAVEVNPANRNQETSEEYQIKAWTDFRFPGRGN
SEQID No 10  (101)  GDVVMNHKGGADATEMVRAVEVNPNNRNQEVSGEYTIEAWTKFDFPGRGN
SEQID No 11  (101)  GDVVMNHKGGADATENVLAVEVNPNNRNQEISGDYTIEAWTKFDFPGRGN
SEQID No 12  (101)  GDVVMNHKGGADGTEMVNAVEVNRSNRNQEISGEYTIEAWTKFDFPGRGN
SEQID No 13   (99)  GDVVMNHKMGADFTEAVQAVQVNPTNRWQDISGAYTIDAWTGFDFSGRNN
SEQID No 14   (99)  GDVVMNHKLGADFTEAVQAVQVNPSNRWQDISGVYTIDAWTGFDFPGRNN
SEQID No 15  (100)  ADVVFDHKGGADGTEWVDAVEVNPSDRNQEISGTYQIQAWTKFDFPGRGN
Consensus    (101)  GDVVMNHKGGADGTE V AVEVNPSDRNQEISG Y I AWTKFDFPGRGN
```

*FIG. 1A*

```
                        151                                              200
SEQID No 1     (150)    TYSSFKWRWYHFDGVDWDESRKLS-RIYKFRGIGKAWDWEVDTENGNYDY
SEQID No 2     (150)    TYSSFKWRWYHFDGVDWDESRKLS-RIYKFRGIGKAWDWEVDTENGNYDY
SEQID No 3     (150)    TYSSFKWRWYHFDGVDWDESRKLS-RIYKFRGIGKAWDWEVDTENGNYDY
SEQID No 4     (150)    TYSSFKWRWYHFDGVDWDESRKLS-RIYKFRGIGKAWDWEVDTENGNYDY
SEQID No 5     (150)    TYSSFKWRWYHFDGVDWDESRKLS-RIYKFRGIGKAWDWEVDTENGNYDY
SEQID No 6     (151)    THSSFKWRWYHFDGVDWDQSRRLNNRIYKFRGHGKAWDWEVDTENGNYDY
SEQID No 7     (149)    TYSDFKWHWYHFDGTDWDESRKLN-RIYKFQG--KAWDWEVSNENGNYDY
SEQID No 8     (149)    TYSDFKWHWYHFDGTDWDESRKLN-RIYKFQG--KAWDWEVSNENGNYDY
SEQID No 9     (147)    TYSDFKWHWYHFDGADWDESRKIS-RIFKFRGEGKAWDWEVSSENGNYDY
SEQID No 10    (151)    THSNFKWRWYHFDGVDWDQSRKLNNRIYKFRGDGKGWDWEVDTENGNYDY
SEQID No 11    (151)    TYSDFKWRWYHFDGVDWDQSRQFQNRIYKFRGDGKAWDWEVDSENGNYDY
SEQID No 12    (151)    THSNFKWRWYHFDGTDWDQSRQLQNKIYKFRGIGKAWDWEVDIENGNYDY
SEQID No 13    (149)    AYSDFKWRWFHFNGVDWDQRYQEN-HIFRFAN--TNWNWRVDEENGNYDY
SEQID No 14    (149)    AYSDFKWRWFHFNGVDWDQRYQEN-HLFRFAN--TNWNWRVDEENGNYDY
SEQID No 15    (150)    TYSSFKWRWYHFDGVDWDESRKLS-RIYKFRG--KAWDWEVDTEFGNYDY
Consensus      (151)    TYS FKWRWYHFDGVDWDESRKLN RIYKFRG GKAWDWEVDTENGNYDY
                        201                                              250
SEQID No 1     (199)    LMYADLDMDHPEVVTELKNWGKWYVNTTNIDGFRLDAVKHIKFSFFPDWL
SEQID No 2     (199)    LMYADLDMDHPEVVTELKNWGKWYVNTTNIDGFRLDAVKHIKFSFFPDWL
SEQID No 3     (199)    LMYADLDMDHPEVVTELKNWGKWYVNTTNIDGFRLDAVKHIKFAFFPDWL
SEQID No 4     (199)    LMYADLDMDHPEVVTELKNWGKWYVNTTNIDGFRLDAVKHIKFQFFPDWL
SEQID No 5     (199)    LMYADLDMDHPEVVTELKNWGKWYVNTTNIDGFRLDAVKHIKFEFFPDWL
SEQID No 6     (201)    LMYADIDMDHPEVVNELRNWGVWYTNTLGLDGFRIDAVKHIKYSFTRDWI
SEQID No 7     (196)    LMYADIDYDHPDVAAEIKRWGTWYANELQLDGFRLDAVKHIKFSFLRDWV
SEQID No 8     (196)    LMYADIDYDHPDVAAEIKRWGTWYANELQLDGFRLDAVKHIKFSFLRDWV
SEQID No 9     (196)    LMYADVDYDHPDVVAETKKWGIWYANELSLDGFRIDAAKHIKFSFLRDWV
SEQID No 10    (201)    LMYADIDMDHPEVVNELRNWGVWYTNTLGLDGFRIDAVKHIKYSFTRDWI
SEQID No 11    (201)    LMYADVDMDHPEVVNELRRWGEWYTNTLNLDGFRIDAVKHIKYSFTRDWL
SEQID No 12    (201)    LMYADIDMDHPEVINELRNWGVWYTNTLNLDGFRIDAVKHIKYSYTRDWL
SEQID No 13    (196)    LLGSNIDFSHPEVQDELKDWGSWFTDELDLDGYRLDAIKHIPFWYTSDWV
SEQID No 14    (196)    LLGSNIDFSHPEVQEELKDWGSWFTDELDLDGYRLDAIKHIPFWYTSDWV
SEQID No 15    (197)    LMYADLDMDHPEVVTELKNWGKWYVNTTNIDGFRLDAVKHIKFSFFPDWL
Consensus      (201)    LMYADIDMDHPEVV ELKNWG WY NTLNLDGFRLDAVKHIKFSF  DWL
                        251                                              300
SEQID No 1     (249)    SYVRSQTGKPLFTVGEYWSYDINKLHNYITKTNGTMSLFDAPLHNKFYTA
SEQID No 2     (249)    SYVRSQTGKPLFTVGEYWSYDINKLHNYITKTNGTMSLFDAPLHNKFYTA
SEQID No 3     (249)    SYVRSQTGKPLFTVGEYWSYDINKLHNYITKTNGTMSLFDAPLHNKFYTA
SEQID No 4     (249)    SYVRSQTGKPLFTVGEYWSYDINKLHNYITKTNGTMSLFDAPLHNKFYTA
SEQID No 5     (249)    SYVRSQTGKPLFTVGEYWSYDINKLHNYITKTNGTMSLFDAPLHNKFYTA
SEQID No 6     (251)    NHVRSATGKNMFAVAEFWKNDLGAIENYLQKTNWNHSVFDVPLHYNLYNA
SEQID No 7     (246)    NHVREKTGKEMFTVAEYWQNDLGALENYLNKTNFNHSVFDVPLHYQFHAA
SEQID No 8     (246)    NHVREKTGKEMFTVAEYWQNDLGALENYLNKTNFNHSVFDVPLHYQFHAA
SEQID No 9     (246)    QAVRQATGKEMFTVAEYWQNNAGKLENYLNKTSFNQSVFDVPLHFNLQAA
SEQID No 10    (251)    NHVRSATGKNMFAVAEFWKNDLGAIENYLNKTNWNHSVFDVPLHYNLYNA
SEQID No 11    (251)    THVRNATGKEMFAVAEFWKNDLGALENYLNKTNWNHSVFDVPLHYNLYNA
SEQID No 12    (251)    THVRNTTGKPMFAVAEFWKNDLAAIENYLNKTSWNHSVFDVPLHYNLYNA
SEQID No 13    (246)    RHQRNEADQDLFVVGEYWKDDVGALEFYLDEMNWEMSLFDVPLNYNFYRA
SEQID No 14    (246)    RHQRSEADQDLFVVGEYWKDDVGALEFYLDEMNWEMSLFDVPLNYNFYRA
SEQID No 15    (247)    SYVRSQTGKPLFTVGEYWSYDINKLHNYITKTNGTMSLFDAPLHNKFYTA
Consensus      (251)    SHVRS TGK LFTVGEYW  DIGALENYL KTNW MSLFDVPLHYNFY A
```

*FIG. 1B*

```
                        301                                                350
SEQID No  1    (299) SKSGGAFDMRTLMTNTLMKDQPTLAVTFVDNHDTEPGQALQSWVDPWFKP
SEQID No  2    (299) SKSGGAFDMRTLMTNTLMKDQPTLAVTFVDNHDTEPGQALQSWVDPWFKP
SEQID No  3    (299) SKSGGAFDMRTLMTNTLMKDQPTLAVTFVDNHDTEPGQALQSWVDPWFKP
SEQID No  4    (299) SKSGGAFDMRTLMTNTLMKDQPTLAVTFVDNHDTEPGQALQSWVDPWFKP
SEQID No  5    (299) SKSGGAFDMRTLMTNTLMKDQPTLAVTFVDNHDTEPGQALQSWVDPWFKP
SEQID No  6    (301) SKSGGNYDMRNIFNGTVVQRHPSHAVTFVDNHDSQPEEALESFVEEWFKP
SEQID No  7    (296) STQGGYDMRKLLNGTVVSKHPLKSVTFVDNHDTQPGQSLESTVQTWFKP
SEQID No  8    (296) STQGGYDMRKLLNGTVVSKHPLKSVTFVDNHDTQPGQSLESTVQTWFKP
SEQID No  9    (296) SSQGGYDMRRLLDGTVVSRHPEKAVTFVENHDTQPGQSLESTVQTWFKP
SEQID No 10    (301) SKSGGNYDMRQIFNGTVVQRHPMHAVTFVDNHDSQPEEALESFVEEWFKP
SEQID No 11    (301) SNSGGNYDMAKLLNGTVVQKHPMHAVTFVDNHDSQPGESLESFVQEWFKP
SEQID No 12    (301) SNSGGYFDMRNILNGSVVQKHPIHAVTFVDNHDSQPGEALESFVQSWFKP
SEQID No 13    (296) SQQGGSYDMRNILRGSLVEAHPMHAVTFVDNHDTQPGESLESWVADWFKP
SEQID No 14    (296) SKQGGSYDMRNILRGSLVEAHPIHAVTFVDNHDTQPGESLESWVADWFKP
SEQID No 15    (297) SKSGGAFDMRTLMTNTLMKDQPTLAVTFVDNHDTEPGQALQSWVDPWFKP
Consensus      (301) SKSGGAYDMR LL GTLV  HP  AVTFVDNHDTQPGQALESWVD WFKP
                        351                                                400
SEQID No  1    (349) LAYAFILTRQEGYPCVFYGDYYGIPQYN---IPSLKSKIDPLLIARRDYA
SEQID No  2    (349) LAYAFILTRQEGYPCVFYGDYYGIPQYN---IPSLKSKIDPLLIARRDYA
SEQID No  3    (349) LAYAFILTRQEGYPCVFYGDYYGIPQYN---IPSLKSKIDPLLIARRDYA
SEQID No  4    (349) LAYAFILTRQEGYPCVFYGDYYGIPQYN---IPSLKSKIDPLLIARRDYA
SEQID No  5    (349) LAYAFILTRQEGYPCVFYGDYYGIPQYN---IPSLKSKIDPLLIARRDYA
SEQID No  6    (351) LAYALTLTREQGYPSVFYGDYYGIPTHG---VPAMRSKIDPILEARQKYA
SEQID No  7    (346) LAYAFILTRESGYPQVFYGDMYGTKGDSQREIPALKHKIEPILKARKQYA
SEQID No  8    (346) LAYAFILTRESGYPQVFYGDMYGTKGDSQREIPALKHKIEPILKARKQYA
SEQID No  9    (346) LAYAFILTRESGYPQVFYGDMYGTKGTSPKEIPSLKDNIEPILKARKEYA
SEQID No 10    (351) LAYALTLTREQGYPSVFYGDYYGIPTHG---VPAMKSKIDPILEARQKYA
SEQID No 11    (351) LAYALILTREQGYPSVFYGDYYGIPTHS---VPAMKAKIDPILEARQNFA
SEQID No 12    (351) LAYALILTREQGYPSVFYGDYYGIPTHG---VPSMKSKIDPLLQARQTYA
SEQID No 13    (346) LAYATILTREGGYPNVFYGDYYGIPNDN----ISAKKDMIDELLDARQNYA
SEQID No 14    (346) LAYATILTREGGYPNVFYGDYYGIPNDN----ISAKKDMIDELLDARQNYA
SEQID No 15    (347) LAYAFILTRQEGYPCVFYGDYYGIPQYN---IPSLKSKIDPLLIARRDYA
Consensus      (351) LAYAFILTRE GYP VFYGDYYGIPQYN    IPSLKSKIDPLL ARR YA
                        401                                                450
SEQID No  1    (396) YGTQHDYLDHSDIIGWTREGVTEKPGSGLAALITDGPGGSKWMYVGKQHA
SEQID No  2    (396) YGTQHDYLDHSDIIGWTREGVTEKPGSGLAALITDGPGGSKWMYVGKQHA
SEQID No  3    (396) YGTQHDYLDHSDIIGWTREGVTEKPGSGLAALITDGPGGSKWMYVGKQHA
SEQID No  4    (396) YGTQHDYLDHSDIIGWTREGVTEKPGSGLAALITDGPGGSKWMYVGKQHA
SEQID No  5    (396) YGTQHDYLDHSDIIGWTREGVTEKPGSGLAALITDGPGGSKWMYVGKQHA
SEQID No  6    (398) YGKQNDYLDHHNIIGWTREGNTAHPNSGLATIMSDGAGGSKWMFVGRNKA
SEQID No  7    (396) YGAQHDYFDHHDIVGWTREGDSSVANSGLAALITDGPGGAKRMYVGRQNA
SEQID No  8    (396) YGAQHDYFDHHDIVGWTREGDSSVANSGLAALITDGPGGAKRMYVGRQNA
SEQID No  9    (396) YGPQHDYIDHPDVIGWTREGDSSAAKSGLAALITDGPGGSKRMYAGLKNA
SEQID No 10    (398) YGRQNDYLDHHNIIGWTREGNTAHPNSGLATIMSDGAGGNKWMFVGRNKA
SEQID No 11    (398) YGTQHDYFDHHNIIGWTREGNTTHPNSGLATIMSDGPGGEKWMYVGQNKA
SEQID No 12    (398) YGTQHDYFDHHDIIGWTREGDSSHPNSGLATIMSDGPGGNKWMYVGKHKA
SEQID No 13    (393) YGTQHDYFDHWDVVGWTREGSSSRPNSGLATIMSNGPGGSKWMYVGRQNA
SEQID No 14    (393) YGTQHDYFDHWDIVGWTREGTSSRPNSGLATIMSNGPGGSKWMYVGQQHA
SEQID No 15    (394) YGTQHDYLDHSDIIGWTREGGTEKPGSGLAALITDGPGGSKWMYVGKQHA
Consensus      (401) YGTQHDYLDH DIIGWTREG TSKPNSGLAALITDGPGGSKWMYVGKQ A
```

*FIG. 1C*

```
              451                                              500
SEQID No  1  (446) GKVFYDLTGNRSDTVTINSDGWGEFKVNGGSVSVWVPRKTTVSTIARPIT
SEQID No  2  (446) GKVFYDLTGNRSDTVTINSDGWGEFKVNGGSVSVWVPRKTT---------
SEQID No  3  (446) GKVFYDLTGNRSDTVTINSDGWGEFKVNGGSVSVWVPRKTTVSTIARPIT
SEQID No  4  (446) GKVFYDLTGNRSDTVTINSDGWGEFKVNGGSVSVWVPRKTTVSTIARPIT
SEQID No  5  (446) GKVFYDLTGNRSDTVTINSDGWGEFKVNGGSVSVWVPRKTTVSTIARPIT
SEQID No  6  (448) GQVWSDITGNRTGTVTINADGWGNFSVNGGSVSIWVNK------------
SEQID No  7  (446) GETWHDITGNRSEPVVINSEGWGEFHVNGGSVSIYVQR------------
SEQID No  8  (446) GETWHDITGNRSEPVVINSEGWGEFHVNGGSVSIYVQR------------
SEQID No  9  (446) GETWYDITGNRSDTVKIGSDGWGEFHVNDGSVSIYVQK------------
SEQID No 10  (448) GQVWTDITGNRAGTVTINADGWGNFSVNGGSVSIWVNK------------
SEQID No 11  (448) GQVWHDITGNKPGTVTINADGWANFSVNGGSVSIWVKR------------
SEQID No 12  (448) GQVWRDITGNRSGTVTINADGWGNFTVNGGAVSVWVKQ------------
SEQID No 13  (443) GQTWTDLTGNNGASVTINGDGWGEFFTNGGSVSVYVNQ------------
SEQID No 14  (443) GQTWTDLTGNHAASVTINGDGWGEFFTNGGSVSVYVNQ------------
SEQID No 15  (444) GKVFYDLTGNRSDTVTINSDGWGEFKVNGGSVSVWVPRKTTVS-------
Consensus    (451) G VWYDLTGNRSDTVTINSDGWGEF VNGGSVSVWV R
              501       520
SEQID No  1  (496) TRPWTGEFVRWTEPRLVAWP
SEQID No  2  (487) --------------------
SEQID No  3  (496) TRPWTGEFVRWTEPRLVAWP
SEQID No  4  (496) TRPWTGEFVRWTEPRLVAWP
SEQID No  5  (496) TRPWTGEFVRWTEPRLVAWP
SEQID No  6  (486) --------------------
SEQID No  7  (484) --------------------
SEQID No  8  (484) --------------------
SEQID No  9  (484) --------------------
SEQID No 10  (486) --------------------
SEQID No 11  (486) --------------------
SEQID No 12  (486) --------------------
SEQID No 13  (481) --------------------
SEQID No 14  (481) --------------------
SEQID No 15  (487) --------------------
Consensus    (501)
```

*FIG. 1D*

```
                        1                                                50
SEQID No 1       (1)  -AAPFNGTMMQYFEWYLPDDGTLWTKVANEANNLSSLGITALWLPPAYKG
SEQID No 6       (1)  HHNGTNGTMMQYFEWYLPNDGNHWNRLNSDASNLKSKGITAVWIPPAWKG
Consensus        (1)        NGTMMQYFEWYLP DG   W KL  DA NL S GITALWIPPAWKG
                        51                                               100
SEQID No 1      (50)  TSRSDVGYGVYDLYDLGEFNQKGTVRTKYGTKAQYLQAIQAAHAAGMQVY
SEQID No 6      (51)  ASQNDVGYGAYDLYDLGEFNQKGTVRTKYGTRSQLQAAVTSLKNNGIQVY
Consensus       (51)     S DVGYG YDLYDLGEFNQKGTVRTKYGTKAQ    AI A    GIQVY
                        101                                              150
SEQID No 1     (100)  ADVVFDHKGGADGTEWVDAVEVNPSDRNQEISGTYQIQAWTKFDFPGRGN
SEQID No 6     (101)  GDVVMNHKGGADATEMVRAVEVNPNNRNQEVTGEYTIEAWTRFDFPGRGN
Consensus      (101)   DVV  HKGGADATE V AVEVNP  RNQEISG Y I AWTKFDFPGRGN
                        151                                              200
SEQID No 1     (150)  TYSSFKWRWYHFDGVDWDESRKLS-RIYKFRGIGKAWDWEVDTENGNYDY
SEQID No 6     (151)  THSSFKWRWYHFDGVDWDQSRRLNNRIYKFRGHGKAWDWEVDTENGNYDY
Consensus      (151)  THSSFKWRWYHFDGVDWD SRKL   RIYKFRG GKAWDWEVDTENGNYDY
                        201                                              250
SEQID No 1     (199)  LMYADLDMDHPEVVTELKNWGKWYVNTTNIDGFRLDAVKHIKFSFFPDWL
SEQID No 6     (201)  LMYADIDMDHPEVVNELRNWGVWYTNTLGLDGFRIDAVKHIKYSFTRDWI
Consensus      (201)  LMYADIDMDHPEVV ELKNWG WY NT  IDGFRIDAVKHIKFSF  DWI
                        251                                              300
SEQID No 1     (249)  SYVRSQTGKPLFTVGEYWSYDINKLHNYITKTNGTMSLFDAPLHNKFYTA
SEQID No 6     (251)  NHVRSATGKNMFAVAEFWKNDLGAIENYLQKTNWNHSVFDVPLHYNLYNA
Consensus      (251)    HVRS TGK LF VAEFW  DI  I NYI KTN   SLFD PLH Y  A
                        301                                              350
SEQID No 1     (299)  SKSGGAFDMRTLMTNTLMKDQPTLAVTFVDNHDTEPGQALQSWVDPWFKP
SEQID No 6     (301)  SKSGGNYDMRNIFNGTVVQRHPSHAVTFVDNHDSQPEEALESFVEEWFKP
Consensus      (301)  SKSGG  FDMR I    TLM  PS AVTFVDNHDS P  AL SFVD WFKP
                        351                                              400
SEQID No 1     (349)  LAYAFILTRQEGYPCVFYGDYYGIPQYNIPSLKSKIDPLLIARRDYAYGT
SEQID No 6     (351)  LAYALTLTREQGYPSVFYGDYYGIPTHGVPAMRSKIDPILEARQKYAYGK
Consensus      (351)  LAYA  LTR  GYP VFYGDYYGIP H  IPALKSKIDPIL AR  YAYG
                        401                                              450
SEQID No 1     (399)  QHDYLDHSDIIGWTREGVTEKPGSGLAALITDGPGGSKWMYVGKQHAGKV
SEQID No 6     (401)  QNDYLDHHNIIGWTREGNTAHPNSGLATIMSDGAGGSKWMFVGRNKAGQV
Consensus      (401)  Q DYLDH  IIGWTREG T P SGLA IISDG GGSKWMFVGKN AG V
                        451                                              500
SEQID No 1     (449)  FYDLTGNRSDVTINSDWGEFKVNGGSVSVWVPRKTTVSTIARPITTRP
SEQID No 6     (451)  WSDITGNRTGTVTINADWGNFSVNGGSVSIWVNK--------------
Consensus      (451)  F DITGNRS TVTINADWG F VNGGSVSIWV K
                        501       517
SEQID No 1     (499)  WTGEFVRWTEPRLVAWP
SEQID No 6     (486)  -----------------
Consensus      (501)
```

*FIG. 4A*

```
                              1                                                  50
SEQID No 1      (1)   AAPFNGTMMQYFEWYLPDDGTLWTKVANEANNLSSLGITALWLPPAYKGT
SEQID No 8      (1)   -ANLNGTLMQYFEWYMPNDGQHWRRLQNDSAYLAEHGITAVWIPPAYKGT
Consensus       (1)    A  NGTLMQYFEWYLP DG  W KL NDA  LA GITALWIPPAYKGT
                              51                                                100
SEQID No 1     (51)   SRSDVGYGVYDLYDLGEFNQKGTVRTKYGTKAQYLQAIQAAHAAGMQVYA
SEQID No 8     (50)   SQADVGYGAYDLYDLGEFHQKGTVRTKYGTKGELQSAIKSLHSRDINVYG
Consensus      (51)   S ADVGYG YDLYDLGEF QKGTVRTKYGTKA   AI A HA   INVYA
                              101                                               150
SEQID No 1    (101)   DVVFDHKGGADGTEWVDAVEVNPSDRNQEISGTYQIQAWTKFDFPGRGNT
SEQID No 8    (100)   DVVINHKGGADATEDVTAVEVDPADRNRVISGEHLIKAWTHFHFPGRGST
Consensus     (101)   DVV  HKGGADATE V AVEV PADRN  ISG H I AWT F FPGRG T
                              151                                               200
SEQID No 1    (151)   YSSFKWRWYHFDGVDWDESRKLSRIYKFRGIGKAWDWEVDTENGNYDYLM
SEQID No 8    (150)   YSDFKWHWYHFDGTDWDESRKLNRIYKFQ--GKAWDWEVSNENGNYDYLM
Consensus     (151)   YS FKW WYHFDG DWDESRKL RIYKF   GKAWDWEV  ENGNYDYLM
                              201                                               250
SEQID No 1    (201)   YADLDMDHPEVVTELKNWGKWYVNTTNIDGFRLDAVKHIKFSFFPDWLSY
SEQID No 8    (198)   YADIDYDHPDVAAEIKRWGTWYANELQLDGFRLDAVKHIKFSFLRDWVNH
Consensus     (201)   YADID DHPDV  EIK WG WY N  NIDGFRLDAVKHIKFSF  DWL H
                              251                                               300
SEQID No 1    (251)   VRSQTGKPLFTVGEYWSYDINKLHNYITKTNGTMSLFDAPLHNKFYTASK
SEQID No 8    (248)   VREKTGKEMFTVAEYWQNDLGALENYLNKTNFNHSVFDVPLHYQFHAAST
Consensus     (251)   VR  TGK  LFTVAEYW  DI L NYI KTN   SLFD PLH   FH AS
                              301                                               350
SEQID No 1    (301)   SGGAFDMRTLMTNTLMKDQPTLAVTFVDNHDTEPGQALQSWVDPWFKPLA
SEQID No 8    (298)   QGGGYDMRKLLNGTVVSKHPLKSVTFVDNHDTQPGQSLESTVQTWFKPLA
Consensus     (301)    GGA FDMR LL  TLM  P  AVTFVDNHDT PGQAL S V  WFKPLA
                              351                                               400
SEQID No 1    (351)   YAFILTRQEGYPCVFYGDYYGIP---QYNIPSLKSKIDPLLIARRDYAYG
SEQID No 8    (348)   YAFILTRESGYPQVFYGDMYGTKGDSQREIPALKHKIEPILKARKQYAYG
Consensus     (351)   YAFILTR  GYP VFYGD YG     Q  IPALK KIDPIL ARK YAYG
                              401                                               450
SEQID No 1    (398)   TQHDYLDHSDIIGWTREGVTEKPGSGLAALITDGPGGSKWMYVGKQHAGK
SEQID No 8    (398)   AQHDYFDHHDIVGWTREGDSSVANSGLAALITDGPGGAKRMYVGRQNAGE
Consensus     (401)    QHDY DH DIIGWTREG S     SGLAALITDGPGGAK MYVGKQ AG
                              451                                               500
SEQID No 1    (448)   VFYDLTGNRSDTVTINSDGWGEFKVNGGSVSVWVPRKTTVSTIARPITTR
SEQID No 8    (448)   TWHDITGNRSEPVVINSEGWGEFHVNGGSVSIYVQR-------------
Consensus     (451)    FHDITGNRSD V INSDGWGEF VNGGSVSIWV R
                              501     518
SEQID No 1    (498)   PWTGEFVRWTEPRLVAWP
SEQID No 8    (484)   ------------------
Consensus     (501)
```

*FIG. 4B*

```
                      1                                              50
SEQID No 1    (1)   AAPFNGTMMQYFEWYLPDDGTLWTKVANEANNLSSLGITALWLPPAYKGT
SEQID No 9    (1)   ---VNGTLMQYFEWYTPNDGQHWKRLQNDAEHLSDIGITAVWIPPAYKGL
Consensus     (1)      NGTLMQYFEWY P DG  W KL NDA  LS IGITALWIPPAYKG
                      51                                             100
SEQID No 1    (51)  SRSDVGYGVYDLYDLGEFNQKGTVRTKYGTKAQYLQAIQAAHAAGMQVYA
SEQID No 9    (48)  SQSDNGYGPYDLYDLGEFQQKGTVRTKYGTKSELQDAIGSLHSRNVQVYG
Consensus     (51)  S SD GYG YDLYDLGEFNQKGTVRTKYGTKA    AI A HA  MQVYA
                      101                                            150
SEQID No 1    (101) DVVFDHKGGADGTEWVDAVEVNPSDRNQEISGTYQIQAWTKFDFPGRGNT
SEQID No 9    (98)  DVVLNHKAGADATEDVTAVEVNPANRNQETSEEYQIKAWTDFRFPGRGNT
Consensus     (101) DVV  HKAGADATE V AVEVNPA RNQE S  YQI AWT F FPGRGNT
                      151                                            200
SEQID No 1    (151) YSSFKWRWYHFDGVDWDESRKLSRIYKFRGIGKAWDWEVDTENGNYDYLM
SEQID No 9    (148) YSDFKWHWYHFDGADWDESRKISRIFKFRGEGKAWDWEVSSENGNYDYLM
Consensus     (151) YS FKW WYHFDG DWDESRKISRIFKFRG GKAWDWEV SENGNYDYLM
                      201                                            250
SEQID No 1    (201) YADLDMDHPEVVTELKNWGKWYVNTTNIDGFRLDAVKHIKFSFPPDWLSY
SEQID No 9    (198) YADVDYDHPDVVAETKKWGIWYANELSLDGFRIDAAKHIKFSFLRDWVQA
Consensus     (201) YADLD DHPDVV E K WG WY N   IDGFRIDA KHIKFSF  DWL
                      251                                            300
SEQID No 1    (251) VRSQTGKPLFTVGEYWSYDINKLHNYITKTNGTMSLFDAPLHNKFYTASK
SEQID No 9    (248) VRQATGKEMFTVAEYWQNNAGKLENYLNKTSFNQSVFDVPLHFNLQAASS
Consensus     (251) VR  TGK  LFTVAEYW     KL NYI KT   SLFD PLH       AS
                      301                                            350
SEQID No 1    (301) SGGAFDMRTLMTNTLMKDQPTLAVTFVDNHDTEPGQALQSWVDPWFKPLA
SEQID No 9    (298) QGGGYDMRRLLDGTVVSRHPEKAVTFVENHDTQPGQSLESTVQTWFKPLA
Consensus     (301)  GGAFDMR LL  TLM  P  AVTFVDNHDT PGQAL S V  WFKPLA
                      351                                            400
SEQID No 1    (351) YAFILTRQEGYPCVFYGDYYGIPQYN---IPSLKSKIDPLLIARRDYAYG
SEQID No 9    (348) YAFILTRESGYPQVFYGDMYGTKGTSPKEIPSLKDNIEPILKARKEYAYG
Consensus     (351) YAFILTR  GYP VFYGD YG         IPSLK  IDPIL ARKDYAYG
                      401                                            450
SEQID No 1    (398) TQHDYLDHSDIIGWTREGVTEKPGSGLAALITDGPGGSKWMYVGKQHAGK
SEQID No 9    (398) PQHDYIDHPDVIGWTRECDSSAAKSCLAALITDGPGGSKRMYAGLKNACE
Consensus     (401)  QHDYIDH DIIGWTREG S   SGLAALITDGPGGSK MY G   AG
                      451                                            500
SEQID No 1    (448) VFYDLTGNRSDTVTINSDGWGEFKVNGGSVSVWVPRKTTVSTIARPITTR
SEQID No 9    (448) TWYDITGNRSDTVKIGSDGWGEFHVNDGSVSIYVQK--------------
Consensus     (451)   FYDITGNRSDTV I SDGWGEF VN GSVSIWV K
                      501       518
SEQID No 1    (498) PWTGEFVRWTEPRLVAWP
SEQID No 9    (484) ------------------
Consensus     (501)
```

*FIG. 4C*

```
                       1                                                  50
SEQID No 1    (1)    -AAPFNGTMMQYFEWYLPDDGTLWTKVANEANNLSSLGITALWLPPAYKG
SEQID No 10   (1)    HHNGTNGTMMQYFEWYLPNDGNHWNRLRSDASNLKDKGISAVWIPPAWKG
Consensus     (1)          NGTMMQYFEWYLP DG  W KL  DA NL   GISALWIPPAWKG
                       51                                                100
SEQID No 1    (50)   TSRSDVGYGVYDLYDLGEFNQKGTVRTKYGTKAQYLQAIQAAHAAGMQVY
SEQID No 10   (51)   ASQNDVGYGAYDLYDLGEFNQKGTIRTKYGTRNQLQAAVNALKSNGIQVY
Consensus     (51)    S  DVGYG YDLYDLGEFNQKGTIRTKYGTK Q   AINA  A GIQVY
                       101                                               150
SEQID No 1    (100)  ADVVFDHKGGADGTEWVDAVEVNPSDRNQEISGTYQIQAWTKFDFPGRGN
SEQID No 10   (101)  GDVVMNHKGGADATEMVRAVEVNPNNRNQEVSGEYTIEAWTKFDFPGRGN
Consensus     (101)  ADVV  HKGGADATE V AVEVNP  RNQEISG  Y  I AWTKFDFPGRGN
                       151                                               200
SEQID No 1    (150)  TYSSFKWRWYHFDGVDWDESRKLS-RIYKFRGIGKAWDWEVDTENGNYDY
SEQID No 10   (151)  THSNFKWRWYHFDGVDWDQSRKLNNRIYKFRGDGKGWDWEVDTENGNYDY
Consensus     (151)  THS FKWRWYHFDGVDWD SRKL  RIYKFRG GKAWDWEVDTENGNYDY
                       201                                               250
SEQID No 1    (199)  LMYADLDMDHPEVVTELKNWGKWYVNTTNIDGFRLDAVKHIKFSFFPDWL
SEQID No 10   (201)  LMYADIDMDHPEVVNELRNWGVWYTNTLGLDGFRIDAVKHIKYSFTRDWI
Consensus     (201)  LMYADIDMDHPEVV ELKNWG WY NT  IDGFRIDAVKHIKFSF  DWI
                       251                                               300
SEQID No 1    (249)  SYVRSQTGKPLFTVGEYWSYDINKLHNYITKTNGTMSLFDAPLHNKFYTA
SEQID No 10   (251)  NHVRSATGKNMFAVAEFWKNDLGAIENYLNKTNWNHSVFDVPLHYNLYNA
Consensus     (251)    HVRS TGK  LF VAEFW  DI  I NYI KTN    SLFD PLH   Y A
                       301                                               350
SEQID No 1    (299)  SKSGGAFDMRTLMTNTLMKDQPTLAVTFVDNHDTEPGQALQSWVDPWFKP
SEQID No 10   (301)  SKSGGNYDMRQIFNGTVVQRHPMHAVTFVDNHDSQPEEALESFVEEWFKP
Consensus     (301)  SKSGG  FDMR I    TLM  P  AVTFVDNHDS P  AL SFVD WFKP
                       351                                               400
SEQID No 1    (349)  LAYAFILTRQEGYPCVFYGDYYGIPQYNIPSLKSKIDPLLIARRDYAYGT
SEQID No 10   (351)  LAYALTLTREQGYPSVFYGDYYGIPTHGVPAMKSKIDPILEARQKYAYGR
Consensus     (351)  LAYA  LTR  GYP VFYGDYYGIP H  IPA LKSKIDPIL AR  YAYG
                       401                                               450
SEQID No 1    (399)  QHDYLDHSDIIGWTREGVTEKPGSGLAALITDGPGGSKWMYVGKQHAGKV
SEQID No 10   (401)  QNDYLDHHNIIGWTREGNTAHPNSGLATIMSDGAGGNKWMFVGRNKAGQV
Consensus     (401)  Q DYLDH  IIGWTREG T  P SGLA IISDG GG KWMFVGKN AG V
                       451                                               500
SEQID No 1    (449)  FYDLTGNRSDTVTINSDGWGEFKVNGGSVSVWVPRKTTVSTIARPITTRP
SEQID No 10   (451)  WTDITGNRAGTVTINADGWGNFSVNGGSVSIWVNK---------------
Consensus     (451)  F DITGNRA TVTINADGWG F VNGGSVSIWV K
                       501     517
SEQID No 1    (499)  WTGEFVRWTEPRLVAWP
SEQID No 10   (486)  -----------------
Consensus     (501)
```

*FIG. 4D*

```
                          1                                                50
SEQID No 1    (1)   -AAPFNGTMMQYFEWYLPDDGTLWTKVANEANNLSSLGITALWLPPAYKG
SEQID No 11   (1)   HHNGTNGTMMQYFEWHLPNDGNHWNRLRDDASNLRNRGITAIWIPPAWKG
Consensus     (1)         NGTMMQYFEWHLP DG  W KL  DA NL   GITAIWIPPAWKG
                          51                                               100
SEQID No 1    (50)  TSRSDVGYGVYDLYDLGEFNQKGTVRTKYGTKAQYLQAIQAAHAACMQVY
SEQID No 11   (51)  TSQNDVGYGAYDLYDLGEFNQKGTVRTKYGTRSQLESAIHALKNNGVQVY
Consensus     (51)  TS  DVGYG YDLYDLGEFNQKGTVRTKYGTKAQ   AI A   GMQVY
                          101                                              150
SEQID No 1    (100) ADVVFDHKGCADGTEWVDAVEVNPSDRNQEISGTYQIQAWTKFDFPGRGN
SEQID No 11   (101) GDVVMNHKGGADATENVLAVEVNPNNRNQEISGDYTIEAWTKFDFPGRGN
Consensus     (101)  ADVV  HKGGADATE V AVEVNP  RNQEISG Y I  AWTKFDFPGRGN
                          151                                              200
SEQID No 1    (150) TYSSFKWRWYHFDGVDWDESR-KLSRIYKFRGIGKAWDWEVDTENGNYDY
SEQID No 11   (151) TYSDFKWRWYHFDGVDWDQSRQFQNRIYKFRGDGKAWDWEVDSENGNYDY
Consensus     (151) TYS FKWRWYHFDGVDWD SR     RIYKFRG GKAWDWEVDSENGNYDY
                          201                                              250
SEQID No 1    (199) LMYADLDMDHPEVVTELKNWGKWYVNTTNIDGFRLDAVKHIKFSFFPDWL
SEQID No 11   (201) LMYADVDMDHPEVVNELRRWGEWYTNTLNLDGFRIDAVKHIKYSFTRDWL
Consensus     (201) LMYADLDMDHPEVV ELK WG WY NT NIDGFRIDAVKHIKFSF  DWL
                          251                                              300
SEQID No 1    (249) SYVRSQTGKPLFTVGEYWSYDINKLHNYITKTNGTMSLFDAPLHNKFYTA
SEQID No 11   (251) THVRNATGKEMFAVAEFWKNDLGALENYLNKTNWNHSVFDVPLHYNLYNA
Consensus     (251)  HVR  TGK LF VAEFW  DI L  NYI KTN    SLFD PLH Y A
                          301                                              350
SEQID No 1    (299) SKSGGAFDMRTLMTNTLMKDQPTLAVTFVDNHDTEPGQALQSWVDPWFKP
SEQID No 11   (301) SNSGGNYDMAKLLNGTVVQKHPMHAVTFVDNHDSQPGESLESFVQEWFKP
Consensus     (301) S SGG  FDM  LL  TLM    P AVTFVDNHDS PG AL SFV  WFKP
                          351                                              400
SEQID No 1    (349) LAYAFILTRQEGYPCVFYGDYYGIPQYNIPSLKSKIDPLLIARRDYAYGT
SEQID No 11   (351) LAYALILTREQGYPSVFYGDYYGIPTHSVPAMKAKIDPILEARQNFAYGT
Consensus     (351) LAYA ILTR  GYP VFYGDYYGIP H  IPALKAKIDPIL AR   FAYGT
                          401                                              450
SEQID No 1    (399) QHDYLDHSDIIGWTREGVTEKPGSGLAALITDGPGGSKWMYVGKQHAGKV
SEQID No 11   (401) QHDYFDHHNIIGWTREGNTTHPNSGLATIMSDGPGGEKWMYVGQNKAGQV
Consensus     (401) QHDY DH  IIGWTREG T  P  SGLA IISDGPGG KWMYVG N AG V
                          451                                              500
SEQID No 1    (449) FYDLTGNRSDTVTINSDGWGEPKVNGGSVSVWVPRKTTVSTIARPITTRP
SEQID No 11   (451) WHDITGNKPGTVTINADGWANPSVNGGSVSIWVKR----------------
Consensus     (451) FHDITGNK  TVTINADGWA   F VNGGSVSIWV R
                          501             517
SEQID No 1    (499) WTGEFVRWTEPRLVAWP
SEQID No 11   (486) -----------------
Consensus     (501)
```

FIG. 4E

```
                          1                                                50
SEQID No 1      (1)   -AAPFNGTMMQYFEWYLPDDGTLWTKVANEANNLSSLGITALWLPPAYKG
SEQID No 12     (1)   HHNGTNGTMMQYFEWHLPNDGNHWNRLRDDAANLKSKGITAVWIPPAWKG
Consensus       (1)          NGTMMQYFEWHLP DG  W KL  DA NL S GITALWIPPAWKG
                          51                                              100
SEQID No 1     (50)   TSRSDVGYGVYDLYDLGEFNQKGTVRTKYGTKAQYLQAIQAAHAAGMQVY
SEQID No 12    (51)   TSQNDVGYGAYDLYDLGEFNQKGTVRTKYGTRSQLQGAVTSLKNNGIQVY
Consensus      (51)   TS  DVGYG YDLYDLGEFNQKGTVRTKYGTKAQ    AI A    GIQVY
                          101                                             150
SEQID No 1    (100)   ADVVFDHKGGADGTEWVDAVEVNPSDRNQEISGTYQIQAWTKFDFPGRGN
SEQID No 12   (101)   GDVVMNHKGGADGTEMVNAVEVNRSNRNQEISGEYTIEAWTKFDFPGRGN
Consensus     (101)   ADVV  HKGGADGTE V AVEVN S RNQEISG Y I  AWTKFDFPGRGN
                          151                                             200
SEQID No 1    (150)   TYSSFKWRWYHFDGVDWDESR-KLSRIYKFRGIGKAWDWEVDTENGNYDY
SEQID No 12   (151)   THSNFKWRWYHFDGTDWDQSRQLQNKIYKFRGTGKAWDWEVDIENGNYDY
Consensus     (151)   THS FKWRWYHFDG DWD SR    KIYKFRG GKAWDWEVD ENGNYDY
                          201                                             250
SEQID No 1    (199)   LMYADLDMDHPEVVTELKNWGKWYVNTTNIDGFRLDAVKHIKFSFPPDWL
SEQID No 12   (201)   LMYADIDMDHPEVINELRNWGVWYTNTLNLDGFRIDAVKHIKYSYTRDWL
Consensus     (201)   LMYADIDMDHPEVI ELKNWG WY NT NIDGFRIDAVKHIKFSF  DWL
                          251                                             300
SEQID No 1    (249)   SYVRSQTGKPLFTVGEYWSYDINKLHNYITKTNGTMSLFDAPLHNKFYTA
SEQID No 12   (251)   THVRNTTGKPMFAVAEFWKNDLAAIENYLNKTSWNHSVFDVPLHYNLYNA
Consensus     (251)   S VR  TGKPLF VAEFW  DI I NYI KT    SLFD PLH Y  A
                          301                                             350
SEQID No 1    (299)   SKSGGAFDMRTLMTNTLMKDQPTLAVTFVDNHDTEPGQALQSWVDPWFKP
SEQID No 12   (301)   SNSGGYFDMRNILNGSVVQKHPIHAVTFVDNHDSQPGEALESFVQSWFKP
Consensus     (301)   S SGG FDMR  IL  SLM   P  AVTFVDNHDS PG AL SFV  WFKP
                          351                                             400
SEQID No 1    (349)   LAYAFILTRQEGYPCVFYGDYYGIPQYNIPSLKSKIDPLLIARRDYAYGT
SEQID No 12   (351)   LAYALILTREQGYPSVFYGDYYGIPTHGVPSMKSKIDPLLQARQTYAYGT
Consensus     (351)   LAYA ILTR  GYP VFYGDYYGIP H IPSLKSKIDPLL AR  YAYGT
                          401                                             450
SEQID No 1    (399)   QHDYLDHSDIIGWTREGVTEKPGSGLAALITDGPGGSKWMYVGKQHAGKV
SEQID No 12   (401)   QHDYFDHHDIIGWTREGDSSHPNSGLATIMSDGPGGNKWMYVGKHKAGQV
Consensus     (401)   QHDY DH DIIGWTREG  S  P  SGLA IISDGPGG KWMYVGK  AG V
                          451                                             500
SEQID No 1    (449)   FYDLTGNRSDTVTINSDGWGEFKVNGGSVSVWVPRKTTVSTIARPITTRP
SEQID No 12   (451)   WRDITCNRSGTVTINADGWGNFTVNGGAVSVWVKQ---------------
Consensus     (451)   F DITGNRS TVTINADGWG F VNGGAVSVWV
                          501             517
SEQID No 1    (499)   WTGEFVRWTEPRLVAWP
SEQID No 12   (486)   -----------------
Consensus     (501)
```

*FIG. 4F*

```
                        1                                                  50
SEQID No 1      (1)     AAPFNGTMMQYFEWYLPDDGTLWTKVANEANNLSSLGITALWLPPAYKGT
SEQID No 13     (1)     -DGLNGTMMQYYEWHLENDGQHWNRLHDDAAALSDAGITAIWIPPAYKGN
Consensus       (1)          NGTMMQYFEWHL  DG   W KL   DA  LS  GITAIWIPPAYKG
                        51                                                 100
SEQID No 1      (51)    SRSDVGYGVYDLYDLGEFNQKGTVRTKYGTKAQYLQAIQAAHAAGMQVYA
SEQID No 13     (50)    SQADVGYGAYDLYDLGEFNQKGTVRTKYGTKAQLERAIGSLKSNDINVYG
Consensus       (51)    S ADVGYG YDLYDLGEFNQKGTVRTKYGTKAQ   AI A  A   INVYA
                        101                                                150
SEQID No 1      (101)   DVVFDHKGGADGTEWVDAVEVNPSDRNQEISGTYQIQAWTKFDFPGRGNT
SEQID No 13     (100)   DVVMNHKMGADFTEAVQAVQVNPTNRWQDISGAYTIDAWTGFDFSGRNNA
Consensus       (101)   DVV   HK GAD TE V AV VNPS R QDISG Y I  AWT FDF GR N
                        151                                                200
SEQID No 1      (151)   YSSFKWRWYHFDGVDWDESRKLSRIYKFRGIGKAWDWEVDTENGNYDYLM
SEQID No 13     (150)   YSDFKWRWFHFNGVDWDQRYQENHIFRFANTN--WNWRVDEENGNYDYLL
Consensus       (151)   YS FKWRWFHF GVDWD      IFKF      W W VD ENGNYDYLL
                        201                                                250
SEQID No 1      (201)   YADLDMDHPEVVTELKNWGKWYVNTTNIDGFRLDAVKHIKFSFFPDWLSY
SEQID No 13     (198)   GSNIDFSHPEVQDELKDWGSWFTDELDLDGYRLDAIKHIPFWYTSDWVRH
Consensus       (201)     A ID  HPEV  ELK WG WF       IDGFRLDAIKHI F F DWL H
                        251                                                300
SEQID No 1      (251)   VRSQTGKPLFTVGEYWSYDINKLHNYITKTNGTMSLFDAPLHNKFYTASK
SEQID No 13     (248)   QRNEADQDLFVVGEYWKDDVGALEFYLDEMNWEMSLFDVPLNYNFYRASQ
Consensus       (251)    R     LF VGEYW  D I   L   YI   N  MSLFD PL  FY AS
                        301                                                350
SEQID No 1      (301)   SGGAFDMRTLMTNTLMKDQPTLAVTFVDNHDTEPGQALQSWVDPWFKPLA
SEQID No 13     (298)   QGGSYDMRNILRGSLVEAHPMHAVTFVDNHDTQPGESLESWVADWFKPLA
Consensus       (301)     GGAFDMR IL  SLM   P  AVTFVDNHDT PG AL SWV  WFKPLA
                        351                                                400
SEQID No 1      (351)   YAFILTRQEGYPCVFYGDYYGIPQYNIPSLKSKIDPLLIARRDYAYGTQH
SEQID No 13     (348)   YATILTREGGYPNVFYGDYYGIPNDNISAKKDMIDELLDARQNYAYGTQH
Consensus       (351)   YA ILTR  GYP VFYGDYYGIPN NI A K  ID LL AR  YAYGTQH
                        401                                                450
SEQID No 1      (401)   DYLDHSDIIGWTREGVTEKPGSGLAALITDGPGGSKWMYVGKQHAGKVFY
SEQID No 13     (398)   DYFDHWDVVGWTREGSSSRPNSGLATIMSNGPGGSKWMYVGRQNAGQTWT
Consensus       (401)   DY DH DIIGWTREG S KP SGLA IIS GPGGSKWMYVGKQ AG  F
                        451                                                500
SEQID No 1      (451)   DLTGNRSDTVTINSDGWGEFKVNGGSVSVWVPRKTTVSTIARPITTRPWT
SEQID No 13     (448)   DLTGNNGASVTINGDGWGEFFTNGGSVSVYVNQ-----------------
Consensus       (451)   DLTGN    SVTIN DGWGEF  NGGSVSVWV
                        501         515
SEQID No 1      (501)   GEFVRWTEPRLVAWP
SEQID No 13     (481)   ---------------
Consensus       (501)
```

*FIG. 4G*

```
                         1                                                50
SEQID No 1      (1)  AAPFNGTMMQYFEWYLPDDGTLWTKVANEANNLSSLGITALWLPPAYKGT
SEQID No 14     (1)  -DGLNGTMMQYYEWHLENDGQHWNRLHDDAEALSNAGITAIWIPPAYKGN
Consensus       (1)         NGTMMQYFEWHL  DG   W KL   DA   LS  GITAIWIPPAYKG
                         51                                               100
SEQID No 1     (51)  SRSDVGYGVYDLYDLGEFNQKGTVRTKYGTKAQYLQAIQAAHAAGMQVYA
SEQID No 14    (50)  SQADVGYGAYDLYDLGEFNQKGTVRTKYGTKAQLERAIGSLKSNDINVYG
Consensus      (51)  S  ADVGYG YDLYDLGEFNQKGTVRTKYGTKAQ      AI A  A   INVYA
                        101                                               150
SEQID No 1    (101)  DVVFDHKGGADGTEWVDAVEVNPSDRNQEISGTYQIQAWTKFDFPGRGNT
SEQID No 14   (100)  DVVMNHKLGADFTEAVQAVQVNPSNRWQDISGVYTIDAWTGFDFPGRNNA
Consensus     (101)  DVV    HK GAD TE V AV VNPS R QDISG Y I  AWT FDFPGR N
                        151                                               200
SEQID No 1    (151)  YSSFKWRWYHFDGVDWDESRKLSRIYKFRGIGKAWDWEVDTENGNYDYLM
SEQID No 14   (150)  YSDFKWRWFHFNGVDWDQRYQENHLFRFANTN--WNWRVDEENGNYDYLL
Consensus     (151)  YS FKWRWFHF GVDWD         IFKF     W W VD ENGNYDYLL
                        201                                               250
SEQID No 1    (201)  YADLDMDHPEVVTELKNWGKWYVNTTNIDGFRLDAVKHIKFSFFPDWLSY
SEQID No 14   (198)  GSNIDFSHPEVQEELKDWGSWFTDELDLDGYRLDAIKHIPFWYTSDWVRH
Consensus     (201)    A ID HPEV  ELK WG WF       IDGFRLDAIKHI F F DWL  H
                        251                                               300
SEQID No 1    (251)  VRSQTGKPLFTVGEYWSYDINKLHNYITKTNGTMSLFDAPLHNKFYTASK
SEQID No 14   (248)  QRSEADQDLFVVGEYWKDDVGALEFYLDEMNWEMSLFDVPLNYNFYRASK
Consensus     (251)   RS      LF VGEYW  D  L    YI   N  MSLFD PL  FY ASK
                        301                                               350
SEQID No 1    (301)  SGGAFDMRTLMTNTLMKDQPTLAVTFVDNHDTEPGQALQSWVDPWFKPLA
SEQID No 14   (298)  QGGSYDMRNILRGSLVEAHPIHAVTFVDNHDTQPGESLESWVADWFKPLA
Consensus     (301)    GGAFDMR IL  SLM   P  AVTFVDNHDT PG AL SWV  WFKPLA
                        351                                               400
SEQID No 1    (351)  YAFILTRQEGYPCVFYGDYYGIPQYNIPSLKSKIDPLLIARRDYAYGTQH
SEQID No 14   (348)  YATILTREGGYPNVFYGDYYGIPNDNISAKKDMIDELLDARQNYAYGTQH
Consensus     (351)  YA ILTR  GYP VFYGDYYGIPN NI A K  ID LL AR  YAYGTQH
                        401                                               450
SEQID No 1    (401)  DYLDHSDIIGWTREGVTEKPGSGLAALITDGPGGSKWMYVGKQHAGKVFY
SEQID No 14   (398)  DYFDHWDIVGWTREGTSSRPNSGLATIMSNGPGGSKWMYVGQQHAGQTWT
Consensus     (401)  DY DH DIIGWTREG S KP SGLA IIS GPGGSKWMYVG QHAG   F
                        451                                               500
SEQID No 1    (451)  DLTGNRSDTVTINSDGWGEFKVNGGSVSVWVPRKTTVSTIARPITTRPWT
SEQID No 14   (448)  DLTGNHAASVTINGDGWGEFFTNGGSVSVYVNQ-----------------
Consensus     (451)  DLTGN A  SVTIN DGWGEF   NGGSVSVWV
                        501         515
SEQID No 1    (501)  GEFVRWTEPRLVAWP
SEQID No 14   (481)  ---------------
Consensus     (501)
```

*FIG. 4H*

```
                         1                                                50
SEQID No  1    (  1)  AAPFNGTMMQYFEWYLPDDGTLWTKVANEANNLSSLGITALWLPPAYKGT
SEQID No 15    (  1)  AAPFNGTMMQYFEWYLPDDGTLWTKVANEANNLSSLGITALWLPPAYKGT
  Consensus    (  1)  AAPFNGTMMQYFEWYLPDDGTLWTKVANEANNLSSLGITALWLPPAYKGT
                        51                                               100
SEQID No  1    ( 51)  SRSDVGYGVYDLYDLGEFNQKGTVRTKYGTKAQYLQAIQAAHAAGMQVYA
SEQID No 15    ( 51)  SRSDVGYGVYDLYDLGEFNQKGTVRTKYGTKAQYLQAIQAAHAAGMQVYA
  Consensus    ( 51)  SRSDVGYGVYDLYDLGEFNQKGTVRTKYGTKAQYLQAIQAAHAAGMQVYA
                        101                                              150
SEQID No  1    (101)  DVVFDHKGGADGTEWVDAVEVNPSDRNQEISGTYQIQAWTKFDFPGRGNT
SEQID No 15    (101)  DVVFDHKGGADGTEWVDAVEVNPSDRNQEISGTYQIQAWTKFDFPGRGNT
  Consensus    (101)  DVVFDHKGGADGTEWVDAVEVNPSDRNQEISGTYQIQAWTKFDFPGRGNT
                        151                                              200
SEQID No  1    (151)  YSSFKWRWYHFDGVDWDESRKLSRIYKFRGIGKAWDWEVDTENGNYDYLM
SEQID No 15    (151)  YSSFKWRWYHFDGVDWDESRKLSRIYKFR---GKAWDWEVDTEFGNYDYLM
  Consensus    (151)  YSSFKWRWYHFDGVDWDESRKLSRIYKFR   GKAWDWEVDTE GNYDYLM
                        201                                              250
SEQID No  1    (201)  YADLDMDHPEVVTELKNWGKWYVNTTNIDGFRLDAVKHIKFSFFPDWLSY
SEQID No 15    (199)  YADLDMDHPEVVTELKNWGKWYVNTTNIDGFRLDAVKHIKFSFFPDWLSY
  Consensus    (201)  YADLDMDHPEVVTELKNWGKWYVNTTNIDGFRLDAVKHIKFSFFPDWLSY
                        251                                              300
SEQID No  1    (251)  VRSQTGKPLFTVGEYWSYDINKLHNYITKTNGTMSLFDAPLHNKFYTASK
SEQID No 15    (249)  VRSQTGKPLFTVGEYWSYDINKLHNYITKTNGTMSLFDAPLHNKFYTASK
  Consensus    (251)  VRSQTGKPLFTVGEYWSYDINKLHNYITKTNGTMSLFDAPLHNKFYTASK
                        301                                              350
SEQID No  1    (301)  SGGAFDMRTLMTNTLMKDQPTLAVTFVDNHDTEPGQALQSWVDPWFKPLA
SEQID No 15    (299)  SGGAFDMRTLMTNTLMKDQPTLAVTFVDNHDTEPGQALQSWVDPWFKPLA
  Consensus    (301)  SGGAFDMRTLMTNTLMKDQPTLAVTFVDNHDTEPGQALQSWVDPWFKPLA
                        351                                              400
SEQID No  1    (351)  YAFILTRQEGYPCVFYGDYYGIPQYNIPSLKSKIDPLLIARRDYAYGTQH
SEQID No 15    (349)  YAFILTRQEGYPCVFYGDYYGIPQYNIPSLKSKIDPLLIARRDYAYGTQH
  Consensus    (351)  YAFILTRQEGYPCVFYGDYYGIPQYNIPSLKSKIDPLLIARRDYAYGTQH
                        401                                              450
SEQID No  1    (401)  DYLDHSDIIGWTREGVTEKPGSGLAALITDGPGGSKWMYVGKQHAGKVFY
SEQID No 15    (399)  DYLDHSDIIGWTREGGTEKPGSGLAALITDGPGGSKWMYVGKQHAGKVFY
  Consensus    (401)  DYLDHSDIIGWTREG TEKPGSGLAALITDGPGGSKWMYVGKQHAGKVFY
                        451                                              500
SEQID No  1    (451)  DLTGNRSDTVTINSDGWGEFKVNGGSVSVWVPRKTTVSTIARPITTRPWT
SEQID No 15    (449)  DLTGNRSDTVTINSDGWGEFKVNGGSVSVWVPRKTTVS------------
  Consensus    (451)  DLTGNRSDTVTINSDGWGEFKVNGGSVSVWVPRKTTVS
                        501          515
SEQID No  1    (501)  GEFVRWTEPRLVAWP
SEQID No 15    (487)  ---------------
  Consensus    (501)
```

*FIG. 4I*

SEQ ID NO: 20: SPEZYME® FRED α-amylase amino acid sequence.

```
  1 TNLNGTLMQY FEWYTPNDGQ HWKRLQNDSA YLAEHGITAV WIPPAYKGTS
 51 QADVGYGAYD LYDLGEFHQK GTVRTKYGTK GELQSAIKSL HSRDINVYGD
101 VVINHKGGAD ATEDVTAVEV DPADRNRVIS GEYLIKAWTH FHFPGRGSTY
151 SDFKWHWYHF DGTDWDESRK LNRIYKFQGK AWDWEVDTEN GNYDYLMYAD
201 IDYDHPDVVA EIKRWGTWYA NELQLDGFRL DAVKHIKFSF FPDWLSYVRS
251 QTGKPLFTVG EYWSYDINKL HNYITKTNGT MSLFDAPLHN KFYTASKSGG
301 AFDMRTLMTN TLMKDQPTLA VTFVDNHDTE PGQALQSWVD PWFKPLAYAF
351 ILTRQEGYPC VFYGDYYGIP QYNIPSLKSK IDPLLIARRD YAYGKQNDYL
401 DHHNIIGWTR EGNTAHPNSG LATIMSDGAG GSKWMFVGRN KAGQVWSDIT
451 GNRTGTVTIN ADGWGNFSVN GGSVSIWVNK
```

*FIG. 15*

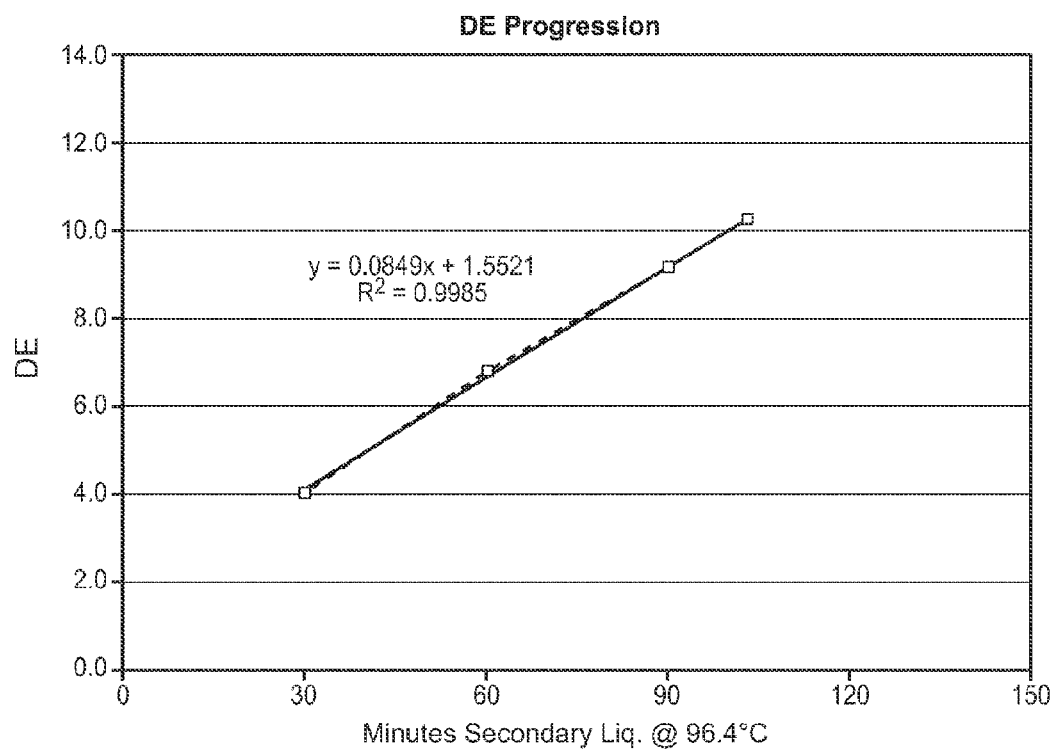

*FIG. 16*

ALPHA-AMYLASE BLENDS AND METHODS FOR USING SAID BLENDS

CROSS-REFERENCE TO RELATED APPLICATIONS

This application is a U.S. National Phase Application of International Application No. PCT/US2009/056613, filed Sep. 11, 2009, which claims priority to U.S. Provisional Application Ser. No. 61/100,092, filed Sep. 25, 2008 and to U.S. Provisional Application Ser. No. 61/238,891, filed Sep. 1, 2009, which are incorporated herein in their entireties.

SEQUENCE LISTING

A Sequence Listing, comprising SEQ ID NOS: 1-20, is attached and is incorporated by reference in its entirety.

FIELD OF INVENTION

Described herein is a blend of a *Geobacillus stearothermophilus* alpha-amylase and a *Bacillus licheniformis* alpha-amylase. The alpha-amylase blend described herein is suitable for numerous applications such as starch liquefaction and saccharification, ethanol production, and/or sweetener production.

BACKGROUND

Alpha-Amylases (alpha-1,4-glucan-4-glucanohydrolases, E.C. 3.2.1.1) constitute a group of enzymes, which catalyze hydrolysis of starch and other linear and branched 1,4-glucosidic oligo- and polysaccharides.

Amylases can be used commercially in the initial stages (liquefaction) of starch processing; in wet corn milling; in alcohol production; as cleaning agents in detergent matrices; in the textile industry for starch desizing; in baking applications; in the beverage industry; in oilfields in drilling processes; in deinking of recycled paper and in animal feed.

Alpha-amylases are isolated from a wide variety of bacterial, fungal, plant, and animal sources. Many industrially important α-amylases are isolated from *Bacillus* sp., in part because of the generally high capacity of *Bacillus* to secrete amylases into the growth medium. Furthermore, there is a need for blends of alpha-amylases, or variants thereof, which can capitalize on the best properties of at least two alpha-amylases from at least two bacterial strains.

For example, alpha-amylases isolated from *B. stearothermophilus* (AmyS) have been used in fuel ethanol applications because of rapid viscosity decreasing property. Fuel ethanol plants have 20-30 min of slurry time before slurry goes through the jet cooking step and in that 20-30 min viscosity has to be broken down for trouble-free pipe flow. However, certain alpha-amylases or variants thereof are not thermostable, so while they decrease the viscosity of a slurry over time, they suffer from lower DE slope and lower viscosity reduction in secondary liquefaction, where the slurry may be kept at 85-90° C. for up to 90-120 min.

There is therefore a need in the industry for the identification and optimization of amylases and their blends, useful in various production processes, for example, commercial starch liquefaction processes and ethanol production processes.

Low viscosity starch liquefacts are useful in the current ethanol production process. If a way could be found to produce such low viscosity liquefacts as fermentation feedstocks using an optimized blend of alpha-amylases, or variants thereof, this would represent a useful contribution to the art.

Furthermore, if a way could be found to treat whole ground grains with a blend of alpha-amylases, or variants thereof, from two different bacterial species to improve starch liquefaction, this would also represent a useful contribution to the art.

A further challenge in the preparation of fermentation feedstocks is that alpha amylases from *B. stearothermophilus*, for example, have been found to be less effective in hydrolyzing linear amylase, resulting in a retrograded insoluble residual starch under yeast fermentation conditions. The high level of residual starch in the yeast fermentation broth has been considered as one of the major factors influencing the evaporator fouling affecting the downstream processing operations in the ethanol process productions. Thus, if a way could be found to reduce residual insoluble starch in the fermentation broth using an optimized blend of alpha-amylases, or variants thereof, this would also represent a useful contribution to the art.

SUMMARY

A liquefaction process for whole ground grains in the fermentation process is described. The process comprises contacting an aqueous slurry containing whole ground grain with a blend of starch-liquefying alpha-amylases from at least two different bacterial species.

In one embodiment, the present invention comprises an alpha-amylase blend comprising: (i) a *B. stearothermophilus* alpha-amylase (AmyS) wherein the amino acid at position S242 is substituted, using the amino acid number system shown in SEQ ID NO: 2; and (ii) a *B. licheniformis* alpha-amylase. The blend may further comprise a phytase.

In one embodiment, a weight ratio of about 40% of the AmyS with the S242 substitution and about 60% *B. licheniformis* alpha-amylase can be used. In this manner, the superior properties of each enzyme, rapid viscosity reduction of starch liquefacts and thermostability, respectively, may be fully exploited in a method of fermenting alcohol. In another preferred embodiment, the weight ratio of AmyS with the S242 substitution to *B. licheniformis* alpha-amylase is 10:90 to exploit fully the properties of the enzymes in a method of making a sweetener. In other embodiments, the weight ratio of AmyS with the S242 substitution to *B. licheniformis* alpha-amylase may be 5:95, 15:85, 20:80, 25:75, 30:70, 50:50, 60:40, 70:30, 75:25, 80:20, 85:15, 90:10, or intermediate values thereof.

In another embodiment, an activity ratio of from about 1400 AAU/g to about 14000 AAU/g of the AmyS with the S242 substitution, and from about 8000 LU/g to about 19000 LU/g *B. licheniformis* alpha-amylase can be used. The ratio of AmyS with the S242 substitution to *B. licheniformis* alpha-amylase may be 1400 AAU/g:14000 LU/g, 2000 AAU/g: 15000 LU/g, 2100 AAU/g:16000 LU/g, 1900 AAU/g:17000 LU/g, or intermediate values thereof. In other embodiments the ratio of *B. licheniformis* alpha-amylase to AmyS with the S242 substitution is from about 5.5 LU/AAU to about 9.5 LU/AAU. The activity ratio of *B. licheniformis* alpha-amylase to AmyS with the S242 substitution is in the range of about 0.1 LU/AAU to about 9.5 LU/AAU. For example the activity ratio may be 0.1 LU/AAU, 0.2 LU/AAU, 0.3 LU/AAU, 0.4 LU/AAU, 0.5 LU/AAU, 1.0 LU/AAU, 1.5 LU/AAU, 2.0 LU/AAU, 2.5 LU/AAU, 3.0 LU/AAU, 4.0 LU/AAU, 5.0 LU/AAU, 5.5 LU/AAU, 6.0 LU/AAU, 6.5 LU/AAU, 7.0 LU/AAU, 7.5 LU/AAU, 8.0 LU/AAU, 8.5 LU/AAU, 9.0 LU/AAU, 9.5 LU/AAU or intermediate values thereof.

The AmyS may comprise the polypeptide sequence of SEQ ID NO: 1 or SEQ ID NO: 2, wherein the S242 residue is substituted. In a preferred embodiment, the AmyS comprises an amino acid sequence set forth in SEQ ID NO: 4, which has a S242Q substitution compared to SPEZYME® Xtra (SEQ ID NO: 2). This enzyme is designated herein as either "AmyS S242Q" or just "S242Q." In another embodiment, the AmyS may be selected from one of the AmyS enzymes comprising the polypeptide sequence of SEQ ID NOS: 6, 7, 8, 9, 10, 11, 12, 15 and 16, wherein the S242 residue is substituted.

The S242 substitution may be an S242A, S242E, S242Q, S242F, S242H, or S242N substitution. In one embodiment, the amino acid substitution at position S242 alters the thermostability of the AmyS. The AmyS with the substitution at position S242 may have a higher thermostability between about 80° C. and about 95° C. compared to an AmyS without the S242 substitution.

In one embodiment, the AmyS comprises an amino acid sequence having at least 60%, 70%, 80%, 85%, 90%, 95%, 98%, or 99% sequence identity to the AmyS of SEQ ID NO: 1, wherein the AmyS has alpha-amylase activity. The AmyS may comprise a substitution of a cysteine at amino acids 349 and 428, using SEQ ID NO: 1 for numbering. The AmyS also may comprise a substitution of N193 and/or V416. The AmyS also may comprise a deletion of amino acids 179 and 180, using SEQ ID NO: 1 for numbering.

The AmyS enzymes may have an altered amino acid sequence compared to a wild-type AmyS that alters one or more properties of the enzyme, e.g., substrate specificity, substrate binding, substrate cleavage pattern, thermal stability, pH/activity profile, pH/stability profile, stability towards oxidation, $Ca^{2+}$ dependency, and/or specific activity. For instance, the alteration may result in an enzyme that has a reduced $Ca^{2+}$ dependency and/or an altered pH/activity profile and/or thermostability, compared to a wild-type AmyS.

The *B. licheniformis* alpha-amylase may be a purified wild-type enzyme. The *B. licheniformis* alpha-amylase may have one or more amino acid substitutions of the wild-type sequence selected from the group consisting of M15T, H133Y, N188S, and A209V. In a preferred embodiment, the *B. licheniformis* alpha-amylase comprises the amino acid sequence shown in SEQ ID NO: 20, which is also know as SPEZYME® FRED. In one embodiment, the *B. licheniformis* alpha-amylase comprises an amino acid sequence having at least 60%, 70%, 80%, 85%, 90%, 95%, 96%, 97% 98%, or 99% sequence identity to SPEZYME® FRED (SEQ ID NO: 20).

The invention further relates to DNA constructs encoding the enzymes of the invention, to methods for preparing and purifying the enzymes, and to the use of the enzymes in various industrial processes, e.g. starch liquefaction or sweetener production.

In one aspect, the invention relates to hydrolyzing a soluble starch substrate using alpha amylase (AA) activity and a phytic acid hydrolyzing enzyme (FTU, or phytase), wherein the ratio of AAU:FTU is from about 1:15 to about 15:1, preferably from 1:10 to about 10:1. In an embodiment the ratio of AAU:FTU is from 1:4 to 3:1. In a further embodiment the ratio of AAU:FTU is 1:1. The phytase may be a wild-type enzyme from any source. The phytic acid hydrolyzing enzyme can be a bacterial or fungal phytase. The fungal phytase can be an *Aspergillus* phytase or a *Buttiauxella* phytase. In some embodiments, the bacterial phytase is from *Escherichia coli*. In one embodiment, the phytase may comprise the amino acid sequence of SEQ ID NO: 19.

A method for liquefying starch is provided, which comprises adding an amylase blend described above to a solution comprising starch, and liquefying the solution comprising starch. A preferred amylase blend for this application has an activity ratio of about 40% (as AAU/g DS) of the AmyS with the S242 substitution and about 60% (as LU/g DS) *B. licheniformis* alpha-amylase. Other ratios can be used for this application, such as 15:85, 20:80, 30:70, 50:50, 60:40, 70:30, 80:20 and 85:15.

The starch substrate may be obtained from corn, milo, rye, barley, wheat, sorghum, or oats. Other sources of starch include other grains, grasses, tubers and roots and more specifically rice, brans, cassava, millet, potato, sweet potato, and tapioca. The substrate may include plant material, such as granular starch from either a dry or wet milling process. The method may comprise a primary and/or secondary liquefaction step, including adding additional substrate to the slurry in the primary and/or secondary liquefaction step. The method may comprise using an amylase blend further comprising a phytic acid hydrolyzing enzyme.

A method for saccharifying the liquefied starch to obtain fermentable sugars also is provided. In some embodiments, the method further comprises fermenting the fermentable sugars under suitable fermentation conditions to obtain end-products such as alcohol. Alcohols produced by the present method include for example, ethanol and butanol.

In a further aspect, the invention relates to a starch conversion process and/or an ethanol fermentation process that does not require addition of an acid or base to adjust the pH. One embodiment relates to a pH adjustment-free liquefaction step, wherein the pH of the liquefaction is in the range of pH 4.5 to 5.4, and acid-neutralizing chemicals are not added to the liquefaction process step. In another embodiment, the pH of the liquefaction is in the range of pH 4.8 to 5.8, and acid neutralizing chemicals are not added to the liquefaction process step.

In one embodiment, the method comprises contacting a slurry of milled grain containing granular starch with both a phytic acid hydrolyzing enzyme and a blend of alpha amylases described above at a temperature 0-30° C. less than the starch gelatinization temperature, raising the temperature above the gelatinization temperature, hydrolyzing the gelatinized starch, and obtaining a fermentable substrate.

In another aspect, the invention relates to a process for producing a fermentable sugar comprising (a) mixing milled starch-containing material with water and thin stillage, wherein the thin stillage is in the range of 10 to 70% v/v, and obtaining a slurry comprising starch and having a dry solids (ds) content of 20 to 50% w/w, (b) treating the slurry with a phytase prior to or simultaneously with liquefying the starch, (c) liquefying the starch, (d) adding an alpha amylase blend described above to the starch either during step (b) and/or simultaneously with the liquefying step, and (e) saccharifying the liquefied starch to obtain fermentable sugars, wherein the pH is not adjusted during any of the steps (a), (b), (c), (d) or (e). In some embodiments, the fermentable sugar is recovered and purified or isomerized. In other embodiments, the phytase is added prior to the liquefaction step. In further embodiments, the alpha amylase blend is added with the phytase. In yet further embodiments, a second dose of the alpha amylase blend is added during the liquefaction step or added during the saccharification step.

In a further aspect, the invention relates to a process of producing alcohol from the starch-containing material, comprising liquefying and saccharifying a starch substrate as disclosed above to obtain fermentable sugars and further fermenting the fermentable sugars under suitable fermentation conditions to obtain alcohol. In some embodiments, the saccharification and fermentation steps are simultaneous. In some embodiments, the alcohol is ethanol or butanol.

In a further embodiment, the amylase blend described above can be used to convert a low viscosity liquefact to a sweetener, such as glucose, high fructose corn syrup, and the like. A preferred amylase blend for this application has an activity ratio of about 15% (as AAU/g DS) of the AmyS with the S242 substitution and about 85% (as LU/g DS) *B. licheniformis* alpha-amylase. Other ratios can be used for this application, such as 5:95, 10:90, and 20:80 and intermediate values thereof.

A method for producing a sweetener may comprise contacting a starch substrate with an amylase blend as described above, liquefying the starch substrate, and incubating the substrate at high temperature to produce a product comprising glucose. The incubating step can be a secondary liquefaction step. The incubating step may be conducted at a temperature of about 90-100° C., e.g., about 95° C. Incubating can be conducted for sufficient time for the product to comprise about 2-14 DE of glucose. In one embodiment, the product comprises about 10 DE of glucose. The method for producing a sweetener further may comprise saccharifying the product to produce a glucose-rich solution. The glucose-rich solution may comprise 80-99% glucose. In one embodiment, the glucose-rich solution comprises about 93-96% glucose. The saccharification may comprise contacting the glucose product with glucoamylase or an enzyme blend, such as OPTIMAX™ 4060-VHP, which comprises a glucoamylase and a pullulanase.

BRIEF DESCRIPTION OF THE DRAWINGS

FIG. 1A-1D show corresponding positions in other parent SPEZYME® Xtra-like alpha-amylases can be found by alignment. Note that SEQ ID NO: 4 is AmyS S242Q. AmyS S242A AmyS S242E are set forth in SEQ ID NOS: 3 and 5, respectively.

FIG. 4A-4I show pairwise alignments for SEQ ID NOS: 1 and 14.

FIG. 15 shows the amino acid sequence of SPEZYME® FRED depicted in SEQ ID NO: 20.

FIG. 16 shows the DE development from a starch substrate using a blend of AmyS S242Q (SEQ ID NO: 4) and SPEZYME® FRED.

DETAILED DESCRIPTION

Figure 2:
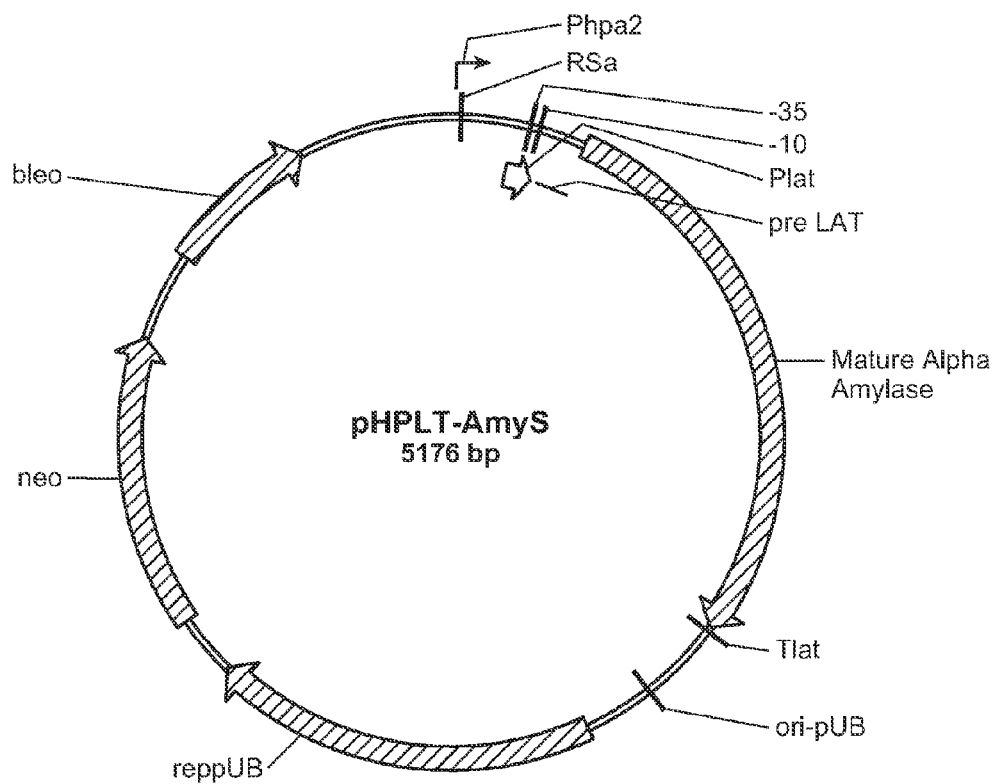
FIG. 2 shows the pHPLT-AmyS plasmid.

A blend of a variant of a parent *B. stearothermophilus* alpha-amylase and a thermostable alpha-amylase from *B. licheniformis* is provided. In a preferred embodiment, the alpha-amylase blend contains at least about 50% by activity as AAU/g DS of the *B. stearothermophilus* alpha-amylase variant enzyme. A preferred range is from about 10% to about 90% by activity as AAU/g DS of the *B. stearothermophilus* alpha-amylase variant enzyme. In a particularly preferred embodiment, an activity ratio of from about 10% to about 70% (as AAU/g DS) *B. stearothermophilus* alpha-amylase and from about 30% to about 90% (as LU/g DS) *B. licheniformis* alpha-amylase will be used so that the superior properties of each strain is exploited, that is, rapid viscosity reduction of starch liquefacts and thermostability, respectively.

The blend of a variant of a parent *B. stearothermophilus* alpha-amylase and a thermostable alpha-amylase from *B. licheniformis* will have other advantageous properties relating to processing of a starch liquefact, exemplified by DS levels, pH, calcium content, and liquefaction and cooking temperatures. For example, in certain embodiments DS levels can range from about 32% to about 40%, or higher. In another aspect, pH in a starch liquefact can range from about pH 5.5 to about pH 6.0. Calcium levels can range up to about 10 ppm calcium added. $T_{jet}$ can range from about 100° C. to about 110° C., while $T_{hold}$ can range from about 85° C. to about 95° C. These processes can include starch liquefaction to produce sweeteners such as glucose syrups, high fructose corn syrup, for example. Although these processes apply more particularly to production of sweeteners, in some embodiments the process can be applied to production of fermentation feedstocks The liquefacts thus produced as fermentation feedstocks can be used in fermentation processes, as discussed below in more detail, to produce useful end-products, including ethanol or butanol.

In some aspects, the present invention relies on routine techniques and methods used in the field of genetic engineering and molecular biology. The following resources include descriptions of general methodology useful in accordance with the invention: Sambrook et al., MOLECULAR CLONING: A LABORATORY MANUAL (2nd Ed., 1989); Kreigler, GENE TRANSFER AND EXPRESSION; A LABORA- TORY MANUAL (1990) and Ausubel et al., Eds. CURRENT PROTOCOLS IN MOLECULAR BIOLOGY (1994). These general references provide definitions and methods known to those in the art. However, it is not intended that the present invention be limited to any particular methods, protocols, and reagents described, as these may vary.

Unless defined otherwise herein, all technical and scientific terms used herein have the same meaning as commonly understood by one of ordinary skill in the art to which this invention belongs. Singleton, et al., DICTIONARY OF MICROBIOLOGY AND MOLECULAR BIOLOGY, 2D ED., John Wiley and Sons, New York (1994) and Hale & Markham, THE HARPER COLLINS DICTIONARY OF BIOLOGY, Harper Perennial, N.Y. (1991) provide one of skill with general dictionaries of many of the terms used in this invention.

Although any methods and materials similar or equivalent to those described herein can be used in the practice or testing of the present invention, the preferred methods and materials are described.

The invention will now be described in detail by way of reference only using the following definitions and examples. All patents and publications, including all sequences disclosed within such patents and publications, referred to herein are expressly incorporated by reference.

Numeric ranges are inclusive of the numbers defining the range.

Unless otherwise indicated, nucleic acids are written left to right in 5' to 3' orientation; amino acid sequences are written left to right in amino to carboxy orientation, respectively.

The headings provided herein are not limitations of the various aspects or embodiments of the invention which can be had by reference to the specification as a whole.

A. Definitions

As used herein the term "starch" refers to any material comprised of the complex polysaccharide carbohydrates of plants, comprised of amylose and amylopectin with the formula $(C_6H_{10}O_5)_x$, wherein X can be any number. In particular, the term refers to the amylase and/or amylopectin from any plant-based material including but not limited to grains, grasses, tubers and roots and more specifically wheat, barley, corn, rye, oats, sorgum, milo, rice, sorghum, brans, cassava, millet, potato, sweet potato, and tapioca.

The term "alpha-amylase (e.g., E.C. class 3.2.1.1)" refers to enzymes that catalyze the hydrolysis of alpha-1,4-glucosidic linkages. These enzymes have also been described as those effecting the exo or endohydrolysis of 1,4-α-D-glucosidic linkages in polysaccharides containing 1,4-α-linked D-glucose units. Another term used to describe these enzymes is "glycogenase". Exemplary enzymes include alpha-1,4-glucan 4-glucanohydrase glucanohydrolase.

The term "recombinant" when used in reference to a cell, nucleic acid, protein or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all.

The terms "protein" and "polypeptide" are used interchangeably herein. The conventional one-letter or three-letter code for amino acid residues is used herein.

A "signal sequence" means a sequence of amino acids bound to the N-terminal portion of a protein, which facilitates the secretion of the mature form of the protein outside the cell. The definition of a signal sequence is a functional one. The mature form of the extracellular protein lacks the signal sequence which is cleaved off during the secretion process.

A "gene" refers to a DNA segment that is involved in producing a polypeptide and includes regions preceding and following the coding regions as well as intervening sequences (introns) between individual coding segments (exons).

The term "nucleic acid" encompasses DNA, RNA, single stranded or double stranded and chemical modifications thereof. The terms "nucleic acid" and "polynucleotide" may be used interchangeably herein. Because the genetic code is degenerate, more than one codon may be used to encode a particular amino acid, and the present invention encompasses polynucleotides, which encode a particular amino acid sequence.

A "vector" refers to a polynucleotide sequence designed to introduce nucleic acids into one or more cell types. Vectors include cloning vectors, expression vectors, shuttle vectors, plasmids, phage particles, cassettes and the like.

An "expression vector" as used herein means a DNA construct comprising a DNA sequence which is operably linked to a suitable control sequence capable of effecting expression of the DNA in a suitable host. Such control sequences may include a promoter to effect transcription, an optional operator sequence to control transcription, a sequence encoding suitable ribosome binding sites on the mRNA, enhancers and sequences which control termination of transcription and translation.

A "promoter" is a regulatory sequence that is involved in binding RNA polymerase to initiate transcription of a gene. The promoter may be an inducible promoter or a constitutive promoter. A preferred promoter used in the invention is *Trichoderma reesei* cbh1, which is an inducible promoter.

"Under transcriptional control" is a term well understood in the art that indicates that transcription of a polynucleotide sequence, usually a DNA sequence, depends on its being operably linked to an element which contributes to the initiation of, or promotes transcription.

"Under translational control" is a term well understood in the art that indicates a regulatory process that occurs after mRNA has been formed.

As used herein when describing proteins and genes that encode them, the term for the gene is italicized, (e.g., the gene that encodes amyL (*B. licheniformis* AA) may be denoted as amyL). The term for the protein is generally not italicized and the first letter is generally capitalized, (e.g., the protein encoded by the amyL gene may be denoted as AmyL or amyL).

The term "derived" encompasses the terms "originated from", "obtained" or "obtainable from", and "isolated from".

The term "operably linked" refers to juxtaposition wherein the elements are in an arrangement allowing them to be functionally related. For example, a promoter is operably linked to a coding sequence if it controls the transcription of the sequence.

The term "selective marker" refers to a gene capable of expression in a host that allows for ease of selection of those hosts containing an introduced nucleic acid or vector. Examples of selectable markers include but are not limited to antimicrobials (e.g., hygromycin, bleomycin, or chloramphenicol) and/or genes that confer a metabolic advantage, such as a nutritional advantage on the host cell.

A polynucleotide or a polypeptide having a certain percent (e.g. 80%, 85%, 90%, 95%, or 99%) of sequence identity with another sequence means that, when aligned, that percentage of bases or amino acid residues are the same in comparing the two sequences. This alignment and the percent homology or identity can be determined using any suitable software program known in the art, for example those described in CURRENT PROTOCOLS IN MOLECULAR BIOLOGY (F. M. Ausubel et al. (eds) 1987, Supplement 30, section 7.7.18). Preferred programs include the Vector NTI Advance™ 9.0 (Invitrogen Corp. Carlsbad, Calif.), GCG Pileup, FASTA (Pearson et al. (1988) *Proc. Natl, Acad. Sci. USA* 85:2444-2448), and BLAST (BLAST Manual, Altschul et al., Natl Cent. Biotechnol. Inf., Natl Lib. Med. (NCIB NLM NIH), Bethesda, Md., and Altschul et al., (1997) *NAR* 25:3389-3402) programs. Another preferred alignment program is ALIGN Plus (Scientific and Educational Software, Pa.), preferably using default parameters. Another sequence software program that finds use is the TFASTA Data Searching Program available in the Sequence Software Package Version 6.0 (Genetics Computer Group, University of Wisconsin, Madison, Wis.).

One skilled in the art will recognize that sequences encompassed by the invention are also defined by the ability to hybridize under stringent hybridization conditions with the exemplified amyS sequence (e.g., SEQ ID NO:5 of WO 06/002643). A nucleic acid is hybridizable to another nucleic acid sequence when a single stranded form of the nucleic acid can anneal to the other nucleic acid under appropriate conditions of temperature and solution ionic strength. Hybridization and washing conditions are well known in the art (See, e.g., Sambrook (1989) supra, particularly chapters 9 and 11). In some embodiments, stringent conditions correspond to a Tm of 65° C. and 0.1×SSC, 0.1% SDS.

"Host strain" or "host cell" means a suitable host for an expression vector or DNA construct comprising a polynucleotide encoding a variant alpha-amylase enzyme according to the invention. Specifically, host strains are preferably bacterial cells. In a preferred embodiment of the invention, "host cell" means both the cells and protoplasts created from the cells of a microbial strain and particularly a *Bacillus* sp.

The term "culturing" refers to growing a population of microbial cells under suitable conditions in a liquid or solid medium. In one embodiment, culturing refers to fermentative bioconversion of a starch substrate containing granular starch to an end-product (typically in a vessel or reactor). Fermentation is the enzymatic and anaerobic breakdown of organic substances by microorganisms to produce simpler organic compounds. While fermentation occurs under anaerobic conditions it is not intended that the term be solely limited to strict anaerobic conditions, as fermentation also occurs in the presence of oxygen.

The term "contacting" refers to the placing of the respective enzyme(s) in sufficiently close proximity to the respective substrate to enable the enzyme(s) to convert the substrate to the end-product. Those skilled in the art will recognize that mixing solutions of the enzyme with the respective substrates can effect contacting.

The term "enzymatic conversion" in general refers to the modification of a substrate by enzyme action. The term as used herein also refers to the modification of a starch substrate by the action of an enzyme.

As used herein the term "saccharification" refers to enzymatic conversion of starch to glucose or other low molecular weight polysaccharides.

The term "gelatinization" means solubilization of a starch molecule by cooking to form a viscous suspension.

The term "liquefaction" refers to the stage in starch conversion in which gelatinized starch is hydrolyzed to give low molecular weight soluble dextrins.

The term "degree of polymerization (DP)" refers to the number (n) of anhydroglucopyranose units in a given saccharide. Examples of DP1 are the monosaccharides, such as glucose and fructose. Examples of DP2 are the disaccharides, such as maltose and sucrose. A DP>3 denotes polymers with a degree of polymerization of greater than 3.

The terms "end-product" or "desired end-product" refer to any carbon-source derived molecule product which is enzymatically converted from the starch substrate.

As used herein the term "enzyme unit" refers to the amount of enzyme that produces a given amount of product per given amount of time under assay conditions. In some embodiments, an enzyme unit refers to the amount of enzyme that produces 1 micromole of product per minute under the specified conditions of the assay. For example, in one embodiment, the term "glucoamylase activity unit" (GAU) is defined as the amount of enzyme required to produce 1 g of glucose per hour from soluble starch substrate (4% ds) under assay conditions of 60° C. and pH 4.2.

Alpha amylase activity (AAU) was determined by the rate of starch hydrolysis, as reflected in the rate of decrease of iodine-staining capacity measured spectrophotometrically. One AAU of bacterial alpha-amylase activity is the amount of enzyme required to hydrolyze 10 mg of starch per min under standardized conditions.

Alpha-amylase activity can also be determined as soluble starch unit (SSU) and is based on the degree of hydrolysis of soluble potato starch substrate (4% DS) by an aliquot of the enzyme sample at pH 4.5, 50° C. The reducing sugar content is measured using the DNS method as described in Miller, G. L. (1959) Anal. Chem. 31:426-428.

Alpha amylase activity in Liquefon Units (LU) was measured according to the method disclosed in U.S. Pat. No. 5,958,739. In brief, the assay method uses p-nitrophenyl maltoheptoside as a substrate with the non-reducing terminal sugar chemically blocked. The rate of p-nitrophenyl release is proportional to alpha amylase activity and release is monitored at 410 nm. Activity is calculated against a standard control.

As used herein the term "dry solids content (ds)" refers to the total solids of a slurry in % on a dry weight basis. The term "slurry" refers to an aqueous mixture containing insoluble solids.

The term "residual starch" refers to the remaining starch (soluble or insoluble) left in a composition after fermentation of a starch containing substrate.

As used herein "a recycling step" refers to the recycling of mash components, which may include residual starch, enzymes and/or microorganisms to ferment substrates comprising starch.

The term "mash" refers to a mixture of a fermentable carbon source (carbohydrate) in water used to produce a fermented product, such as an alcohol. In some embodiments, the term "beer" and "mash" are used interchangeability.

The term "stillage" means a mixture of non-fermented solids and water, which is the residue after removal of alcohol from a fermented mash.

The terms "distillers dried grain (DDG)" and "distillers dried grain with solubles (DDGS)" refer to a useful by-product of grain fermentation.

As used herein "ethanologenic microorganism" refers to a microorganism with the ability to convert a sugar or oligosaccharide to ethanol. The ethanologenic microorganisms are ethanologenic by virtue of their ability to express one or more enzymes that individually or together convert sugar to ethanol.

As used herein the term "ethanol producer" or ethanol producing microorganism" refers to any organism or cell that is capable of producing ethanol from a hexose or pentose.

Generally, ethanol-producing cells contain an alcohol dehydrogenase and a pyruvate decarboxylase. Examples of ethanol producing microorganisms include fungal microorganisms such as yeast. A preferred yeast includes strains of *Saccharomyces*, particularly, *S. cerevisiae*.

The term "heterologous" with reference to a polynucleotide or protein refers to a polynucleotide or protein that does not naturally occur in a host cell. In some embodiments, the protein is a commercially important industrial protein. It is intended that the term encompass proteins that are encoded by naturally occurring genes, mutated genes, and/or synthetic genes.

The term "endogenous" with reference to a polynucleotide or protein refers to a polynucleotide or protein that occurs naturally in the host cell.

The terms "recovered", "isolated", and "separated" as used herein refer to a compound, protein, cell, nucleic acid or amino acid that is removed from at least one component with which it is naturally associated.

As used herein, the terms "transformed", "stably transformed" and "transgenic" used in reference to a cell means the cell has a non-native (e.g., heterologous) nucleic acid sequence integrated into its genome or as an episomal plasmid that is maintained through multiple generations.

As used herein, the term "expression" refers to the process by which a polypeptide is produced based on the nucleic acid sequence of a gene. The process includes both transcription and translation.

The term "introduced" in the context of inserting a nucleic acid sequence into a cell, means "transfection", or "transformation" or "transduction" and includes reference to the incorporation of a nucleic acid sequence into a eukaryotic or prokaryotic cell wherein the nucleic acid sequence may be incorporated into the genome of the cell (e.g., chromosome, plasmid, plastid, or mitochondrial DNA), converted into an autonomous replicon, or transiently expressed (e.g., transfected mRNA).

As used herein the term "specific activity" means an enzyme unit defined as the number of moles of substrate converted to product by an enzyme preparation per unit time under specific conditions. Specific activity is expressed as units (U)/mg of protein.

The term "yield" refers to the amount of end-product or desired end-products produced using the methods of the present invention. In some preferred embodiments, the yield is greater than that produced using methods known in the art. In some embodiments, the term refers to the volume of the end product and in other embodiment the term refers to the concentration of the end product.

"ATCC" refers to American Type Culture Collection located at Manassas, Va. 20108 (ATCC).

"NRRL" refers to the Agricultural Research Service Culture Collection, National Center for Agricultural Utilization Research (and previously known as USDA Northern Regional Research Laboratory), Peoria, Ill.

"A", "an" and "the" include plural references unless the context clearly dictates otherwise.

As used herein the term "comprising" and its cognates are used in their inclusive sense; that is, equivalent to the term "including" and its corresponding cognates.

Nomenclature

In the present description and claims, the conventional one-letter and three-letter codes for amino acid residues are used. For ease of reference, alpha-amylase variants of the invention are described by use of the following nomenclature:

Original amino acid(s): position(s): substituted amino acid(s)

According to this nomenclature, for instance the substitution of serine by an alanine in position 242 is shown as:
Ser242Ala or S242A
a deletion of alanine in position 30 is shown as:
Ala30* or A30* or ΔA30
and insertion of an additional amino acid residue, such as lysine, is shown as:
Ala30AlaLys or A30AK A deletion of a consecutive stretch of amino acid residues, such as amino acid residues 30-33, is indicated as (30-33)* or Δ(A30-N33).

Where a specific alpha-amylase contains a "deletion" in comparison with other alpha-amylases and an insertion is made in such a position this is indicated as:
*36Asp or *36D
for insertion of an aspartic acid in position 36.

Multiple mutations are separated by plus signs, i.e.:
Ala30Asp+Glu34Ser or A30N+E34S
representing mutations in positions 30 and 34 substituting alanine and glutamic acid for asparagine and serine, respectively.

When one or more alternative amino acid residues may be inserted in a given position it is indicated as
A30N,E or
A30N or A30E Furthermore, when a position suitable for modification is identified herein without any specific modification being suggested, it is to be understood that any amino acid residue may be substituted for the amino acid residue present in the position. Thus, for instance, when a modification of an alanine in position 30 is mentioned, but not specified, it is to be understood that the alanine may be deleted or substituted for any other amino acid, i.e., any one of:
R, N, D, A, C, Q, E, G, H, I, L, K, M, F, P, S, T, W, Y, V.

Further, "A30X" means any one of the following substitutions:
A30R, A30N, A30D, A30C, A30Q, A30E, A30G, A30H, A30I, A30L, A30K, A30M, A30F, A30P, A30S, A30T, A30W, A30Y, or A30 V;
or in short: A30R,N,D,C,Q,E,G,H,I,L,K,M,F,P,S,T,W,Y,V.

If the parent enzyme—used for the numbering—already has the amino acid residue in question suggested for substitution in that position the following nomenclature is used:
"X30N" or "X30N,V" in the case where for instance one or N or V is present in the wildtype.

Thus, it means that other corresponding parent enzymes are substituted to an "Asn" or "Val" in position 30.

Characteristics of Amino Acid Residues
Charged Amino Acids:
Asp, Glu, Arg, Lys, His
Negatively charged amino acids (with the most negative residue first):
Asp, Glu
Positively charged amino acids (with the most positive residue first):
Arg, Lys, His
Neutral Amino Acids:
Gly, Ala, Val, Leu, Ile, Phe, Tyr, Trp, Met, Cys, Asn, Gln, Ser, Thr, Pro
Hydrophobic amino acid residues (with the most hydrophobic residue listed last):
Gly, Ala, Val, Pro, Met, Leu, Ile, Tyr, Phe, Trp,
Hydrophilic amino acids (with the most hydrophilic residue listed last):
Thr, Ser, Cys, Gln, Asn Alpha-Amylases The amylase blends comprise an AmyS alpha amylase and a *B. licheniformis* alpha amylase. The AmyS enzyme may comprise the polypeptide sequence of SEQ ID NO: 1 or SEQ ID NO: 2, wherein the S242 residue is substituted. In a preferred embodiment, the AmyS comprises an amino acid sequence set forth in SEQ ID NO: 4, also known as "AmyS S242Q" or S242Q," which has a S242Q substitution compared to SPEZYME® Xtra (SEQ ID NO: 2). In another embodiment, the AmyS may be selected from one of the AmyS enzymes comprising the polypeptide sequence of SEQ ID NOS: 6, 7, 8, 9, 10, 11, 12, 15 and 16, wherein the S242 residue is substituted.

The S242 substitution may be an S242A, S242E, S242Q, S242F, S242H, or S242N substitution. In one embodiment, the amino acid substitution at position S242 alters the thermostability of the AmyS. The AmyS with the substitution at position S242 may have a higher thermostability between about 80° C. and about 95° C. compared to an AmyS without the S242 substitution.

In one embodiment, the AmyS comprises an amino acid sequence having at least 60%, 70%, 80%, 85%, 90%, 95%, 96%, 97%, 98%, or 99% sequence identity to the AmyS of SEQ ID NO: 1, wherein the AmyS has alpha-amylase activity. The AmyS may comprise a substitution of a cysteine at amino acids 349 and 428, using SEQ ID NO: 1 for numbering. The AmyS also may comprise a substitution of N193 and/or V416. The AmyS also may comprise a deletion of amino acids 179 and 180, using SEQ ID NO: 1 for numbering.

The AmyS enzymes may have an altered amino acid sequence compared to a wild-type AmyS that alters one or more properties of the enzyme, e.g., substrate specificity, substrate binding, substrate cleavage pattern, thermal stability, pH/activity profile, pH/stability profile, stability towards oxidation, $Ca^{2+}$ dependency, and/or specific activity. For instance, the alteration may result in an enzyme that has a reduced $Ca^{2+}$ dependency and/or an altered pH/activity profile and/or thermostability, compared to a wild-type AmyS.

A number of alpha-amylases produced by *Bacillus* spp. are highly homologous (identical) on the amino acid level.

The identity of a number of known *Bacillus* alpha-amylases can be found in the below Table 1:

TABLE 1

| | Percent identity | | | | | | | |
|---|---|---|---|---|---|---|---|---|
| | 707 | AP1378 | BAN | BSG | SP690 | SP722 | AA560 | LAT |
| 707 | 100.0 | 86.4 | 66.9 | 66.5 | 87.6 | 86.2 | 95.5 | 68.1 |
| AP1378 | 86.4 | 100.0 | 67.1 | 68.1 | 95.1 | 86.6 | 86.0 | 69.4 |
| BAN | 66.9 | 67.1 | 100.0 | 65.6 | 67.1 | 68.8 | 66.9 | 80.7 |
| BSG | 66.5 | 68.1 | 65.6 | 100.0 | 67.9 | 67.1 | 66.3 | 65.4 |
| SP690 | 87.6 | 95.1 | 67.1 | 67.9 | 100.0 | 87.2 | 87.0 | 69.2 |
| SP722 | 86.2 | 86.6 | 68.8 | 67.1 | 87.2 | 100.0 | 86.8 | 70.8 |
| AA560 | 95.5 | 86.0 | 66.9 | 66.3 | 87.0 | 86.8 | 100.0 | 68.3 |
| LAT | 68.1 | 69.4 | 80.7 | 65.4 | 69.2 | 70.8 | 68.3 | 100.0 |

For instance, the *B. lichenformis* alpha-amylase (LAT) comprising the amino acid sequence shown in SEQ ID NO: 7 has been found to be about 81% homologous with the *B. amyloliquefaciens* alpha-amylase comprising the amino acid sequence shown in SEQ ID NO: 9 and about 65% homologous with the *G. stearothermophilus* alpha-amylase (BSG) comprising the amino acid sequence shown in SEQ ID NO: 1. Further homologous alpha-amylases include SP690 and SP722 disclosed in WO 95/26397 and the #707 alpha-amylase derived from *Bacillus* sp., shown in SEQ ID NO: 6 and described by Tsukamoto et al., Biochemical and Biophysical Research Communications, 151 (1988), pp. 25-31.

The KSM AP1378 alpha-amylase is disclosed in WO 97/00324 (from KAO Corporation).

Still further homologous alpha-amylases include the alpha-amylase produced by the *B. lichenformis* strain described in EP 0252666. (ATCC 27811), and the alpha-amylases identified in WO 91/00353 and WO 94/18314. Other commercial SPEZYME® Xtra-like alpha-amylases are comprised in the products sold under the following tradenames: SPEZYME®® AA and Ultraphlow (available from Danisco US Inc, Genencor Division), and Keistase™ (available from Daiwa) and Liquezyme SC (available from Novozymes, Denmark).

Because of the substantial homology found between these alpha-amylases, they are considered to belong to the same class of alpha-amylases, namely the class of "SPEZYME® Xtra-like alpha-amylases".

Accordingly, in the present context, the term "SPEZYME® Xtra-like alpha-amylase" is intended to indicate an alpha-amylase, in particular *Bacillus* alpha-amylase, especially *Geobacillus stearothermophilus* alpha-amylase, which, at the amino acid level, exhibits a substantial identity to the alpha-amylase having the amino acid sequence shown in SEQ ID NO: 2, herein. SPEZYME® Xtra (SEQ ID NO: 2) is commercially available from Danisco US Inc, Genencor Division. *Geobacillus stearothermophilus* has been referred to as *Bacillus stearothermophilus* in the literature and the two may be used interchangeably herein.

In other words, all the following alpha-amylases, which have the amino acid sequences shown in SEQ ID NOS: 1, 6, 7, 8, 9, 10, 11, 12, 15 and 16 herein are considered to be a "SPEZYME® Xtra-like alpha-amylase". Other SPEZYME® Xtra-like alpha-amylases are alpha-amylases i) which displays at least 60%, such as at least 70%, e.g., at least 75%, or at least 80%, at least 85%, at least 90%, at least 95%, at least 96%, at least 97%, at least 98%, at least 99% homology (identity) with at least one of said amino acid sequences shown in SEQ ID NOS: 1, 6, 7, 8, 9, 10, 11, 12, 15 and 16, and/or is encoded by a DNA sequence which hybridizes to the DNA sequences encoding the above-specified alpha-amylases which are apparent from SEQ ID NOS: 9 (BAN), 5 (BSG), 3 (SP722), 1 (SP690), 7 (LAT), 11 (AA560) of WO 06/002643 and of the present specification (which encoding sequences encode the amino acid sequences shown in SEQ ID NOS: 1, 6, 7, 8, 9, 10, 11, 12, 15 and 16 herein, respectively).

Another useful alpha-amylase amylase from *Bacillus licheniformis* is SPEZYME® FRED (SEQ ID NO: 20), commercially available from Danisco US Inc, Genencor Division. This alpha-amylase may be referred to herein as SPEZYME® FRED or "Fred" (SEQ ID NO: 20).

Homology (Identity)

The homology may be determined as the degree of identity between the two sequences indicating a derivation of the first sequence from the second. The homology nay suitably be determined by means of computer programs known in the art such as GAP provided in the GCG program package (described above). Thus, Gap GCG v8 may be used with the default scoring matrix for identity and the following default parameters: GAP creation penalty of 5.0 and GAP extension penalty of 0.3, respectively for nucleic acidic sequence comparison, and GAP creation penalty of 3.0 and GAP extension penalty of 0.1, respectively, for protein sequence comparison. GAP uses the method of Needleman and Wunsch, (1970), J. Mol. Biol. 48:443-453, to make alignments and to calculate the identity.

A structural alignment between SPEZYME® Xtra (SEQ ID NO: 2) and, e.g., another alpha-amylase may be used to identify equivalent/corresponding positions in other SPEZYME® Xtra-like alpha-amylases. One method of obtaining said structural alignment is to use the Pile Up programme from the GCG package using default values of gap penalties, i.e., a gap creation penalty of 3.0 and gap extension penalty of 0.1. Other structural alignment methods include the hydrophobic cluster analysis (Gaboriaud et al., (1987), FEB S LETTERS 224, pp. 149-155) and reverse threading (Huber, T; Torda, A E, PROTEIN SCIENCE Vol. 7, No. 1 pp. 142-149 (1998).

Hybridization

The oligonucleotide probe used in the characterization of the SPEZYME® Xtra-like alpha-amylase above may suitably be prepared on the basis of the full or partial nucleotide or amino acid sequence of the alpha-amylase in question.

Suitable conditions for testing hybridization involve presoaking in 5×SSC and prehybridizing for 1 hour at 40° C. in a solution of 20% formamide, 5×Denhardt's solution, 50 mM sodium phosphate, pH 6.8, and 50 mg of denatured sonicated calf thymus DNA, followed by hybridization in the same solution supplemented with 100 mM ATP for 18 hours at 40° C., followed by three times washing of the filter in 2×SSC, 0.2% SDS at 40° C. for 30 minutes (low stringency), preferred at 50° C. (medium stringency), more preferably at 65° C. (high stringency), even more preferably at 75° C. (very high stringency). More details about the hybridization method can be found in Sambrook et al., Molecular Cloning: A Laboratory Manual, 2nd Ed., Cold Spring Harbor, 1989.

In the present context, "derived from" is intended not only to indicate an alpha-amylase produced or producible by a strain of the organism in question, but also an alpha-amylase encoded by a DNA sequence isolated from such strain and produced in a host organism transformed with said DNA sequence. Finally, the term is intended to indicate an alpha-amylase, which is encoded by a DNA sequence of synthetic and/or cDNA origin and which has the identifying characteristics of the alpha-amylase in question. The term is also intended to indicate that the parent alpha-amylase may be a variant of a naturally occurring alpha-amylase, i.e., a variant, which is the result of a modification (insertion, substitution, deletion) of one or more amino acid residues of the naturally occurring alpha-amylase.

Altered Properties

The following section describes the relationship between mutations, which are present in a variant described herein, and desirable alterations in properties (relative to those of a parent SPEZYME® Xtra-like alpha-amylase), which may result therefrom.

As mentioned above the invention relates to a SPEZYME® Xtra-like alpha-amylase with altered properties.

Parent SPEZYME® Xtra-like alpha-amylases specifically contemplated in connection with going through the specifically contemplated altered properties are the above mentioned parent SPEZYME® Xtra-like alpha-amylase and parent hybrid SPEZYME® Xtra-like alpha-amylases.

The *Geobacillus stearothermophilus* alpha-amylase (SEQ ID NO: 2) is used as the starting point, but corresponding positions in, e.g., the SP722, BLA, BAN, AA560, SP690, KSM AP1378, #707 and other *Bacillus* alpha-amylases should be understood as disclosed and specifically contemplated too.

In an aspect the invention relates to variant with altered properties as mentioned above.

In the first aspect a variant of a parent *G. stearothermophilus* alpha-amylase, comprising an alteration at one or more positions (using SEQ ID NO: 1 for the amino acid numbering) selected from the group of:

P17, D19, T21, N28, S51, G72, V74, A82, Q86, Q89, A93, G95, Q97, W115, D117, P123, S124, D125, N127, I130, G132, Q135, P145, G146, G148, S153, Y159, W166, S169, K171, W187, P209, N224, S242, G256, D269, N271, T278, N281, G302, A304, R308, T321, Q358, P378, S382, K383, T398, H405, T417, E418, P420, G421, P432, W437, G446, G454, S457, T459, T461, S464, G474, R483.

wherein (a) the alteration(s) are independently
  (i) an insertion of an amino acid downstream of the amino acid which occupies the position,
  (ii) a deletion of the amino acid which occupies the position, or
  (iii) a substitution of the amino acid which occupies the position with a different amino acid,
(b) the variant has alpha-amylase activity and (c) each position corresponds to a position of the amino add sequence of the parent *G. stearothermophilus* alpha-amylase having the amino acid sequence shown in SEQ ID NO: 2.

Specifically contemplated herein are S242A, S242Q, S242N and S242E.

Additionally, residues R179, G180, I181, G182, K183 were chosen to explore the effect of mutations in the calcium-sodium binding region, and P245 was chosen because a proline in the middle of an alpha-helix is unusual.

Corresponding positions in other parent SPEZYME® Xtra-like alpha-amylases can be found by alignment as described above and shown in the alignment in FIG. 4. Thus, in a second aspect a variant of a parent SPEZYME® Xtra-like alpha-amylase, comprising an alteration at one or more of the above enumerated positions (using SEQ ID NO: 1 for the amino acid numbering) is contemplated herein.

Stability

In the context of the variants described herein, mutations (including amino acid substitutions and deletion) of importance with respect to achieving altered stability, in particular improved stability (i.e., higher or lower), at especially high temperatures (i.e., 70-120° C.) and/or extreme pH (i.e. low or high pH, i.e., pH 4-6 or pH 8-11, respectively), in particular at free (i.e., unbound, therefore in solution) calcium concentrations below 60 ppm, include any of the mutations listed in the "Altered Properties" section. The stability may be determined as described in the "Methods" section below.

$Ca^{2+}$ Stability

Altered $Ca^{2+}$ stability means the stability of the enzyme under $Ca^{2+}$ depletion has been improved, i.e., higher or lower stability. In the context of the presently described variants, mutations (including amino acid substitutions and deletions) of importance with respect to achieving altered $Ca^{2+}$ stability, in particular improved $Ca^{2+}$ stability, i.e., higher or lower stability, at especially high pH (i.e., pH 8-10.5) include any of the mutations listed in the in "Altered Properties" section.

Specific Activity

In a further aspect, important mutations (including amino acid substitutions and deletions) with respect to obtaining variants exhibiting altered specific activity, in particular increased or decreased specific activity, especially at temperatures from 10-60° C., preferably 20-50° C., especially 30-40° C., include any of the mutations listed in the in "Altered properties" section. The specific activity may be determined as described in the "Methods" section below.

Oxidation Stability

The described variants may have altered oxidation stability, in particular higher oxidation stability, in comparison to the parent alpha-amylase. Increased oxidation stability is advantageous in, e.g., detergent compositions and decreased oxidation stability may be advantageous in composition for starch liquefaction. Oxidation stability may be determined as described in the "Methods" section below.

Altered pH Profile

Important positions and mutations with respect to obtaining variants with altered pH profile, in particular improved activity at especially high pH (i.e., pH 8-10.5) or low pH (i.e., pH 4-6) include mutations of amino residues located close to the active site residues.

Preferred specific mutations/substitutions are the ones listed above in the section "Altered Properties" for the positions in question. Suitable assays are described in the "Methods" section below.

Wash Performance

Important positions and mutations with respect to obtaining variants with improved wash performance at especially high pH (i.e., pH 8.5-11) include the specific mutations/substitutions listed above in the section "Altered Properties" for the positions in question. The wash performance may be tested as described below in the "Methods" section.

General Mutations in Variants of the Invention

A variant described herein may in one embodiment comprise one or more modifications in addition to those outlined above. Thus, it may be advantageous that one or more Proline (Pro) residues present in the part of the alpha-amylase variant which is modified is/are replaced with a non-Proline residue which may be any of the possible, naturally occurring non-Proline residues, and which preferably is an Alanine, Glycine, Serine, Threonine, Valine or Leucine.

Analogously, in one embodiment one or more Cysteine residues present in the parent alpha-amylase may be replaced with a non-Cysteine residue such as Serine, Alanine, Threonine, Glycine, Valine or Leucine.

It is to be understood that the present invention encompasses variants incorporating two or more of the above outlined modifications.

Furthermore, it may be advantageous to introduce mutations in one or more of the following positions (using SEQ ID NO: 7 for the numbering):

M15, V128, A111, H133, W138, T149, M197, N188, A209, A210, H405, T412, in particular the following single, double or triple or multi mutations:

M15X, in particular M15T,L;
V128X, in particular V128E;
H133X, in particular H133Y;
N188X, in particular N188S,T,P;
M197X, in particular M197T,L;
A209X, in particular A209V;
M197T/W138F; M197T/138Y; M15T/H133Y/N188S;
M15N128E/H133Y/N188S; E119C/S130C; D124C/R127c; H133Y/T149I; G475R, H133Y/S187D; H133Y/A209V.

In the case of the parent alpha-amylase having the amino acid sequence shown in SEQ ID NO. 7, relevant amino acid residues which may be deleted or substituted with a view to improving the oxidation stability include the single cysteine residue (C363) and the methionine residues located in positions M8, M9, M96, M200, M206, M284, M307, M311, M316 and M438 in SEQ ID NO. 2.

With respect to increasing the thermal stability of an alpha-amylase variant relative to its parent alpha-amylase, it appears to be particularly desirable to delete at least one, and preferably two or even three, of the following amino acid residues in the amino acid sequence shown in SEQ ID NO. 2 are F178, R179, G180, I181, G182 and K183.

Particularly interesting pairwise deletions of this type are R179*+G180*; and I181*+G182* (SEQ ID NOs. 16 or 15, respectively) (or equivalents of these pairwise deletions in another alpha-amylase meeting the requirements of a parent alpha-amylase in the context of the present disclosure).

Other residues of interest include N193F and V416G in the amino acid sequence shown in SEQ ID No. 2.

Methods of Preparing α-Amylase Variants

Several methods for introducing mutations into genes are known in the art. After a brief discussion of the cloning of α-amylase-encoding DNA sequences, methods for generating mutations at specific sites within the α-amylase-encoding sequence will be discussed.

Cloning a DNA Sequence Encoding an α-Amylase

The DNA sequence encoding a parent α-amylase may be isolated from any cell or microorganism producing the α-amylase in question, using various methods well known in the art. First, a genomic DNA and/or cDNA library should be constructed using chromosomal DNA or messenger RNA from the organism that produces the α-amylase to be studied. Then, if the amino acid sequence of the α-amylase is known, homologous, labelled oligonucleotide probes may be synthesized and used to identify α-amylase-encoding clones from a genomic library prepared from the organism in question. Alternatively, a labelled oligonucleotide probe containing sequences homologous to a known α-amylase gene could be used as a probe to identify α-amylase-encoding clones, using hybridization and washing conditions of lower stringency.

Yet another method for identifying α-amylase-encoding clones would involve inserting fragments of genomic DNA into an expression vector, such as a plasmid, transforming α-amylase-negative bacteria with the resulting genomic DNA library, and then plating the transformed bacteria onto agar containing a substrate for α-amylase, thereby allowing clones expressing the α-amylase to be identified.

Alternatively, the DNA sequence encoding the enzyme may be prepared synthetically by established standard methods, e.g. the phosphoamidite method described by S. L. Beaucage and M. H. Caruthers (1981) or the method described by Matthes et al. (1984). In the phosphoamidite method, oligonucleotides are synthesized, e.g. in an automatic DNA synthesizer, purified, annealed, ligated and cloned in appropriate vectors.

Finally, the DNA sequence may be of mixed genomic and synthetic origin, mixed synthetic and cDNA origin or mixed genomic and cDNA origin, prepared by ligating fragments of synthetic, genomic or cDNA origin (as appropriate, the fragments corresponding to various parts of the entire DNA sequence), in accordance with standard techniques. The DNA sequence may also be prepared by polymerase chain reaction (PCR) using specific primers, for instance as described in U.S. Pat. No. 4,683,202 or R. K. Saiki et al. (1988).

Site-Directed Mutagenesis

Once an α-amylase-encoding DNA sequence has been isolated, and desirable sites for mutation identified, mutations may be introduced using synthetic oligonucleotides. These oligonucleotides contain nucleotide sequences flanking the desired mutation sites; mutant nucleotides are inserted during oligonucleotide synthesis. In a specific method, a single-stranded gap of DNA, bridging the α-amylase-encoding sequence, is created in a vector carrying the α-amylase gene. Then the synthetic nucleotide, bearing the desired mutation, is annealed to a homologous portion of the single-stranded DNA. The remaining gap is then filled in with DNA polymerase I (Klenow fragment) and the construct is ligated using T4 ligase. A specific example of this method is described in Morinaga et al. (1984). U.S. Pat. No. 4,760,025 discloses the introduction of oligonucleotides encoding multiple mutations by performing minor alterations of the cassette. However, an even greater variety of mutations can be introduced at any one time by the Morinaga method, because a multitude of oligonucleotides, of various lengths, can be introduced.

Another method of introducing mutations into α-amylase-encoding DNA sequences is described in Nelson and Long (1989). It involves the 3-step generation of a PCR fragment containing the desired mutation introduced by using a chemically synthesized DNA strand as one of the primers in the PCR reactions. From the PCR-generated fragment, a DNA fragment carrying the mutation may be isolated by cleavage with restriction endonucleases and reinserted into an expression plasmid.

Alternative methods for providing variants of the invention include gene shuffling, e.g., as described in WO 95/22625 (from Affymax Technologies N.V.) or in WO 96/00343 (from Novo Nordisk A/S), or other corresponding techniques resulting in a hybrid enzyme comprising the mutation(s), e.g., substitution(s) and/or deletion(s), in question.

Expression of Alpha-Amylase Variants

According to the invention, a DNA sequence encoding the variant produced by methods described above, or by any alternative methods known in the art, can be expressed, in enzyme form, using an expression vector which typically includes control sequences encoding a promoter, operator, ribosome binding site, translation initiation signal, and, optionally, a repressor gene or various activator genes.

The recombinant expression vector carrying the DNA sequence encoding an alpha-amylase variant of the invention may be any vector, which may conveniently be subjected to recombinant DNA procedures, and the choice of vector will often depend on the host cell into which it is to be introduced. Thus, the vector may be an autonomously replicating vector, i.e., a vector which exists as an extrachromosomal entity, the replication of which is independent of chromosomal replication, e.g., a plasmid, a bacteriophage or an extrachromosomal element, minichromosome or an artificial chromosome. Alternatively, the vector may be one which, when introduced into a host cell, is integrated into the host cell genome and replicated together with the chromosome(s) into which it has been integrated.

In the vector, the DNA sequence should be operably connected to a suitable promoter sequence. The promoter may be any DNA sequence, which shows transcriptional activity in the host cell of choice and may be derived from genes encoding proteins either homologous or heterologous to the host cell. Examples of suitable promoters for directing the transcription of the DNA sequence encoding an alpha-amylase variant of the invention, especially in a bacterial host, are the promoter of the lac operon of *E. coli*, the *Streptomyces coelicolor* agarase gene dagA promoters, the promoters of the *Bacillus licheniformis* alpha-amylase gene (amyL), the promoters of the *Geobacillus stearothermophilus* maltogenic amylase gene (amyM), the promoters of the *Bacillus amyloliquefaciens* alpha-amylase (amyQ), the promoters of the *Bacillus subtilis* xylA and xylB genes etc. For transcription in a fungal host, examples of useful promoters are those derived from the gene encoding *A. oryzae* TAKA amylase, *Rhizomucor miehei* aspartic proteinase, *A. niger* neutral alpha-amylase, *A. niger* acid stable alpha-amylase, *A. niger* glucoamylase, *Rhizomucor miehei* lipase, *A. oryzae* alkaline protease, *A. oryzae* triose phosphate isomerase or *A. nidulans* acetamidase.

The expression vector of the invention may also comprise a suitable transcription terminator and, in eukaryotes, polyadenylation sequences operably connected to the DNA sequence encoding the alpha-amylase variant of the invention. Termination and polyadenylation sequences may suitably be derived from the same sources as the promoter.

The vector may further comprise a DNA sequence enabling the vector to replicate in the host cell in question. Examples of such sequences are the origins of replication of plasmids pUC19, pACYC177, pUB110, pE194, pAMB1 and pIJ702.

The vector may also comprise a selectable marker, e.g. a gene the product of which complements a defect in the host cell, such as the dal genes from *B. subtilis* or *B. licheniformis*, or one which confers antibiotic resistance such as ampicillin, kanamycin, chloramphenicol or tetracycline resistance. Furthermore, the vector may comprise *Aspergillus* selection markers such as amdS, argB, niaD and sC, a marker giving rise to hygromycin resistance, or the selection may be accomplished by co-transformation, e.g., as described in WO 91/17243.

While intracellular expression may be advantageous in some respects, e.g., when using certain bacteria as host cells, it is generally preferred that the expression is extracellular. In general, the *Bacillus* alpha-amylases mentioned herein comprise a preregion permitting secretion of the expressed protease into the culture medium. If desirable, this preregion may be replaced by a different preregion or signal sequence, conveniently accomplished by substitution of the DNA sequences encoding the respective preregions.

The procedures used to ligate the DNA construct of the invention encoding an alpha-amylase variant, the promoter, terminator and other elements, respectively, and to insert them into suitable vectors containing the information necessary for replication, are well known to persons skilled in the art (cf., for instance, Sambrook et al., Molecular Cloning: A Laboratory Manual, 2nd Ed., Cold Spring Harbor, 1989).

The cell of the invention, either comprising a DNA construct or an expression vector of the invention as defined above, is advantageously used as a host cell in the recombinant production of an alpha-amylase variant of the invention. The cell may be transformed with the DNA construct of the invention encoding the variant, conveniently by integrating the DNA construct (in one or more copies) in the host chromosome. This integration is generally considered to be an advantage as the DNA sequence is more likely to be stably maintained in the cell. Integration of the DNA constructs into the host chromosome may be performed according to conventional methods, e.g., by homologous or heterologous recombination. Alternatively, the cell may be transformed with an expression vector as described above in connection with the different types of host cells.

The cell of the invention may be a cell of a higher organism such as a mammal or an insect, but is preferably a microbial cell, e.g., a bacterial or a fungal (including yeast) cell.

Examples of suitable bacteria are Gram-positive bacteria such as *Bacillus subtilis, Bacillus licheniformis, Bacillus lentus, Bacillus brevis, Geobacillus stearothermophilus, Bacillus alkalophilus, Bacillus amyloliquefaciens, Bacillus coagulans, Bacillus circulans, Bacillus lautus, Bacillus megaterium, Bacillus thuringiensis*, or *Streptomyces lividans* or *Streptomyces murinus*, or gram-negative bacteria such as *E. coli*. The transformation of the bacteria may, for instance, be effected by protoplast transformation or by using competent cells in a manner known per se.

The yeast organism may favorably be selected from a species of *Saccharomyces* or *Schizosaccharomyces*, e.g. *Saccha-* romyces cerevisiae. The filamentous fungus may advantageously belong to a species of Aspergillus, e.g., Aspergillus oryzae or Aspergillus niger. Fungal cells may be transformed by a process involving protoplast formation and transformation of the protoplasts followed by regeneration of the cell wall in a manner known per se. A suitable procedure for transformation of Aspergillus host cells is described in EP 238 023.

In a yet further aspect, the present invention relates to a method of producing an alpha-amylase variant of the invention, which method comprises cultivating a host cell as described above under conditions conducive to the production of the variant and recovering the variant from the cells and/or culture medium.

The medium used to cultivate the cells may be any conventional medium suitable for growing the host cell in question and obtaining expression of the alpha-amylase variant of the invention. Suitable media are available from commercial suppliers or may be prepared according to published recipes (e.g., as described in catalogues of the American Type Culture Collection).

The alpha-amylase variant secreted from the host cells may conveniently be recovered from the culture medium by well-known procedures, including separating the cells from the medium by centrifugation or filtration, and precipitating proteinaceous components of the medium by means of a salt such as ammonium sulfate, followed by the use of chromatographic procedures such as ion exchange chromatography, affinity chromatography, or the like.

Phytases

Phytases useful for the invention include enzymes capable of hydrolyzing phytic acid under the defined conditions of the incubation and liquefaction steps. In some embodiments, the phytase is capable of liberating at least one inorganic phosphate from an inositol hexaphosphate (phytic acid). Phytases can be grouped according to their preference for a specific position of the phosphate ester group on the phytate molecule at which hydrolysis is initiated, (e.g., as 3-phytases (EC 3.1.3.8) or as 6-phytases (EC 3.1.3.26)). A typical example of phytase is myo-inositol-hexakiphosphate-3-phosphohydrolase.

Phytases can be obtained from microorganisms such as fungal and bacterial organisms. Some of these microorganisms include e.g. Aspergillus (e.g., A. niger, A. terreus, A. ficum and A. fumigatus), Myceliophthora (M. thermophila), Talaromyces (T. thermophilus) Trichoderma spp (T. reesei). and Thermomyces (WO 99/49740). Also phytases are available from Penicillium species, e.g., P. hordei (ATCC No. 22053), P. piceum (ATCC No. 10519), or P. brevi-compactum (ATCC No. 48944). See, for example U.S. Pat. No. 6,475, 762. In addition, phytases are available from Bacillus (e.g. B. subtilis, Pseudomonas, Peniophora, E. coli, Citrobacter, Enterbacter and Buttiauxella (see WO2006/043178).

Commercial phytases are available such as NATUPHOS (BASF), RONOZYME P (Novozymes A/S), PHZYME (Danisco A/S, Diversa) and FINASE (AB Enzymes). The method for determining microbial phytase activity and the definition of a phytase unit has been published by Engelen et al. (1994) J. of AOAC International, 77: 760-764. The phytase may be a wild-type phytase, a variant or fragment thereof.

In one embodiment, the phytase useful in the present invention is one derived from the bacterium Buttiauxiella spp. The Buttiauxiella spp. includes B. agrestis, B. brennerae, B. ferragutiase, B. gaviniae, B. izardii, B. noackiae, and B. warmboldiae. Strains of Buttiauxella species are available from DSMZ, the German National Resource Center for Biological Material (Inhoffenstrabe 7B, 38124 Braunschweig, Germany). Buttiauxella sp. strain P1-29 deposited under accession number NCIMB 41248 is an example of a particularly useful strain from which a phytase may be obtained and used according to the invention. In some embodiments, the phytase is BP-wild type, a variant thereof (such as BP-11) disclosed in WO 06/043178 or a variant as disclosed in U.S. patent application Ser. No. 11/714,487, filed Mar. 6, 2007. For example, a BP-wild type and variants thereof are disclosed in Table 1 of WO 06/043178, wherein the numbering is in reference to SEQ ID NO:3 of the published PCT application.

In one preferred embodiment, a phytase useful in the instant invention is one having at least 75%, at least 80%, at least 85%, at least 88%, at least 90%, at least 93%, at least 95%, at least 96%, at least 97%, at least 98% and at least 99% sequence identity to the amino acid sequence set forth in SEQ ID NO:19 (BP-17) shown in Table 2 and variants thereof. More preferably, the phytase will have at least 95% to 99% sequence identity to the amino acid sequence set forth in SEQ ID NO:19 or variants thereof. In some embodiments, the phytase comprises or consists of the amino acid sequence of SEQ ID NO:19.

TABLE 2

Mature protein sequence of a phytase derived from Buttiauxella know as BP-17 phytase (SEQ ID NO: 19)

NDTPASGYQV EKVVILSRHG VRAPTKMTQT MRDVTPNTWP EWPVKLGYIT

PRGEHLISLM GGFYRQKFQQ QGILSQGSCP TPNSIYVWAD VDQRTLKTGE

AFLAGLAPQC GLTIHHQQNL EKADPLFHPV KAGTCSMDKT QVQQAVEKEA

QTPIDNLNQH YIPFLALMNT TLNFSTSAWC QKHSADKSCD LGLSMPSKLS

IKDNGNKVAL DGAIGLSSTL AEIFLLEYAQ GMPQAAWGNI HSEQEWASLL

KLHNVQFDLM ARTPYIARHN GTPLLQAISN ALNPNATESK LPDISPDNKI

LFIAGHDTNI ANIAGMLNMR WTLPGQPDNT PPGGALVFER LADKSGKQYV

SVSMVYQTLE QLRSQTPLSL NQPAGSVQLK IPGCNDQTAE GYCPLSTFTR

VVSQSVEPGC QLQ

In some embodiments the amount (dosage) of phytase used in the incubation and/or liquefaction processes is in the range of about 0.001 to 50 FTU/g ds, (e.g. in the range of about 0.01 to 25 FTU/g ds, about 0.01 to 15 FTU/g ds, about 0.01 to 10 FTU/g ds, about 0.05 to 15 FTU/g ds, and about 0.05 to 5.0 FTU/g.

Industrial Applications

The alpha-amylase blends presented herein possess valuable properties allowing for a variety of industrial applications. In particular, the amylase blends may be used for starch processes, in particular starch conversion, especially liquefaction of starch (see, e.g., U.S. Pat. No. 3,912,590, EP patent application nos. 252 730 and 63 909, WO 99/19467, and WO 96/28567 all references hereby incorporated by reference). Also contemplated are amylase blends that further comprise a glucoamylase, pullulanase, and/or another alpha-amylase.

Further, the amylase blends are particularly useful in the production of sweeteners and alcohols, such as ethanol or butanol, from starch or whole grains (see, e.g., U.S. Pat. No. 5,231,017, hereby incorporated by reference).

The amylase blends also are useful for desizing of textiles, fabrics and garments (see, e.g., WO 95/21247, U.S. Pat. No. 4,643,736, EP 119,920 hereby incorporated by reference), beer making or brewing, in pulp and paper production.

Starch Conversion

Conventional starch-conversion processes, such as liquefaction and saccharification processes are described, e.g., in U.S. Pat. No. 3,912,590 and EP patent publications Nos. 252,730 and 63,909, hereby incorporated by reference. In an embodiment the starch conversion process degrading starch to lower molecular weight carbohydrate components such as sugars or fat replacers includes a debranching step.

Starch to Sugar Conversion

In the case of converting starch into a sugar the starch is depolymerized. A representative depolymerization process comprises of a pre-treatment step and two or three consecutive process steps, viz. a liquefaction process, a saccharification process and dependent on the desired end product optionally an isomerization process.

Pre-Treatment of Native Starch

Native starch consists of microscopic granules, which are insoluble in water at room temperature. When an aqueous starch slurry is heated, the granules swell and eventually burst, dispersing the starch molecules into the solution. During this "gelatinization" process there is a dramatic increase in viscosity. As the solids level is 30-40% in a typical industrial process, the starch has to be thinned or "liquefied" so that it can be handled. This reduction in viscosity is today mostly obtained by enzymatic degradation.

Liquefaction

During the liquefaction step, the long chained starch is degraded into branched and linear shorter units by an alpha-amylase. The products may include glucose (a/k/a DP1), as well as maltodextrans and other short chain oligosaccharides (DP2+). The liquefaction process is carried out at 105-110° C. for 5 to 10 minutes followed by 1-2 hours at 95° C. The pH lies between 5.5 and 6.2. To ensure optimal enzyme stability under these conditions, 1 mM of calcium is added (40 ppm free calcium ions). After this treatment the liquefied starch will have a "dextrose equivalent" (DE) of 10-15.

Saccharification

After the liquefaction process the soluble dextrins and short chain oligosaccharides are converted into fermentable sugars such as glucose and maltose by addition of a glucoamylase (e.g., OPTIDEX® L-400) and a debranching enzyme, such as an isoamylase (U.S. Pat. No. 4,335,208) or a pullulanase. Before this step the pH is reduced to a value below 4.5, maintaining the high temperature (above 95° C.) to inactivate the liquefying alpha-amylase to reduce the formation of short oligosaccharide called "panose precursors" which cannot be hydrolyzed properly by the debranching enzyme.

The temperature is lowered to 60° C., and glucoamylase and a debranching enzyme are added. The saccharification process proceeds for 24-72 hours.

Normally, when denaturing the α-amylase after the liquefaction step about 0.2-0.5% of the saccharification product is the branched trisaccharide Glc pα1-6Glc pα1-4Glc (panose) which cannot be degraded by a pullulanase. If active amylase from the liquefaction step is present during saccharification (i.e., no denaturing), this level can be as high as 1-2%, which is highly undesirable as it lowers the saccharification yield significantly.

Isomerization

When the desired final sugar product is, e.g., high fructose syrup the dextrose syrup may be converted into fructose. After the saccharification process the pH is increased to a value in the range of 6-8, preferably pH 7.5, and the calcium is removed by ion exchange. The dextrose syrup is then converted into high fructose syrup using, e.g., an immmobilized glucose isomerase (such as Gensweet® IGI-HF).

Ethanol Production

In general alcohol production (ethanol) from whole grain can be separated into 4 main steps:
Milling
Liquefaction
Saccharification
Fermentation Milling The grain is milled in order to open up the structure and allow for further processing. Two processes used are wet or dry milling. In dry milling the whole kernel is milled and used in the remaining part of the process. Wet milling gives a very good separation of germ and meal (starch granules and protein) and is with a few exceptions applied at locations where there is a parallel production of syrups.

Preparing a Slurry of Starch-Containing Material

The milled starch-containing material will be combined with water and recycled thin-stillage resulting in an aqueous slurry. The slurry will comprise between 15 to 55% ds w/w (e.g., 20 to 50%, 25 to 50%, 25 to 45%, 25 to 40%, and 20 to 35% ds). In some embodiments the recycled thin-stillage will be in the range of 10 to 70% v/v (e.g., 10 to 60%, 10 to 50%, 10 to 40%, 10 to 30%, 10 to 20%, 20 to 60%, 20 to 50%, 20 to 40% and also 20 to 30%).

Once the milled starch-containing material is combined with water and thin-stillage, the pH is not adjusted in the slurry. Further the pH is not adjusted after the addition of phytase and optionally alpha amylase to the slurry. In a preferred embodiment the pH of the slurry will be in the range of pH 4.5 to less than 6.0 (e.g., pH 4.5 to 5.8, pH 4.5 to 5.6, pH 4.8 to 5.8, pH 5.0 to 5.8, pH 5.0 to 5.4 and pH 5.2 to 5.5). The pH of the slurry may be between pH 4.5 and 5.2 depending on the amount of thin stillage added to the slurry and the type of material comprising the thin stillage. For example, the pH of the thin stillage may be between pH 3.8 and pH 4.5. As a further example Table 3 below illustrates the pH change that occurs with addition of increasing amounts of thin stillage to a whole ground corn slurry (32% ds) after stirring for 2 hours at 155F.

TABLE 3

| Thin stillage w/w % | Final pH |
|---|---|
| 0 | 5.52 |
| 20 | 5.29 |
| 40 | 5.16 |
| 50 | 5.09 |
| 60 | 5.05 |
| 80 | 4.98 |
| 100 | 4.94 |

It should be mentioned, during ethanol production, acids can be added to lower the pH in the beer well to reduce the risk of microbial contamination prior to distillation.

In some embodiments, a phytase will be added to the slurry, in addition to the alpha amylase blend. In some embodiments, the phytase and alpha amylase blend will be added to the slurry sequentially and in other embodiments the phytase and alpha amylase blend will be added simultaneously. In some embodiments, the slurry comprising the alpha amylase blend and optional phytase will be incubated (pretreated) for a period of 5 minutes to 8 hours (e.g., 5 minutes to 6 hours, 5 minutes to 4 hours 5 minutes to 2 hours, and 15 minutes to 4 hours). In other embodiments the slurry will be incubated at a temperature in the range of 40 to 115° C., (e.g. 45 to 80° C., 50 to 70° C., 50 to 75° C., 60 to 110° C., 60 to 95° C., 70 to 110° C., and 70 to 85° C.).

In other embodiments, the slurry will be incubated at a temperature of 0 to 30° C. (e.g. 0 to 25° C., 0 to 20° C., 0 to 15° C., 0 to 10° C. and 0 to 5° C.) below the starch gelatinization temperature of the starch-containing material. In some embodiments, the temperature will be below 68° C., below 65° C., below 62° C., below 60° C. and below 55° C. In some embodiments, the temperature will be above 45° C., above 50° C., above 55° C. and above 60° C. In some embodiments, the incubation of the slurry comprising an alpha amylase blend and optional phytase at a temperature below the starch gelatinization temperature is referred to as a primary) (1° liquefaction.

In one embodiment the milled starch-containing material is corn or milo. The slurry comprises 25 to 40% ds, the pH is in the range of 4.8 to 5.2, and the slurry is incubated with an alpha amylase blend and optionally a phytase for 5 minutes to 2 hours, at a temperature range of 60 to 75° C.

In a further liquefaction step, the incubated or pretreated starch-containing material will be exposed to an increase in temperature such as 0 to 45° C. above the starch gelatinization temperature of the starch-containing material. (e.g. 70° C. to 120° C., 70° C. to 110° C., and 70° C. to 90° C.) for a period of time of 2 minutes to 6 hours (e.g. 2 minutes to 4 hrs) at a pH of about 4.0 to 5.5 more preferably between 1 hour to 2 hours. The temperature can be increased by a conventional high temperature jet cooking system for a short period of time for example for 1 to 15 minutes. Then the starch maybe further hydrolyzed at a temperature ranging from 75° C. to 95° C., (e.g., 80° C. to 90° C. and 80° C. to 85° C.) for a period of 15 to 150 minutes (e.g., 30 to 120 minutes). In a preferred embodiment, the pH is not adjusted during these process steps and the pH of the liquefied mash is in the range of pH 4.0 to pH 5.8 (e.g., pH 4.5 to 5.8, pH 4.8 to 5.4, and pH 5.0 to 5.2). In some embodiments, a second dose of a thermostable alpha amylase blend will be added to the secondary liquefaction step, but in other embodiments there will not be an additional dosage of an alpha amylase blend.

The incubation and liquefaction steps according to the invention may be followed by saccharification and fermentation steps well known in the art.

Liquefaction

In the liquefaction process the starch granules are solubilized by hydrolysis to maltodextrins mostly of a DP higher than 4. The hydrolysis may be carried out by acid treatment or enzymatically by alpha-amylase. Acid hydrolysis is used on a limited basis. The raw material can be milled whole grain or a side stream from starch processing.

Enzymatic liquefaction is typically carried out as a three-step hot slurry process. The slurry is heated to between 60-95° C., preferably 80-85° C., and the enzyme(s) is (are) added. Then the slurry is jet-cooked at between 95-140° C., preferably 105-125° C., cooled to 60-95° C. and more enzyme(s) is (are) added to obtain the final hydrolysis. The liquefaction process is carried out at pH 4.5-6.5, typically at a pH between 5 and 6. Milled and liquefied grain is also known as mash.

Fermentation

Yeast typically from *Saccharomyces* spp. is added to the mash and the fermentation is ongoing for 24-96 hours, such as typically 35-60 hours. The temperature is between 26-34° C., typically at about 32° C., and the pH is from pH 3-6, preferably around pH 4-5.

Note that the most widely used process is a simultaneous saccharification and fermentation (SSF) process where there is no holding stage for the saccharification, meaning that yeast and enzyme is added together. When doing SSF it is common to introduce a pre-saccharification step at a temperature above 50° C., just prior to the fermentation.

Saccharification and Fermentation

Liquefied starch-containing material is saccharified in the presence of saccharifying enzymes, such as glucoamylases. The saccharification process may last for 12 hours to 120 hours (e.g. 12 to 90 hours, 12 to 60 hours and 12 to 48 hours). However, it is common to perform a pre-saccharification step for about 30 minutes to 2 hours (e.g., 30 to 90 minutes) in a temperature range of 30 to 65° C. and typically around 60° C. which is followed by a complete saccharification during fermentation referred to as simultaneous saccharification and fermentation (SSF). The pH is usually between 4.2-4.8, preferably pH 4.5.

Fermentable sugars obtained from grains, including whole ground grains, and starches, including cornstarch, (e.g. dextrins, monosaccharides, particularly glucose) are produced from enzymatic saccharification. These fermentable sugars may be further purified and/or converted to useful sugar products. In addition the sugars obtained from whole ground grains may be used as a fermentation feedstock in a microbial fermentation process for producing end-products, such as alcohol (e.g., ethanol and butanol), organic acids (e.g., succinic acid, citric acid and lactic acid), sugar alcohols (e.g., glycerol), ascorbic acid intermediates (e.g., gluconate, 2-keto-D-gluconate, 2,5-diketo-D-gluconate, and 2-keto-L-gulonic acid), amino acids (e.g., lysine, glutamic acid and glutamates such as, for example monosodium glutamate), proteins (e.g., antibodies and fragment thereof).

In a preferred embodiment, the fermentable sugars obtained during the liquefaction process steps are used to produce alcohol and particularly ethanol. In ethanol production a SSF process is commonly used wherein the saccharifying enzymes and fermenting organisms (e.g., yeast) are added together and then carried out at a temperature of 30° C. to 40° C.

The organism used in fermentations will depend on the desired end-product. Typically if ethanol is the desired end product yeast will be used as the fermenting organism. In some preferred embodiments, the ethanol-producing microorganism is a yeast and specifically *Saccharomyces* such as strains of *S. cerevisiae* (U.S. Pat. No. 4,316,956). A variety of *S. cerevisiae* are commercially available and these include but are not limited to FALI (Fleischmann's Yeast), SUPER-START (Alltech), FERMIOL (DSM Specialties), RED STAR (Lesaffre) and Angel alcohol yeast (Angel Yeast Company, China). The amount of starter yeast employed in the methods is an amount effective to produce a commercially significant amount of ethanol in a suitable amount of time, (e.g. to produce at least 10% ethanol from a substrate having between 25-40% DS in less than 72 hours). Yeast cells are generally supplied in amounts of $10^4$ to $10^{12}$, and preferably from $10^7$ to $10^{10}$ viable yeast count per ml of fermentation broth. The fermentation will include in addition to a fermenting microorganisms (e.g. yeast), nutrients, optionally additional enzymes, including but not limited to phytases. The use of yeast in fermentation is well known and reference is made to THE ALCOHOL TEXTBOOK, K. JACQUES ET AL., EDS. 1999, NOTTINGHAM UNIVERSITY PRESS, UK.

In further embodiments, by use of appropriate fermenting microorganisms as known in the art, the fermentation end product may include without limitation glycerol, 1,3-propanediol, gluconate, 2-keto-D-gluconate, 2,5-diketo-D-gluconate, 2-keto-L-gulonic acid, succinic acid, lactic acid, amino acids and derivatives thereof. More specifically when lactic acid is the desired end product, a *Lactobacillus* sp. (*L. casei*) may be used; when glycerol or 1,3-propanediol are the desired end-products *E. coli* may be used; and when 2-keto-D-gluconate, 2,5-diketo-D-gluconate, and 2-keto-L-gulonic acid are the desired end products, *Pantoea citrea* may be used as the fermenting microorganism. The above enumerated list are only examples and one skilled in the art will be aware of a number of fermenting microorganisms that may be appropriately used to obtain a desired end product.

Distillation

Optionally, following fermentation, alcohol (e.g. ethanol or butanol) may be extracted by, for example, distillation and optionally followed by one or more process steps.

In some embodiments, the yield of ethanol or butanol produced by the methods encompassed by the invention will be at least 8%, at least 10%, at least 12%, at least 14%, at least 15%, at least 16%, at least 17% and at least 18% (v/v). and at least 23% v/v. The ethanol obtained according to the process of the invention may be used as, for example, fuel ethanol, drinking ethanol, i.e., potable neutral spirits, or industrial ethanol.

By-Products

Grain by-products from the fermentation typically are used for animal feed either in liquid form or dried form. If the starch is wet milled, non-starch by-products include crude protein, oil, and fiber, e.g., corn gluten meal. If the starch is dry-milled, the by-products may include animal feed co-products, such as distillers' dried grains (DDG) and distillers' dried grain plus solubles (DDGS). When the grain is dry milled and mixed in a slurry before liquefaction and saccharification, however, no grain is left as a by-product.

Further details on how to carry out liquefaction, saccharification, fermentation, distillation, and recovery of alcohols are well known to the skilled person.

According to the process of the invention the saccharification and fermentation may be carried out simultaneously or separately.

Glucoamylases and Pullulanases

Useful glucoamylases include those purified from *Aspergillus niger* (e.g., the G1 or G2 *A. niger* AMG disclosed in Boel et al. (1984), "Glucoamylases G1 and G2 from *Aspergillus niger* are synthesized from two different but closely related mRNAs", EMBO J. 3 (5), p. 1097-1102, or a variant thereof, in particular a variant disclosed in WO 00/04136 or WO 01/04273 or the *Talaromyces emersonii* AMG disclosed in WO 99/28448 or a *Trichoderma reesei* glucoamylase (see WO 06/060062).

In an embodiment the composition of the invention also comprises a pullulanase, e.g., a *Bacillus* pullulanase. See, for example, WO 99/45124.

Methods

Fermentation and Purification of Alpha-Amylase Variants

A *B. subtilis* strain harboring the relevant expression plasmid may be fermented and purified as follows: The strain is streaked on a LB-agar plate with 10 micro g/ml kanamycin from −80° C. stock, and grown overnight at 37° C. The colonies are transferred to 100 ml PS-1 media (below) supplemented with 10 micro g/ml chloamphinicol in a 500 ml shaking flask. The culture is shaken at 37° C. at 270 rpm for 5 days.

Composition of PS-1 Medium

| Pearl sugar | 100 g/l |
|---|---|
| Soy Bean Meal | 40 g/l |
| $Na_2HPO_4, 12H_2O$ | 10 g/l |
| Pluronic ™ PE 6100 | 0.1 g/l |
| $CaCO_3$ | 5 g/l |

Cells and cell debris are removed from the fermentation broth by centrifugation at 4500 rpm in 20-25 minutes. Afterwards the supernatant is filtered to obtain a completely clear solution. The filtrate is concentrated and washed on a UF-filter (10000 cut off membrane) and the buffer is changed to 20 mM Acetate pH 5.5. The UF-filtrate is applied on a S-sepharose F.F. and elution is carried out by step elution with 0.2M NaCl in the same buffer. The eluate is dialyzed against 10 mM Tris, pH 9.0 and applied on a Q-Sepharose F.F. and eluted with a linear gradient from 0-0.3M NaCl over 6 column volumes. The fractions that contain the activity (measured by the Phadebas assay) are pooled, pH was adjusted to pH 7.5 and remaining color was removed by a treatment with 0.5% W/vol. active coal in 5 minutes.

Specific Activity Determination

The specific activity is determined using the Phadebas® assay (Pharmacia) as activity/mg enzyme. The manufactures instructions are followed (see also below under "Assay for Alpha-Amylase Activity").

Stability Determination

The amylase stability may be measured using the method as follows:

The enzyme is incubated under the relevant conditions. Samples are taken at various time points, e.g., after 0, 5, 10, 15 and 30 minutes and diluted 25 times (same dilution for all taken samples) in assay buffer (50 mM Britton buffer pH 7.3) and the activity is measured using the Phadebas assay (Pharmacia) under standard conditions pH 7.3, 37° C.

Assays for Alpha-Amylase Activity

1. Phadebas Assay

Alpha-amylase activity is determined by a method employing Phadebas® tablets as substrate. Phadebas tablets (Phadebas® Amylase Test, supplied by Pharmacia Diagnostic) contain a cross-linked insoluble blue-colored starch polymer, which has been mixed with bovine serum albumin and a buffer substance and tabletted.

For every single measurement one tablet is suspended in a tube containing 5 ml 50 mM Britton-Robinson buffer (50 mM acetic acid, 50 mM phosphoric add, 50 mM boric acid, 0.1 mM $CaCl_2$, pH adjusted to the value of interest with NaOH). The test is performed in a water bath at the temperature of interest. The alpha-amylase to be tested is diluted in xml of 50 mM Britton-Robinson buffer. 1 ml of this alpha-amylase solution is added to the 5 ml 50 mM Britton-Robinson buffer. The starch is hydrolyzed by the alpha-amylase giving soluble blue fragments. The absorbance of the resulting blue solution, measured spectrophotometrically at 620 nm, is a function of the alpha-amylase activity.

It is important that the measured 620 nm absorbance after 10 or 15 minutes of incubation (testing time) is in the range of 0.2 to 2.0 absorbance units at 620 nm. In this absorbance range there is linearity between activity and absorbance (Lambert-Beer law). The dilution of the enzyme must therefore be adjusted to fit this criterion. Under a specified set of conditions (temp., pH, reaction time, buffer conditions) 1 mg of a given alpha-amylase will hydrolyze a certain amount of substrate and a blue color will be produced. The color intensity is measured at 620 nm. The measured absorbance is directly proportional to the specific activity (activity/mg of pure alpha-amylase protein) of the alpha-amylase in question under the given set of conditions.

2. Alternative Method

Alpha-amylase activity is determined by a method employing the PNP-G$_7$ substrate. PNP-G$_7$ which is a abbreviation for p-nitrophenyl-alpha,D-maltoheptaoside is a blocked oligosaccharide which can be cleaved by an endo-amylase. Following the cleavage, the alpha-Glucosidase included in the kit digest the substrate to liberate a free PNP molecule which has a yellow color and thus can be measured by visible spectophometry at λ=405 nm (400-420 nm). Kits containing PNP-G$_7$ substrate and alpha-Glucosidase is manufactured by Boehringer-Mannheim (cat. No. 1054635).

To prepare the reagent solution 10 ml of substrate/buffer solution is added to 50 ml enzyme/buffer solution as recommended by the manufacturer. The assay is performed by transferring 20 micro I sample to a 96 well microtitre plate and incubating at 25° C. 200 microliter reagent solution pre-equilibrated to 25° C. is added. The solution is mixed and pre-incubated 1 minute and absorption is measured every 30 seconds over 4 minutes at OD 405 nm in an ELISA reader.

The slope of the time dependent absorption-curve is directly proportional to the activity of the alpha-amylase in question under the given set of conditions.

Determination of Phytase Activity (FTU)

Phytase Activity (FTU) is measured by the release of inorganic phosphate. The inorganic phosphate forms a yellow complex with acidic molybdate/vanadate reagent and the yellow complex is measured at a wavelength of 415 nm in a spectrophotometer and the released inorganic phosphate is quantified with a phosphate standard curve. One unit of phytase (FTU) is the amount of enzyme that releases 1 micromole of inorganic phosphate from phytate per minute under the reaction conditions given in the European Standard (CEN/TC 327,2005-TC327WI 003270XX).

Determination of Phytic Acid Content

Phytic Acid Content:

Phytic acid was extracted from sample by adjusting the pH of the 5% slurry (if it is dry sample) to pH 10 and then determined by an HPLC method using an ion exchange column Phytic acid was eluted from the column using a NaOH gradient system. Phytic acid content in the liquid was then calculated by comparing to a phytic acid standard.

The present invention is described in further detail in the following examples which are not in any way intended to limit the scope of the invention as claimed. The attached figures are meant to be considered as integral parts of the specification and description of the invention. All references cited are herein specifically incorporated by reference for all that is described therein. The following examples are offered to illustrate, but not to limit the claimed invention.

EXAMPLES

In the disclosure and experimental section which follows, the following abbreviations apply: wt % (weight percent); ° C. (degrees Centigrade); H$_2$O (water); dH$_2$O (deionized water); dIH$_2$O (deionized water, Milli-Q filtration); g or gm (grams); μg (micrograms); mg (milligrams); kg (kilograms); μl (microliters); mL and ml (milliliters); mm (millimeters); μm (micrometer); M (molar); mM (millimolar); μM (micromolar); U (units); MW (molecular weight); sec (seconds); min(s) (minute/minutes); hr(s) (hour/hours); DO (dissolved oxygen); W/V (weight to volume); W/W (weight to weight); V/V (volume to volume); IKA (IKA Works Inc. North Chase Parkway SE, Wilmington, N.C.; Ncm (Newton centimeter) and ETOH (ethanol). eq (equivalents); N (Normal); ds or DS (dry solids content), AAU (Alpha Amylase Unit), LU (Liquefon Unit), SAPU (spectrophotometric acid protease unit, wherein in 1 SAPU is the amount of protease enzyme activity that liberates one micromole of tyrosine per minute from a casein substrate under conditions of the assay) and GAU (glucoamylase unit, which is defined as the amount of enzyme that will produce 1 g of reducing sugar calculated as glucose per hour from a soluble starch substrate at pH 4.2 and 60° C.).

Example 1

Construction of Variants

The variants at position S242 of the mature sequence of AmyS were constructed using a site directed approach.

The template for mutagenesis was methylated pHPLT-AmyS (see FIG. 2) using dam-Methylase from New England Biolabs (Massachusetts). Degenerate primers (S242F(orward) and S242R(everse), given below) were synthesized and diluted to 10 uM at Operon (Huntsville, Ala.) with complementary forward and reverse sequences both containing a 5' phosphate for ligation in the reaction. The sequence of the parent alpha-amylase is attached hereto as SEQ ID NO: 2. Libraries were created with the Stratagene Quik-Change™ Multi-site kit (Stratagene, La Jolla Calif.) using oligonucleotide primers randomized with NN(G/C) at the target position. The selected amino acid (i.e., S242) was randomly replaced with all 19 possible alternatives.

S242 Primers for Mutagenesis:

```
S242 F: 5' [Phos]GTCAAGCATATTAAGTTCNNSTTTTTTCCTGATTGGTTG 3' SEQ ID NO: 17

S242 R: 5' [Phos]CAACCAATCAGGAAAAAASNNGAACTTAATATGCTTGAC 3' SEQ ID NO: 18
```

The reaction was performed as follows:

Quik-Change Reaction:

The reaction consisted of 18 μl of sterile distilled H$_2$O, 2.5 μl of 10× buffer from the kit, 1 uL dNTPs from the kit, 1.25 μl of the forward primers (of 10 uM stock), 1.25 μl of the reverse primers (of 10 μM stock), 1 μl of pHPLT-AmyS plasmid DNA as template (~70 ng), and 1 μl of the enzyme blend from the kit for a total of 26.5 μl.

Cycling Conditions:

The cycling conditions were 95° C. for 1 min once, then 95° C. for 1 min, 55° C. for 1 min, 65° C. for 10 min for 25 cycles.

One microliter Dpn I (10 U/μl) was added to the Multi-site Quik-Change reaction mixture and incubated at 37° C. for 18 hours and then another 0.5 μl was added for an additional 3 hours.

One microliter of DpnI digested reaction was used as template for rolling circle amplification with the Templiphi amplification kit (Amersham Biosciences, Piscataway, N.J.) and the reaction was performed according to the Amersham protocol. One microliter of rolling circle DNA was transformed into 100 ul of Bacillus subtilis competent cells (2 protease deleted B. subtilis strain (ΔaprE, ΔnprE, amyE::

xylRPxylAcomK-phleo)) and shaken at 37° C. for 1 hour. The entire transformation was next plated on LA+10 ppm Neo+ 1% insoluble starch plates (25 ul one plate, 75 μl on another plate) and incubated overnight at 37° C. Ninety six transformants were picked into 150 ul of LB+10 ppm Neo in a micro-titer plate and grown overnight at 37° C. The overnight plate was stamped onto a large LA+10 ppm Neo+1% insoluble starch plate with a 96 pin replicating tool and submitted to Quintara Biosciences (Berkeley, Calif.) for colony PCR and sequencing.

After variant sequences were determined, the variants were picked into a 96 well micro-titer plates containing 125 ul of LB+10 ppm Neo, arraying the variants into a quad format with controls. The arrayed micro-titer plate was grown for 6 hours at 37° C. and 250 rpm. Using a replicating tool (Enzyscreen, Leiden, The Netherlands) the micro-titer culture plate was used to inoculate a new micro-titer plate (micro-titer plate and plate lids from Enzyscreen, Leiden, The Netherlands) containing 150 ul of MBD medium for protein expression (G. Vogtentanz et al, A Bacillus subtilis fusion protein system to produce soybean Bowman-Birk protease inhibitor, Prot. Expr. & Purif., 55 (2007) 40-52) and supplemented with 5 mM $CaCl_2$ for protein expression. Expression plates were grown for 64 hours at 37° C., 250 rpm, and 70% humidity. Expression cultures were next filtered through a micro-filter plate (0.22 um, Millipore, Billerica, Mass.) and screened for improved thermostability (see Example 3).

Example 2

Expression, Purification & Characterization of Variants

Colonies were streaked from the microtiter plates from Example 1 and put onto starch plates with 10 ppm Neomycin. The plates were incubated overnight at 37° C. and singles colonies were picked and used to inoculate shake flasks (250 mL with 25 mL media) containing media (see below) and 20 ppm Neomycin. These were grown up at 37° C., 275 rpm, for about 8 hrs (till an OD (600 nm) of 2.0 was reached). Whereupon the culture broths were mixed with 50% glycerol at 2:1 ratio, put into individually labeled culture vials and frozen at −80° C. It was from these glycerol stocks that subsequent production of the selected amylases were made.

Fermentations for amylases were carried out in 500 mL shake flasks grown at 37° C. for 60 hours in minimal MOPS culture medium (Neidhardt et al., J. Bacteriol. (1974) 119(3): 736-747) with 1% (w/v) Soytone. Enzymes were purified from the fermentation broth using hydrophobic interaction chromatography. In brief, the broth were concentrated 10-fold then diluted back with 50 mM MES, 2 mM $CaCl_2$, pH 6.8 with 1M ammonium sulfate and sterile filtered using glass fiber filter. Samples were then load onto phenyl sepharose FF high density column (20×95 mm; Amersham, GE Healthcare Bio-Sciences, Sweden) pre-equilibrated with the same buffer. Non-amylase proteins were washed off with 10 column volumes of the same buffer without ammonium sulfate followed by 5 column volumes of water. Finally, enzymes of interest were eluted with 50 mM MES, 2 mM $CaCl_2$, pH 6.8 containing 40% propylene glycol.

Protein concentrations were determined either by a standard quantitative SDS page gel densitometry method or by an activity assay using a standard amylase assay kit from Megazyme (Wicklow, Ireland). Assays were converted using a standard curve generated using purified amylase (Bacillus 707 amylase; SEQ ID NO: 6).

Example 3

Determination of Altered Properties: Thermal Stress

This example shows that the variants described herein may have an altered property relative to the parent alpha-amylase. A high throughput thermal stability screen of G. stearothermophilus alpha-amylase (AmyS) variants was carried out.

Heat stress conditions were investigated and chosen such that after the heat stress the starting wild-type enzyme showed approximately 40% of its unstressed activity (i.e., activity after heat stress/activity before heat stress was approximately 0.4). Libraries of mutants were screened in quadruplicate, and potential winners were identified as those that showed residual activity after heat stress that was at least two standard deviations more than the average residual activity of the starting wildtype enzyme.

Amylase expression was approximately 100 ppm in the culture supernatants of the expression plates. After 60-65 hours of growth at 37° C. in a humidified shaker (250 rpm and 70% relative humidity), the culture supernatants were clarified to remove cellular material using filter plates. The clarified supernatants were diluted 10-fold into buffer containing 50 mM NaOAc/2.6 mM $CaCl_2$/0.002% Tween-20, pH 5.8., to a final concentration of approximately 10 ppm. One aliquot of the supernatant was further diluted to 0.02 ppm, and activity of the enzyme variants were determined as described below using a fluorescently-labeled corn starch substrate. A second aliquot of the supernatant was subjected to a 30 minute heat stress at 95° C. in a thermocycler before being diluted to 0.02 ppm in 50 mM NaOAc/2.6 mM $CaCl_2$/0.002% Tween-20, pH 5.8 and assayed for residual activity using the same fluorescent substrate and assay described below.

Amylase activity was determined using the amylase EnzCheck assay essentially as described by the manufacturer (Invitrogen, San Diego Calif.). Final concentration of the amylase in the assay was approximately 0.02 ppm. Assay buffer was 50 mM NaOAc/2.6 mM $CaCl_2$/0.002% Tween-20, pH 5.8. The substrate was BODIPY fluorescence dye conjugated 100 μg/mL DQ™ starch from corn (Invitrogen—Eugene, Oreg.). Increased fluorescence, indicating amylase activity, was measured using a Spectomax M2 (Molecular Devices, Sunnyvale, Calif.). The reaction was monitored at room temperature for 5 minutes with the instrument recording in kinetic mode. Excitation wavelength was 485 nm; emission was monitored at 520 nm with a cutoff filter at 515 nm.

Figure 3:
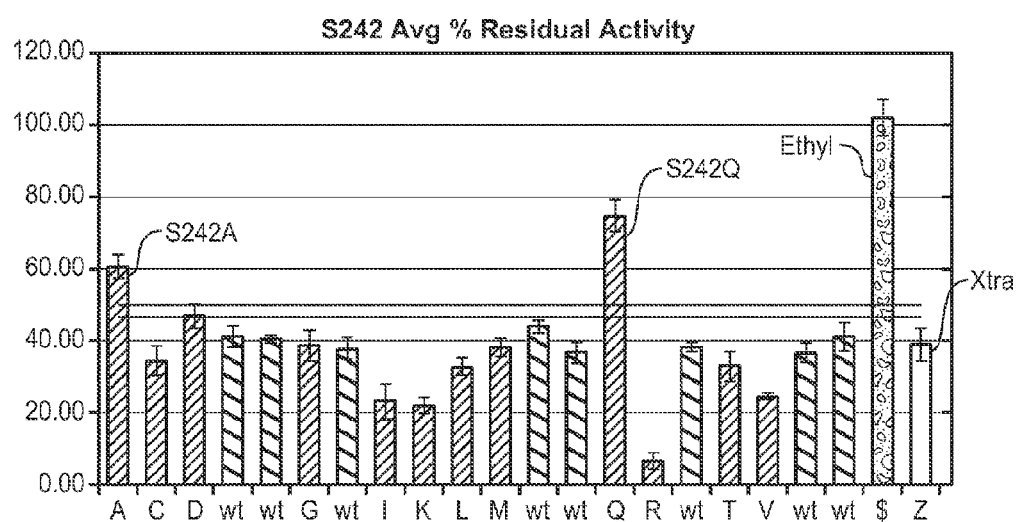
FIG. 3 shows percent residual activity of S242 library variants after heat stress at 95° C. for 30 minutes. Variant positions P, S, W, and Y are missing and are replaced by wild type AmyS ("wt"). A SPEZYME®® Xtra control is labeled "Z." Another positive control, AmyS with a A179-180 deletion and a C-terminus truncation of 29 amino acids (SEQ ID NO: 16) is also shown ("$"). S242A and S242Q clearly show higher residual activities than the wild type.

The wild type AmyS (Xtra) showed 33-43% residual activity after being subject to thermal stress for 30 minutes at 95° C. AmyS variants S242A and S242Q retained 55-65% and 70-80% residual activities, respectively, following the same thermal stress conditions. See FIG. 3 and Table 4. These residual activity measurements indicate the two variants are more thermostable than the wild type alpha amylase. In Table 4, percent residual activities of each variant samples are listed. Some variants were missing from the libraries, as indicated by the position letter being struck out. In the place of the variants, wild-type (SPEZYME® Xtra) was used, as shown by the term "WT." Each plate includes SPEZYME® Ethyl (labeled "$") and SPEZYME® Xtra (labeled "Z") as controls.

TABLE 4

| Variants | % Residual Activity | | | | Average | Stdev | % CV |
|---|---|---|---|---|---|---|---|
| A | 60.6 | 59.8 | 56.5 | 64.6 | 60.4 | 3.3 | 5 |
| C | 38.1 | 35.6 | 28.3 | 34.5 | 34.1 | 4.2 | 12 |
| D | 50.6 | 42.9 | 45.0 | 48.7 | 46.8 | 3.5 | 7 |
| E (WT) | 45.3 | 38.6 | 39.5 | 40.7 | 41.0 | 3.0 | 7 |
| F (WT) | 40.5 | 40.2 | 41.2 | 38.9 | 40.2 | 1.0 | 2 |
| G | 36.4 | 35.7 | 44.8 | 36.7 | 38.4 | 4.3 | 11 |
| H (WT) | 34.9 | 36.9 | 37.0 | 42.1 | 37.7 | 3.0 | 8 |
| I | 20.9 | 26.7 | 27.5 | 17.2 | 23.1 | 4.9 | 21 |
| K | 22.6 | 21.5 | 19.3 | 24.5 | 22.0 | 2.2 | 10 |
| L | 34.9 | 30.7 | 34.5 | 30.7 | 32.7 | 2.3 | 7 |
| M | 35.3 | 37.3 | 38.3 | 41.3 | 38.1 | 2.5 | 7 |
| N (WT) | 43.9 | 43.2 | 46.0 | 42.2 | 43.8 | 1.6 | 4 |
| P (WT) | 33.8 | 35.6 | 40.2 | 37.4 | 36.8 | 2.7 | 7 |
| Q | 80.6 | 71.0 | 75.9 | 71.5 | 74.8 | 4.5 | 6 |
| R | 9.6 | 4.5 | 6.1 | 5.4 | 6.4 | 2.2 | 35 |
| S (WT) | 38.6 | 39.9 | 37.2 | 37.3 | 38.3 | 1.3 | 3 |
| T | 36.8 | 31.5 | 35.1 | 27.8 | 32.8 | 4.0 | 12 |
| V | 25.0 | 24.7 | 25.0 | 22.9 | 24.4 | 1.0 | 4 |
| W (WT) | 32.7 | 37.5 | 36.3 | 38.8 | 36.3 | 2.6 | 7 |
| Y (WT) | 37.1 | 42.6 | 46.0 | 38.6 | 41.1 | 4.0 | 10 |
| $ (Ethyl3) | 108.9 | 101.9 | 95.9 | 101.5 | 102.0 | 5.3 | 5 |
| Z (Xtra) | 38.8 | 41.5 | 42.5 | 32.7 | 38.9 | 4.4 | 11 |

Example 4

Determination of Altered Properties: DSC

SPEZYME® Xtra, S242A, and S242Q were purified from shake flask fermentation broth (see Example 2) using hydrophobic interaction chromatography. The protein was eluted from the column in purified form using 50 mM MES, pH 6.8, containing 40% propylene glycol and 2 mM $CaCl_2$.

Figure 5:
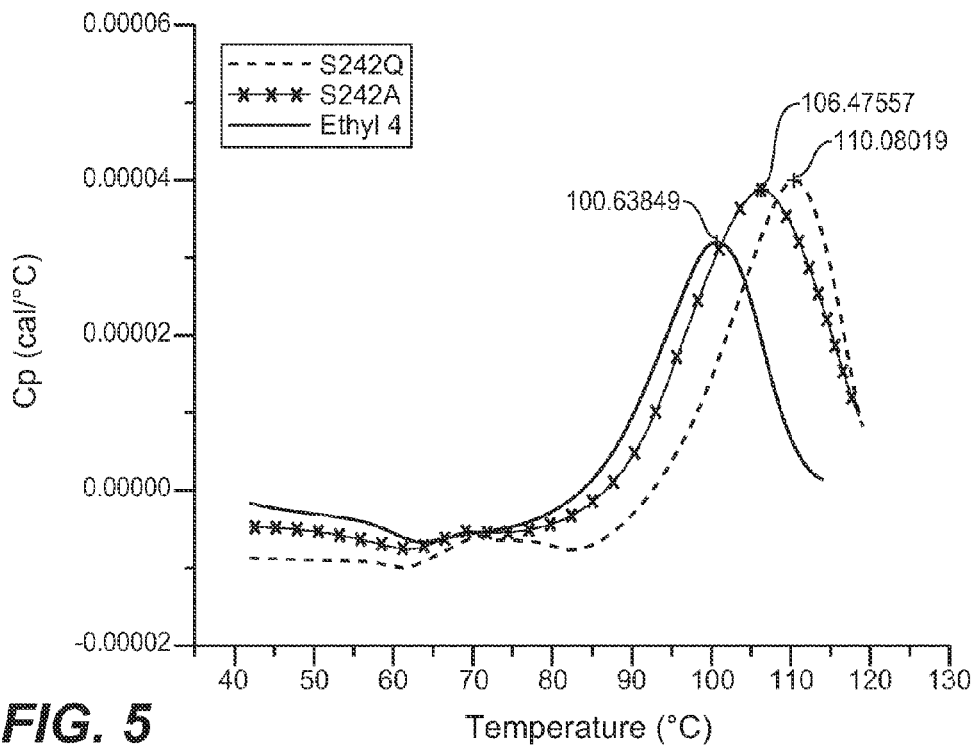
FIG. 5 shows the thermal melting curves and the melting points for the wild type and amylase variants without added calcium.

Excess heat capacity functions were measured using an ultrasensitive scanning high-throughput microcalorimeter, VP-Cap DSC (MicroCal, Inc., Northampton, Mass.). The standard procedure for DSC measurements and the theory of the technique is previously published (Freire, E. (1995) Differential Scanning calorimetry Methods. *Mol. Biol.* 41, 191-218). Approximately 500 µL of 0.5 mg/ml wild type *Bacillus stearothermophilus* α-amylase or variant S242S and S242Q (in the absence and presence of 2 mM calcium chloride) were scanned over 30-120° C. temperature range. The same sample was then re-scanned to check the reversibility of the process. For α-amylase the thermal unfolding process was irreversible. The buffer used was 10 mM sodium acetate, pH 5.5. A 200° C./hr scan rate was used to minimize any artifacts that may result from aggregation. The thermal midpoint (Tm) of the DSC curves was used as an indicator of the thermal stability. Table 5 shows the thermal melting points for the amylase proteins tested. The thermal melting curves and the melting points for the wild type and amylase variants are shown in FIG. 5.

The thermal unfolding for the amylase variants S242A and S242Q in the absence and presence of 2 mM calcium chloride show considerable increase in the melting points for the variants when compared to that for the wild type. In the absence of added calcium chloride, the wild type amylase has a thermal melting point of 100.8° C. whilst the Tm's for S242A and S242Q are 106.5° C. and 110.1° C., respectively. Thus, the substitution of S242 with A results in an increase in the Tm of 5.7° C., and the substitution of S242 with Q results in an increase in the Tm of 9.3° C.

In the presence of 2 mM calcium chloride, the wild type amylase characterized has a thermal melting point of 106.8° C. whilst the Tm's for S242A and S242Q are 111.8° C. and 113.8° C., respectively. Thus, in the presence of 2 mM calcium chloride all three proteins displayed increased Tm values. The increase in Tm for wild type and the S242A variants was 6° C. and 5.3° C., respectively. The increase in Tm for the S242Q variants was 3.7° C. This suggests that the S242Q variants is stabilized less by calcium or is less dependent on calcium for stability. The increase in the Tm of the S242A and S242Q relative to wild type in the presence of calcium chloride was 5° C. and 3° C., respectively. This suggests that the thermodynamic properties of the variants differ from those of SPEZYME® Xtra, and is consistent with its enhanced performance in application studies (see Example 5).

TABLE 5

|  | Tm (no Ca2+) | Tm (w/2 mM Ca2+) |
|---|---|---|
| SPEZYME ® Xtra | 100.8 | 106.8 |
| S242A | 106.5 | 111.8 |
| S242Q | 110.1 | 113.8 |

Example 5

Activity Profiles

This example shows that the tested variants have altered activity profiles relative not only to the parent alpha-amylase but also to an industry standard. Protein determinations were made on purified or plate samples. All experimental variants and standard alpha-amylases were dosed on equal protein concentrations.

Either plate or purified variants were diluted down to approximately 20 ppm using pH 5.6 malic acid buffer. The substrate consisted of 15% corn starch in the same 50 mM Malic acid buffer, pH 5.6. Four hundred microliters of the starch suspension was equilibrated to 70° C. for 2.5 minutes. Then 7 ul of the diluted enzyme was quickly added to the equilibrated starch (final protein conc. around 0.36 ppm). The reaction mix was then put into a pre-heated 85° C. shaking heating block and mixed at 300 rpm. At predetermined time intervals the reactions were quenched with 50 ul of 125 mM NaOH. The reaction tubes were then spun and the supernatent was diluted 10 fold into 10 mM NaOH, to be analyzed for DP profile by HPAEC-PAD.

Reactions were set up for 4, 10 and 20 minutes. Total area from DP2 to the end of the HPLC run was integrated and the area was divided by the total protein and reaction time.

Figure 6:
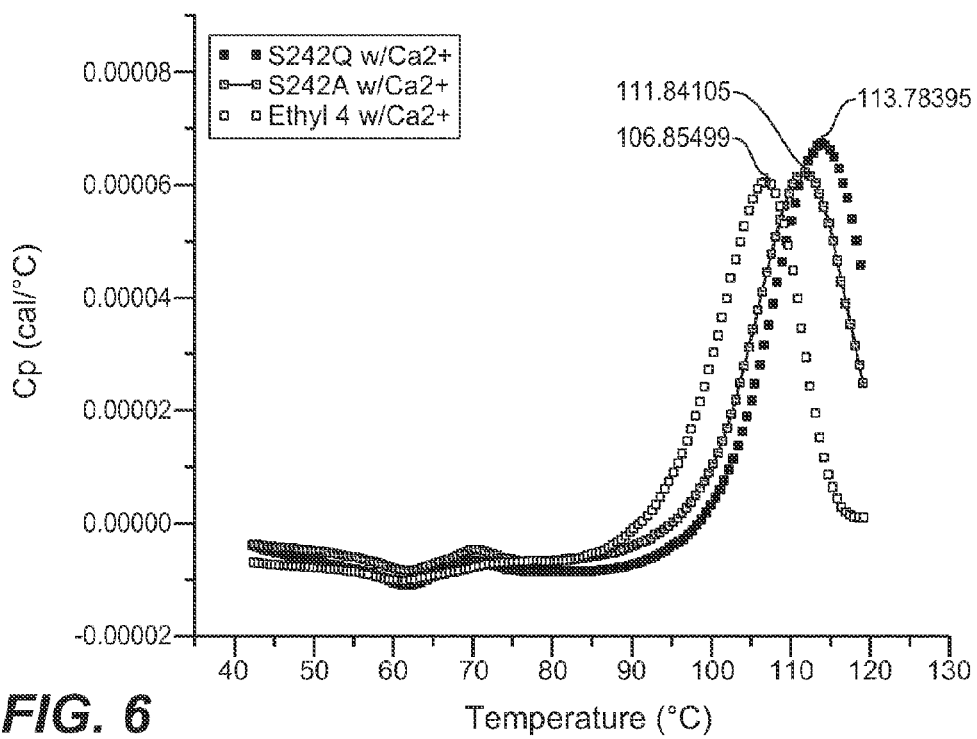
FIG. 6 shows the thermal melting curves and the melting points for the wild type and amylase variants with calcium.
Figure 7:
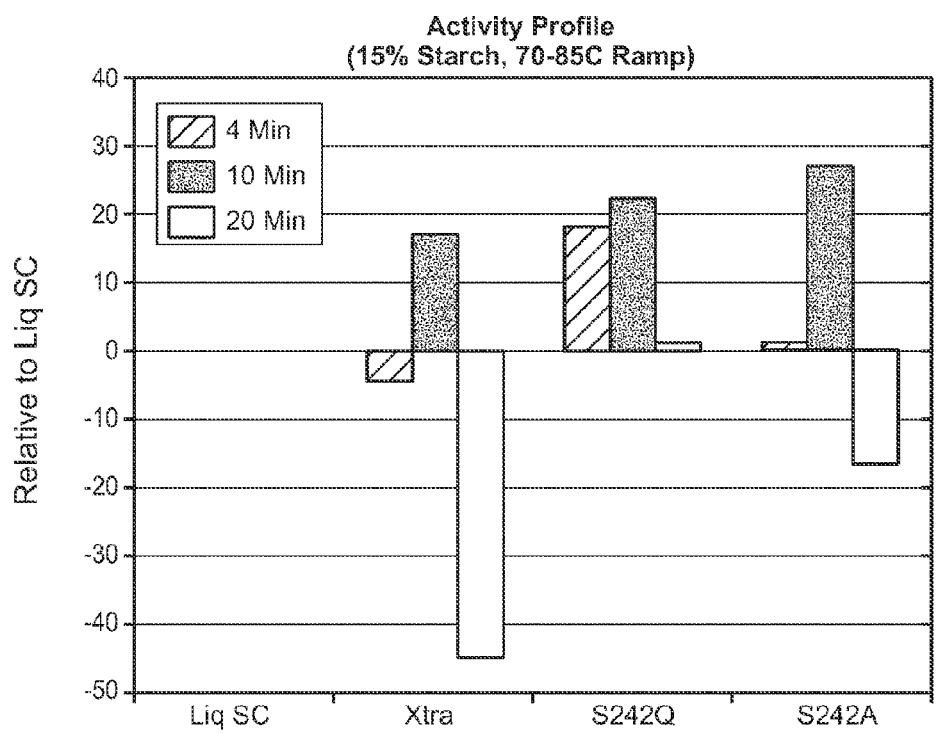
FIG. 7 shows the activity profile of SPEZYME® Xtra and two variants relative to Liquozyme SC for three time points.

The 4 min reaction provides an indication of how quickly the enzyme begins to break down the substrate; the 10 minute provides an indication of the enzyme's thermal activity, and the 20 minute provides an indication of the enzyme's thermal stability. The results are provided in FIG. 6 and FIG. 7.

Example 6

Liquefaction in the Viscometer

This example shows that the S242A and S242Q variants of Example 3 that had altered residual activity relative to the wild-type parent also have altered performance relative to the parent alpha-amylase. The variant alpha-amylases of Example 2 were purified and characterized for total protein and specific activity before its test in the application.

Viscosity reduction of corn flour due to the action of the alpha-amylase was monitored using a HAAKE Viscotester 550 instrument. The substrate slurry is made up fresh daily in batch mode with 30% corn flour dry solids. The pH was adjusted to 5.8 using sulfuric acid. 50 g of the slurry (15 g dry solids) is weighed out and pre-incubated, with stirring, for 10 minutes to warm up to 70° C. Upon alpha amylase addition the temperature is immediately ramped up from 70° C. to 85° C. with a rotation speed of 75. Once the temperature of the slurry and enzyme mixture reaches 85° C., its temperature is held constant and viscosity is monitored for an additional 30 minutes. The viscosity was measured throughout the run and is reported in uNm. Wild-type AmyS, S242A, and S242Q were all dosed at equal protein concentrations (20 or 30 ug/50 g of corn flour slurry).

Figure 8:
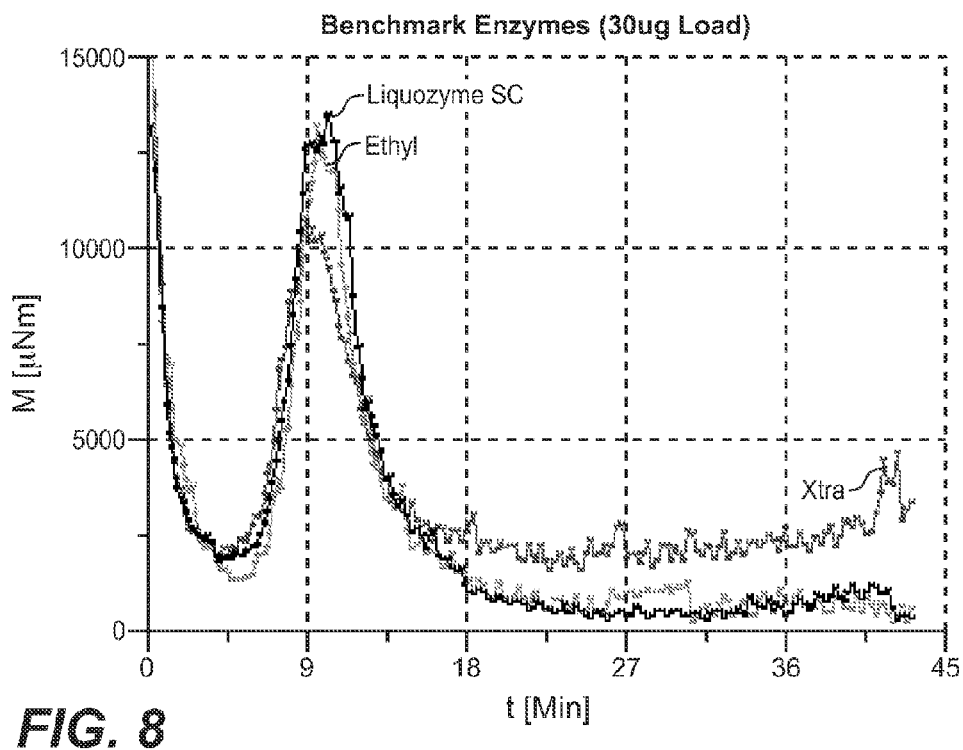
FIG. 8 shows the viscosity reduction of corn flour due to the action of the alpha-amylases Liquozyme SC, SPEZYME® Ethyl or SPEZYME® Xtra at a 30 ug dose.
Figure 9:
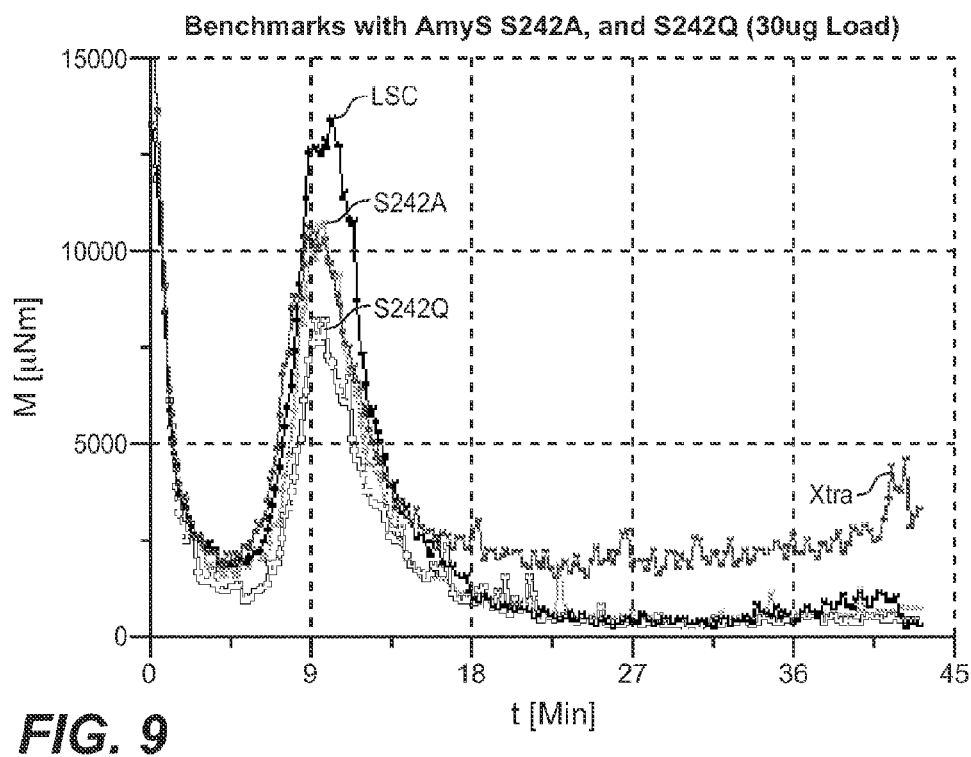
FIG. 9 shows the viscosity reduction of corn flour due to the action of the alpha-amylases Liquozyme SC or SPEZYME® Xtra, or one of two variants (S242A and S242Q) at a 30 ug dose.
Figure 10:
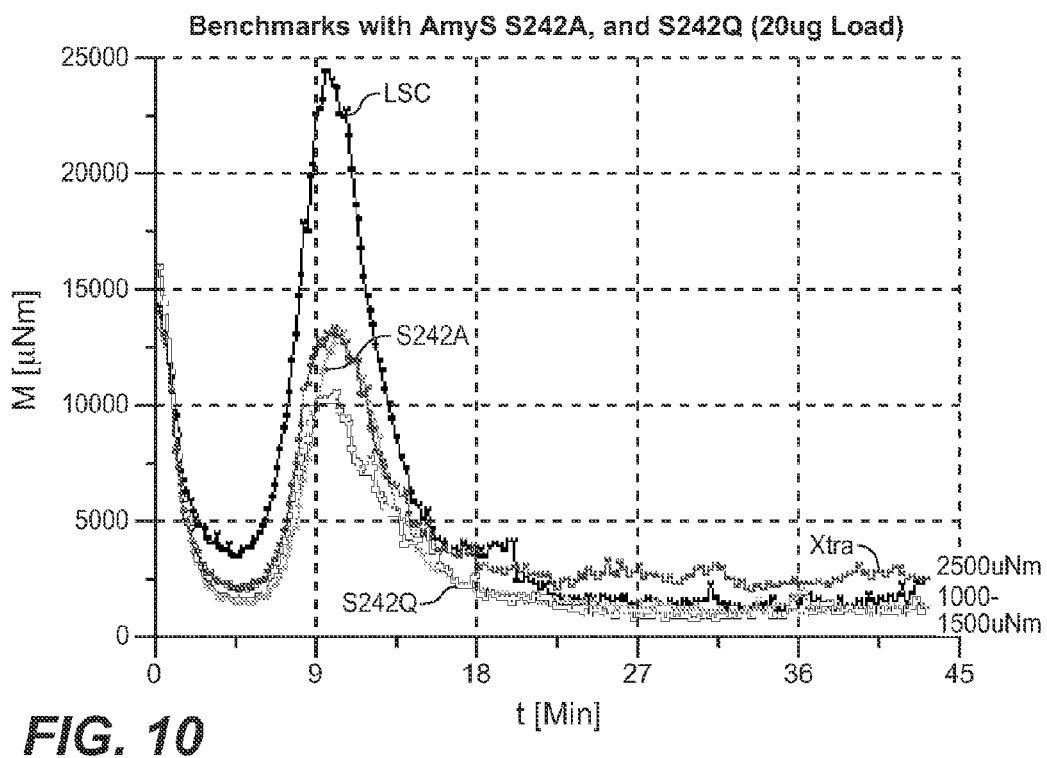
FIG. 10 shows the viscosity reduction of corn flour due to the action of the alpha-amylase Liquozyme SC or SPEZYME® Xtra, or one of two variants (S242A and S242Q) at a 20 ug dose.

The viscometer application test resulted in both AmyS variants, S242A and S242Q, having better performance than the benchmark alpha amylases—Liquozyme SC, Ethyl, and Xtra. Both variants exhibit the low peak viscosity characteristic of Xtra and low final viscosity of Liquozyme SC and Ethyl. When loaded at the lower concentration of 20 ug total protein, the differences of lower peak viscosities of the variants compared to that of Liquozyme SC are further enhanced. See FIGS. 8, 9 and 10.

Example 7

Liquefaction in a Jet Cooker

Figure 11:
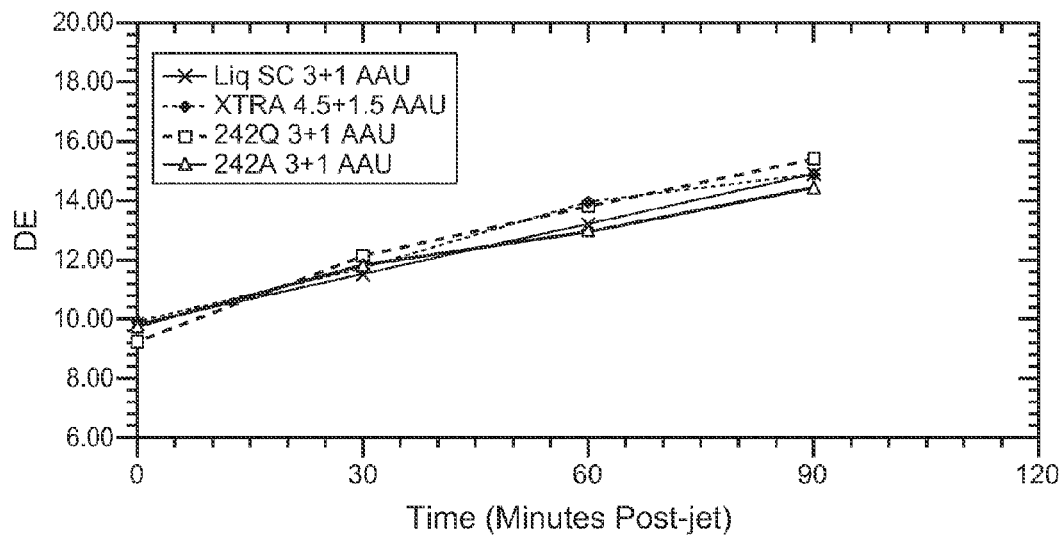
FIG. 11 shows the DE progression of whole ground corn treated with Liquozyme SC, SPEZYME® Xtra, or one of two variants (S242A and S242Q) over time (0, 30, 60 and 90 minutes).
Figure 12:
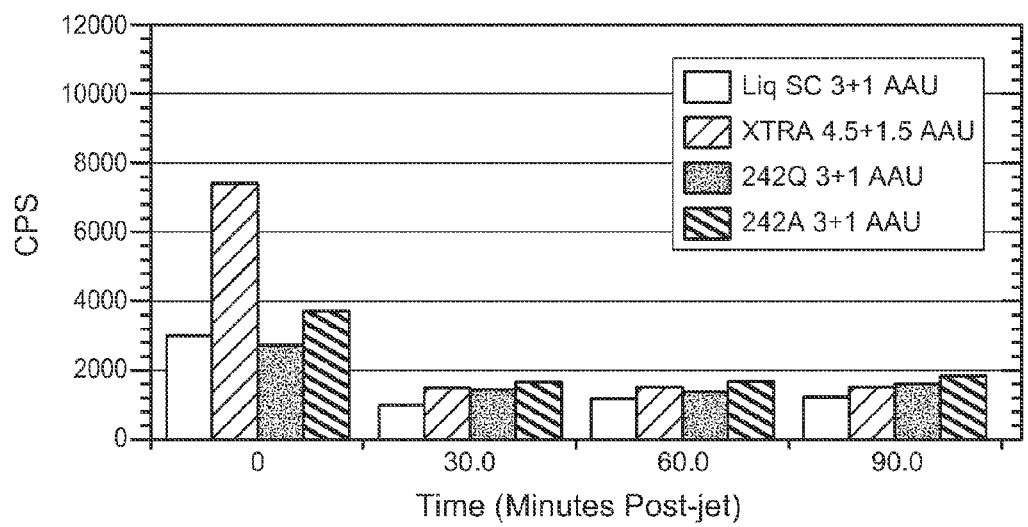
FIG. 12 shows the viscosity post-jet of whole ground corn treated with Liquozyme SC, SPEZYME® Xtra, or one of two variants (S242A and S242Q) over time (0, 30, 60 and 90 minutes).

Whole ground corn was slurried to a 32% (dry solids corn) slurry by using a 70:30 ratio of water to thin stillage. The slurry pH was adjusted to pH 5.8 with 10N NaOH. The slurry was heated to 70° C. (158° F.) using water and steam in a jacketed kettle. The liquefaction enzymes (SPEZYME® Xtra, LiquozymeSC, or S242Q) were added and the slurry was heated to 85° C. (185° F.) over approximately 10 minutes. After an additional 10 minutes of incubation at 85° C., the slurry was passed through a jet-cooker maintained at 107° C. (225° F.) with a 3 minute hold time using a large pilot plant jet (equipped with an M103 hydro-heater from Hydro-thermal Corp., Waukesha, Wis.). The liquefact was collected from the jet and placed in an 85° C. water bath. A second dose of liquefaction enzyme was added post-jet. The liquefact was continuously stirred and held at 85° C. for 90 minutes. Samples were collected at 0, 30, 60 and 90 minutes. All samples were tested post-jet for DE (using the Schoorls method; method available upon request), and for viscosity (Brookfield-type viscometer (Lab-line Instruments Inc. of Melrose Park, Ill.) spindle 3 at 20 rpms). Dosing of liquefaction enzymes pre- and post-jet are indicated in the following figures as "X+Y" where X represents the number of units of enzyme added before the jet, and Y represents the number of units added to the liquefact after it passes through the jet cooker. Results are shown in FIGS. 11 and 12.

Example 8

Batch liquefaction Using Blend of Alpha-Amylases AmyS S242Q and SPEZYME® FRED

Whole ground corn from Lader's feed mill (Tiffany, Wis.) was used. SPEZYME® FRED lab standard (activity 17,662 AAUs/g) and AmyS S242Q lab standard (activity 14,234 AAUs/g) were used.

Three identical slurries of whole ground corn (700 g) were prepared with water containing 30% v/v thin stillage (obtained from United Ethanol, Milton, Wis.) at 32% DS. The samples were adjusted to pH 5.8 using 6N NaOH. The slurries were held in an 85° C. water bath with mixing and AmyS S242Q (4 AAUs/g ds corn), Fred (20 LUs/g ds corn), and a blend of AmyS S242Q and Fred (2.8 AAUs/g ds corn and 6 LUs/g ds corn) were added to each slurry, respectively. Timing was initiated when the slurry temperature reached 85° C. Samples were taken to test for DE (by Schoorls), ° Brix, and viscosity (by Brookfield) at 30, 60, 90 and 120 minutes. The DE progression and viscosity data are summarized in FIG. 13 and FIG. 14.

Figure 13:
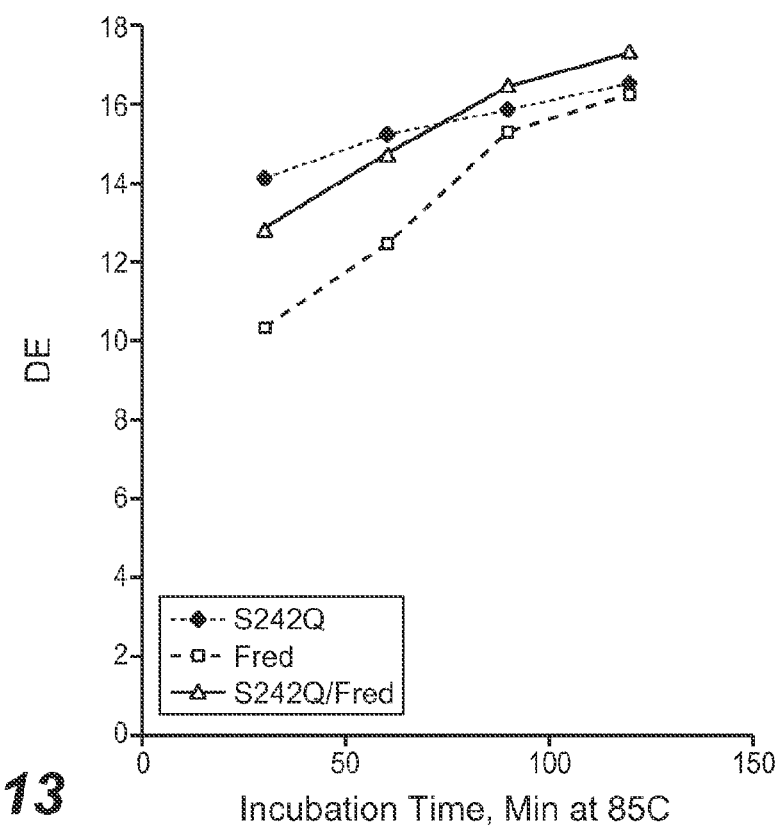
FIG. 13 shows the DE progression of whole ground corn treated with a blend of AmyS S242Q (SEQ ID NO: 4) and SPEZYME® FRED, and each enzyme individually, in a batch liquefaction process at 85-90° C. over time (30, 60, 90 and 120 minutes).
Figure 14:
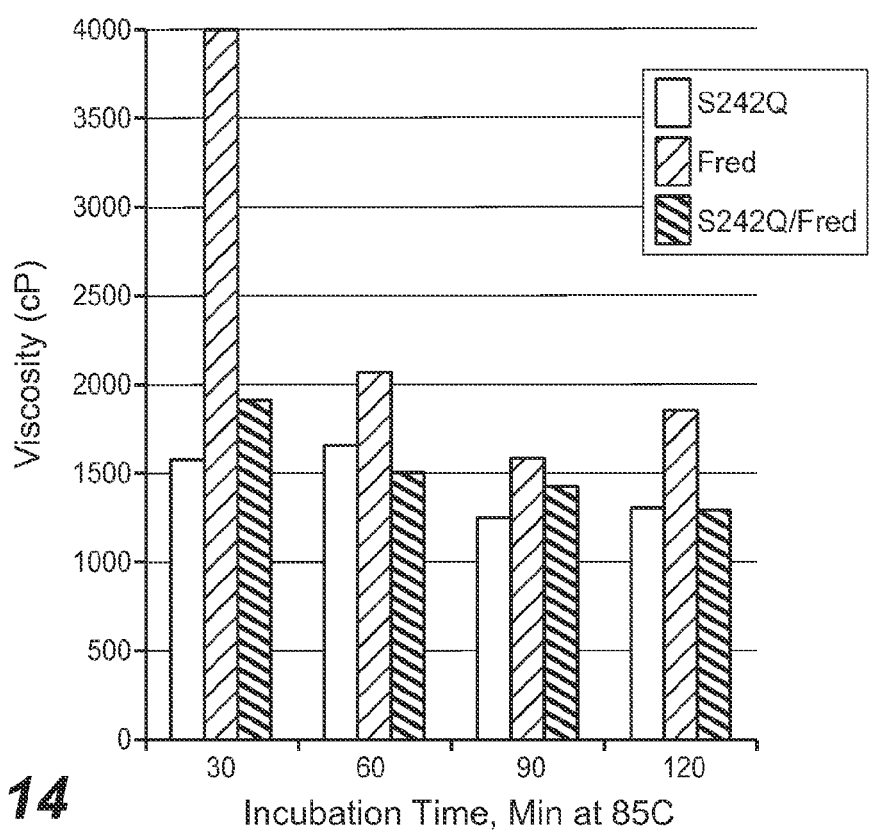
FIG. 14 shows the slurry viscosity of whole ground corn treated with a blend of AmyS S242Q (SEQ ID NO: 4) and SPEZYME® FRED, and each enzyme individually, in a batch liquefaction process at 85-90° C. over time (30, 60, 90 and 120 minutes).

As shown in FIG. 13 and FIG. 14, the AmyS S242Q/Fred blend satisfactorily reduced the slurry viscosity to 1923 cP in 30 min. In addition the sample containing the AmyS S242Q/Fred blend maintained a high DE progression slope for 120 min, which indicated good thermostablility. Regarding viscosity reduction, FIG. 14 shows that AmyS S242Q alone rapidly reduced viscosity to 1584 cP in 30 min, while Fred alone resulted in a very high viscosity of 12,000 cP at 30 min sampling. Fred alone did reduce viscosity to less than 2000 cP by 90 minutes of liquefaction time, but as noted above, this length of time would not be useful in ethanol production as currently practiced.

In summary, the ground corn slurry treated with the AmyS S242Q/Fred blend demonstrates the key properties needed for efficient ethanol production, namely a rapid decrease in slurry viscosity to below 2000 cP (in about 30 minutes), which is appropriate for ethanol plants, and also a high DE progression slope throughout 120 min of liquefaction time, demonstrating thermostability. Thus, the combination AmyS S242Q and Fred at these activity levels results in markedly better properties than either enzyme separately.

Example 9

Glucose Syrup Production using Blend of Alpha-Amylases AmyS S242Q and SPEZYME® FRED A glucose syrup was prepared from a starch substrate. The substrate was prepared as a slurry containing 38% ds corn starch solids by suspending dry corn starch in reverse osmosis water (R.O.). The pH was adjusted to 5.8, using $SO_2$ or sodium carbonate, as appropriate. To this slurry, 5 LU of SPEZYME® FRED and 0.6 AAU of AmyS S242Q were added. The slurry was liquefied with a HydroHeater Brand steam injection type jet cooker at 108° C. with a residence hold time of 5 minutes. Following this primary liquefaction, the liquefied slurry was flashed to atmospheric pressure and held at 95° C. for 120 minutes or until 10 DE was achieved. The DE development is shown in FIG. 16. The alpha amylase activity was terminated by adjusting the pH to 3.5 with HCl and holding at 95° C. for 20 minutes.

The liquefied starch was cooled to 60° C., and the pH was adjusted to 4.5 using a 20% sodium carbonate solution. The saccharification was done by treating the liquefied starch at pH 4.5 with OPTIMAX™ 4060 brand saccharifying enzyme blend at a dose of 0.16 GAU/g of dry substance. The glucose production over time is shown in Table 6.

TABLE 6

| Saccharifying Time (hours) | % Glucose | % DP2 | % DP3 | % DP4+ |
|---|---|---|---|---|
| 18 | 88.45 | 2.86 | 0.78 | 7.9 |
| 42 | 95.68 | 2.5 | 0.7 | 1.13 |

The final saccharified glucose syrup was tested for sediment by centrifuging 100 ml at 2500 rpm for 10 minutes. The syrup contained less than 1.5% sediment. Two drops of the centrifuge pellet were removed and resuspended in 5 ml with RO water. This solution was cooled in an ice bath to approximately 10° C., and 0.5 ml of a 0.02 N iodine solution was added. The color remained unchanged and was judged to be negative to iodine staining.

All publications and patents mentioned in the above specification are herein incorporated by reference. Various modifications and variations of the described methods and system of the invention will be apparent to those skilled in the art without departing from the scope and spirit of the invention.

Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

SEQUENCE LISTING

```
SEQ ID NOS: 1-15
                              1                                                50
SEQ ID No 1    (1)    -AAPFNGTMMQYFEWYLPDDGTLWTKVANEANNLSSLGITALWLPPAYKG
SEQ ID No 2    (1)    -AAPFNGTMMQYFEWYLPDDGTLWTKVANEANNLSSLGITALWLPPAYKG
SEQ ID No 3    (1)    -AAPFNGTMMQYFEWYLPDDGTLWTKVANEANNLSSLGITALWLPPAYKG
SEQ ID No 4    (1)    -AAPFNGTMMQYFEWYLPDDGTLWTKVANEANNLSSLGITALWLPPAYKG
SEQ ID No 5    (1)    -AAPFNGTMMQYFEWYLPDDGTLWTKVANEANNLSSLGITALWLPPAYKG
SEQ ID No 6    (1)    HHNGTNGTMMQYFEWYLPNDGNHWNRLNSDASNLKSKGITAVWIPPAWKG
SEQ ID No 7    (1)    --ANLNGTLMQYFEWYMPNDGQHWKRLQNDSAYLAEHGITAVWIPPAYKG
SEQ ID No 8    (1)    --ANLNGTLMQYFEWYMPNDGQHWRRLQNDSAYLAEHGITAVWIPPAYKG
SEQ ID No 9    (1)    ----VNGTLMQYFEWYTPNDGQHWKRLQNDAEHLSDIGITAVWIPPAYKG
SEQ ID No 10   (1)    HHNGTNGTMMQYFEWYLPNDGNHWNRLRSDASNLKDKGISAVWIPPAWKG
SEQ ID No 11   (1)    HHNGTNGTMMQYFEWHLPNDGNHWNRLRDDASNLRNRGITAIWIPPAWKG
SEQ ID No 12   (1)    HHNGTNGTMMQYFEWHLPNDGNHWNRLRDDAANLKSKGITAVWIPPAWKG
SEQ ID No 13   (1)    --DGLNGTmmQYYEWHLENDGQHWNRLHDDAAALSDAGITAIWIPPAYKG
SEQ ID No 14   (1)    --DGLNGTMMQYYEWHLENDGQHWNRLHDDAEALSNAGITAIWIPPAYKG
SEQ ID No 15   (1)    -AAPFNGTMMQYFEWYLPDDGTLWTKVANEANNLSSLGITALWLPPAYKG
Consensus      (1)      A  NGTMMQYFEWYLPNDGQHW RL NDA NLSS GITALWIPPAYKG 51                                               100
SEQ ID No 1    (50)   TSRSDVGYGVYDLYDLGEFNQKGTVRTKYGTKAQYLQAIQAAHAAGMQVY
SEQ ID No 2    (50)   TSRSDVGYGVYDLYDLGEFNQKGTVRTKYGTKAQYLQAIQAAHAAGMQVY
SEQ ID No 3    (50)   TSRSDVGYGVYDLYDLGEFNQKGTVRTKYGTKAQYLQAIQAAHAAGMQVY
SEQ ID No 4    (50)   TSRSDVGYGVYDLYDLGEFNQKGTVRTKYGTKAQYLQAIQAAHAAGMQVY
SEQ ID No 5    (50)   TSRSDVGYGVYDLYDLGEFNQKGTVRTKYGTKAQYLQAIQAAHAAGMQVY
SEQ ID No 6    (51)   ASQNDVGYGAYDLYDLGEFNQKGTVRTKYGTRSQLQAAVTSLKNNGIQVY
SEQ ID No 7    (49)   TSQADVGYGAYDLYDLGEFHQKGTVRTKYGTKGELQSAIKSLHSRDINVY
SEQ ID No 8    (49)   TSQADVGYGAYDLYDLGEFHQKGTVRTKYGTKGELQSAIKSLHSRDINVY
SEQ ID No 9    (47)   LSQSDNGYGPYDLYDLGEFQQKGTVRTKYGTKSELQDAIGSLHSRNVQVY
SEQ ID No 10   (51)   ASQNDVGYGAYDLYDLGEFNQKGTIRTKYGTRNQLQAAVNALKSNGIQVY
SEQ ID No 11   (51)   TSQNDVGYGAYDLYDLGEFNQKGTVRTKYGTRSQLESAIHALKNNGVQVY
SEQ ID No 12   (51)   TSQNDVGYGAYDLYDLGEFNQKGTVRTKYGTRSQLQGAVTSLKNNGIQVY
SEQ ID No 13   (49)   NSQADVGYGAYDLYDLGEFNQKGTVRTKYGTKAQLERAIGSLKSNDINVY
SEQ ID No 14   (49)   NSQADVGYGAYDLYDLGEFNQKGTVRTTYGTKAQLERAIGSLKSNDINVY
SEQ ID No 15   (50)   TSRSDVGYGVYDLYDLGEFNQKGTVRTKYGTKAQYLQAIQAAHAAGMQVY
Consensus      (51)   TSQSDVGYGAYDLYDLGEFNQKGTVRTKYGTKAQL  AI ALHA GIQVY 101                                              150
```

-continued

```
SEQ ID No 1    (100) ADVVFDHKGGADGTEWVDAVEVNPSDRNQEISGTYQIQAWTKFDFPGRGN
SEQ ID No 2    (100) ADVVFDHKGGADGTEWVDAVEVNPSDRNQEISGTYQIQAWTKFDFPGRGN
SEQ ID No 3    (100) ADVVFDHKGGADGTEWVDAVEVNPSDRNQEISGTYQIQAWTKFDFPGRGN
SEQ ID No 4    (100) ADVVFDHKGGADGTEWVDAVEVNPSDRNQEISGTYQIQAWTKFDFPGRGN
SEQ ID No 5    (100) ADVVFDHKGGADGTEWVDAVEVNPSDRNQEISGTYQIQAWTKFDFPGRGN
SEQ ID No 6    (101) GDVVMNHKGGADATEMVRAVEVNPNNRNQEVTGEYTIEAWIRFDFPGRGN
SEQ ID No 7    (99)  GDVVINHKGGADATEDVTAVEVDPADRNRVISGEHLIKAWTHFHFPGRGS
SEQ ID No 8    (99)  GDVVINHKGGADATEDVTAVEVDPADRNRVISGEHLIKAWTHFHFPGRGS
SEQ ID No 9    (97)  GDVVLNHKAGADATEDVTAVEVNPANRNQETSEEYQIKAWTDFRFPGRGN
SEQ ID No 10   (101) GDVVMNHKGGADATEMVRAVEVNPNNRNQEVSGEYTIEAWTKFDFPGRGN
SEQ ID No 11   (101) GDVVMNHKGGADATENVLAVEVNPNNRNQEISGDYTIEAWTKFDFPGRGN
SEQ ID No 12   (101) GDVVMNHKGGADGTEMVNAVEVNRSNRNQEISGEYTIEAWTKFDFPGRGN
SEQ ID No 13   (99)  GDVVMNHKMGADFTEAVQAVQVNPTNRWODISGAYTIDAWTGEDFSGRNN
SEQ ID No 14   (99)  GDVVMNHKLGADFTEAVQAVQVNPSNRWQDISGVYTIDAWTGFDFPGRNN
SEQ ID No 15   (100) ADVVFDHKGGADGTEWVDAVEVNPSDRNQEISGTYQIQAWTKFDFPGRGN
Consensus      (101) GDVVMNHKGGADGTE V AVEVNPSDRNQEISG Y I AWTKFDFPGRGN 151                                             200
SEQ ID No 1    (150) TYSSFKWRWYHFDGVDWDESRKLS-RIYKFRGIGKAWDWEVDTENGNYDY
SEQ ID No 2    (150) TYSSFKWRWYHFDGVDWDESRKLS-RIYKFRGIGKAWDWEVDTENGNYDY
SEQ ID No 3    (150) TYSSFKWRWYHFDGVDWDESRKLS-RIYKFRGIGKAWDWEVDTENGNYDY
SEQ ID No 4    (150) TYSSFKWRWYHFDGVDWDESRKLS-RIYKFRGIGKAWDWEVDTENGNYDY
SEQ ID No 5    (150) TYSSFKWRWYEFDGVDWDESRKLS-RIYKFRGIGKAWDWEVDTENGNYDY
SEQ ID No 6    (151) THSSFKWRWYHFDGVDWDQSKRLNNRIYKFRGHGKAWDWEVDTENGNYDY
SEQ ID No 7    (149) TYSDFKWHWYHFDGTDWDESRKLN-RIYKFQG--KAWDWEVSNENGNYDY
SEQ ID No 8    (149) TYSDFKWHWYHFDGTDWDESRKLN-RIYKFQG--KAWDWEVSNENGNYDY
SEQ ID No 9    (147) TYSDFKWHWYHFDGADWDESRKIS-RIFKFRGEGKAWDWEVSSENGNYDY
SEQ ID No 10   (151) THSNFKWRWYHFDGVDWDQSRKLNNRIYKFRGDGKGWDWEVDTENGNYDY
SEQ ID No 11   (151) TYSDFKWRWYHFDGVDWDQSRQFQNRIYKFRGDGKAWDWEVDSENGNYDY
SEQ ID No 12   (151) THSNFKWRWYHFDGTDWDQSRQLQNKIYKFRGTGKAWDWEVDIENGNYDY
SEQ ID No 13   (149) AYSDFKWRWFHFNGVDWDQRYQEN-HIFRFAN--TNWNWRVDEENGNYDY
SEQ ID No 14   (149) AYSDFKWRWFHFNGVDWDQRYQEN-HLFRFAN--TNNNWRVDEENGNYDY
SEQ ID No 15   (150) TYSSFKWRWYHFDGVDWDESRKLS-RIYKFRG--KAWDWEVDTEFGNYDY
Consensus      (151) TYS FKWRWYHFDGVDWDESRKLN RIYKFRG GKAWDWEVDTENGNYDY 201                                             250
SEQ ID No 1    (199) LMYADLDMDHPEVVTELKNWGKWYVNTTNIDGFRLDAVKHIKFSFFPDWL
SEQ ID No 2    (199) LMYADLDMDHPEVVTELKNWGKWYVNTINIDGFRLDAVKHIKFSFFPDWL
SEQ ID No 3    (199) LMYADLDMDHPEVVTELKNWGKWYVNTTNIDGFRLDAVKHIKFAFFPDWL
SEQ ID No 4    (199) EMYADEDMDHPEVVTELKNWGKWYVNTTNIDGFRLDAVKHIKFQFFPDWL
SEQ ID No 5    (199) LMYADLDMDHPEVVTELKNWGKWYVNTTNIDGFRLDAVKHIKFEFFPDWL
SEQ ID No 6    (201) LMYADIDMDHPEVVNELRNWGVWYTNTLGLDGFRIDAVKHIKYSFTRDWI
SEQ ID No 7    (196) LMYADIDYDHPDVAAEIKRWGTWYANELQLDGFRLDAVKHIKFSFLRDWV
SEQ ID No 8    (196) LMYADIDYDHPDVAAETKRWGTWYANELQLDGFRLDAVKHIKFSFLRDWV
```

```
                        -continued
SEQ ID No 9     (196)   LMYADVDYDHPDVVAETKKWGIWYANELSEDGFRIDAAKHIKFSFLRDWV SEQ ID No 10    (201)   LMYADIDMDHPEVVNELRNWGVWYTNTLGLDGFRIDAVKHIKYSFTRDWI SEQ ID No 11    (201)   LMYADVDMDHPEVVNELRRWGEWYTNTLNLDGFRIDAVKHIKYSFTRDWL SEQ ID No 12    (201)   LMYADIDMDHPEVINELRNWGVWYTNTLNLDGFRIDAVKHIKYSYTRDWL SEQ ID No 13    (196)   LLGSNIDFSHPEVQDELKDWGSWFTDELDLDGYRLDAIKHIPFWYTSDWV SEQ ID No 14    (196)   LLGSNIDFSHPEVQEELKDWGSWFTDELDLDGYRLDAIKHIPFWYTSDWV SEQ ID No 15    (197)   LMYADEDMDHPEVVTELKNWGKWYVNTTNIDGFRLDAVKHIKFSFFPDWL Consensus       (201)   LMYADIDMDHPEVV ELKNWG WY NTLNLDGFRLDAVKHIKFSF  DWL 251                                              300
SEQ ID No 1     (249)   SYVRSQTGKPLFTVGEYWSYDINKLHNYITKTNGTMSLFDAPLHNKFYTA SEQ ID No 2     (249)   SYVRSQTGKPLFTVGEYWSYDINKLHNYITKTNGTMSLFDAPLHNKFYTA SEQ ID No 3     (249)   SYVRSQTGKPLFTVGEYWSYDINKLHNYITKTNGTMSLFDAPLHNKFYTA SEQ ID No 4     (249)   SYVRSQTGKPLFTVGEYWSYDINKLHNYITKTNGTMSLFDAPLHNKFYTA SEQ ID No 5     (249)   SYVRSQTGKPLFTVGEYWSYDINKLHNYITKTNGTMSLFDAPLHNKFYTA SEQ ID No 6     (251)   NHVRSATGKNMFAVAEFWKNDLGAIENYLQKTNWNHSVFDVPLHYNLYNA SEQ ID No 7     (246)   NHVREKTGKEMFTVAEYWQNDLGALENYLNKTNENHSVFDVPLHYQFHAA SEQ ID No 8     (246)   NHVREKTGKEMFTVAEYWQNDLGALENYLNKTNENHSVFDVPLHYQFHAA SEQ ID No 9     (246)   QAVRQATGKEMFTVAEYWQNNAGKLENYLNKTSFNQSVFDVPLHENLQAA SEQ ID No 10    (251)   NHVESATGKNMFAVAEFWKNDLGAIENYLNKTNWNHSVFDVPLHYNLYNA SEQ ID No 11    (251)   THVRNATGKEMFAVAEFWKNDLGALENYLNKTNWNHSVFDVPLHYNLYNA SEQ ID No 12    (251)   THVRNTTGKPMFAVAEFWKNDLAAIENYLNKTSWNHSVFDVPLHYNLYNA SEQ ID No 13    (246)   RHQRNEADQDLFVVGEYWKDDVGALEFYLDEMNWEMSLFDVPLNYNFYRA SEQ ID No 14    (246)   RHQRSEADQDLFVVGEYWKDDVGALEFYLDEMNWEMSLFDVPLNYNFYRA SEQ ID No 15    (247)   SYVRSQTGKPLFTVGEYWSYDINKLHNYITKTNGTMSLFDAPLHNKFYTA Consensus       (251)   SHVRS TGK LFTVGEYW  DIGALENYL KTNW MSLFDVPLHYNFY A 301                                              350
SEQ ID No 1     (299)   SKSGGAFDMRTLMTNTLMKDQPTLAVTFVDNHDTEPGQALQSWVDPWFKP SEQ ID No 2     (299)   SKSGGAFDMRTLMTNTLMKDQPTLAVTFVDNHDTEPGQALQSWVDPWFKP SEQ ID No 3     (299)   SKSGGAFDMRTLMTNTLMKDQPTLAVTFVDNHDTEPGQALQSWVDPWFKP SEQ ID No 4     (299)   SKSGGAFDMRTLMTNTLMKDQPTLAVTFVDNHDTEPGQALQSWVDPWFKP SEQ ID No 5     (299)   SKSGGAFDMRTLMTNTLMKDQPTLAVTFVDNHDTEPGQALQSWVDPWFKP SEQ ID No 6     (301)   SKSGGNYDMRNIENGTVVQRHPSHAVTFVDNHDSQPEEALESFVEENFKP SEQ ID No 7     (296)   STQGGGYDMRKLENGTVVSKHPLKSVTFVDNHDTQPGQSLESTVQTWFKP SEQ ID No 8     (296)   STQGGGYDMRKLENGTVVSKHPLKSVTFVDNHDTQPGQSLESTVQTWFKP SEQ ID No 9     (296)   SSQGGGYDMRRLLDGTVVSRHPEKAVTFVENHDTQPGQSLESTVQTWFKP SEQ ID No 10    (301)   SKSGGNYDMRQIENGTVVQRHPMHAVTFVDNHDSQPEEALESFVEEWFKP SEQ ID No 11    (301)   SNSGGNYDMAKLLNGTVVQKHPMHAVTFVDNHDSQPGESLESFVQEWFKP SEQ ID No 12    (301)   SNSGGYFDMRNIENGSVVQKHPIHAVTFVDNHDSQPGEALESFVQSWFKP SEQ ID No 13    (296)   SQQGGSYDMRNILRGSLVEAHPMHAVTFVDNHDTQPGESLESWVADWFKP SEQ ID No 14    (296)   SKQGGSYDMRNILRGSLVEAHPIHAVTFVDNHDTQPGESLESWVADWFKR SEQ ID No 15    (297)   SKSGGAFDMRTLMTNTLMKDQPTLAVTFVDNHDTEPGQALQSWVDPWFKP
```

-continued

```
Consensus      (301)  SKSGGAYDMR LL GTLV  HP  AVTFVDNHDTQPGQALESWVD WFKP 351                                          400
SEQ ID No 1    (349)  LAYAFILTRQEGYPCVFYGDYYGIPQYN---IPSLKSKIDPLLIARRDYA
SEQ ID No 2    (349)  LAYAFILTRQEGYPCVFYGDYYGIPQYN---IPSLKSKIDPLLIARRDYA
SEQ ID No 3    (349)  LAYAFILTRQEGYPCVFYGDYYGIPQYN---IPSLKSKIDPLLIARRDYA
SEQ ID No 4    (349)  LAYAFILTRQEGYPCVFYGDYYGIPQYN---IPSLKSKIDPLLIARRDYA
SEQ ID No 5    (349)  LAYAFILTRQEGYPCVFYGDYYGIPQYN---IPSLKSKIDPLLIARRDYA
SEQ ID No 6    (351)  LAYALTLTREQGYPSVFYGDYYGIPTHG---VPAMRSKIDPILEARQKYA
SEQ ID No 7    (346)  LAYAFILTRESGYPQVFYGDMYGTKGDSQREIPALKHKIEPILKARKQYA
SEQ ID No 8    (346)  LAYAFILTRESGYPQVFYGDMYGTKGDSQREIPALKHKIEPILKARKQYA
SEQ ID No 9    (346)  LAYAFILTRESGYPQVFYGDMYGTKGTSPKEIPSLKDNIEPILKARKEYA
SEQ ID No 10   (351)  LAYALTLTREQGYPSVFYGDYYGIPTHG---VPAMKSKIDPILEARQKYA
SEQ ID No 11   (351)  LAYALILTREQGYPSVFYGDYYGIPTHS---VPAMKAKIDPILEARQNFA
SEQ ID No 12   (351)  LAYALILTREQGYPSVFYGDYYGIPTHG---VPSMKSKIDPLLQARQTYA
SEQ ID No 13   (346)  LAYATILTREGGYPNVEYGDYYGIPNDN---ISAKKDMIDELLDARQNYA
SEQ ID No 14   (346)  LAYATILTREGGYPNVFYGDYYGIPNDN---ISAKKDMIDELLDARQNYA
SEQ ID No 15   (347)  LAYAFILTRQEGYPCVFYGDYYGIPQYN---IPSLKSKIDPLLIARRDYA
Consensus      (351)  LAYAFILTRE GYP VFYGDYYGIPQYN   IPSLKSKIDPLL ARR YA 401                                          450
SEQ ID No 1    (396)  YGTQHDYLDHSDIIGWTREGVTEKPGSGLAALITDGPGGSKWMYVGKQHA
SEQ ID No 2    (396)  YGTQHDYLDHSDIIGWTREGVTEKPGSGLAALITDGPGGSKWMYVGKQHA
SEQ ID No 3    (396)  YGTQHDYLDHSDIIGWTREGVTEKPGSGLAALITDGPGGSKWMYVGKQHA
SEQ ID No 4    (396)  YGTQHDYLDHSDIIGWTREGVTEKPGSGLAALITDGPGGSKWMYVGKQHA
SEQ ID No 5    (396)  YGTQHDYLDHSDIIGWTREGVTEKPGSGLAALITDGPGGSKWMYVGKQHA
SEQ ID No 6    (398)  YGKQNDYLDHHNIIGWTREGNTAHPNSGLATIMSDGAGGSKWMFVGRNKA
SEQ ID No 7    (396)  YGAQHDYFDHHDIVGWTREGDSSVANSGLAALITDGPGGAKRMYVGRQNA
SEQ ID No 8    (396)  YGAQHDYFDHHDIVGWTREGDSSVANSGLAALITDGPGGAKRMYVGRQNA
SEQ ID No 9    (396)  YGPQHDYIDHPDVIGWTREGDSSAAKSGLAALITDGPGGSKRMYAGLKNA
SEQ ID No 10   (398)  YGRQNDYLDHHNIIGWIREGNTAHPNSGLATIMSDGAGGNKWMFVGRNKA
SEQ ID No 11   (398)  YGTQHDYFDHHNIIGWTREGNTTHPNSGLATIMSDGPGGEKWMYVGQNKA
SEQ ID No 12   (398)  YGTQHDYFDHHDIIGWTREGDSSHPNSGLATIMSDGPGGNKWMYVGKHKA
SEQ ID No 13   (393)  YGTQHDYFDHWDVVGWTREGSSSRPNSGLATIMSNGPGGSKWMYVGRQNA
SEQ ID No 14   (393)  YGTQHDYFDHWDIVGWTREGTSSRPNSGLATIMSNGPGGSKWMYVGQQHA
SEQ ID No 15   (394)  YGTQHDYLDHSDIIGWTREGGTEKPGSGLAALITDGPGGSKWMYVGKQHA
Consensus      (401)  YGTQHDYLDH DIIGWTREG TSKPNSGLAALITDGPGGSKWMYVGKQ A 451                                          500
SEQ ID No 1    (446)  GKVFYDLTGNRSDTVTINSDGWGEFKVNGGSVSVWVPRKTTVSTIARPIT
SEQ ID No 2    (446)  CKVFYDLTGNRSDTVTINSDGWGEFKVNGGSVSVWVPRKTT---------
SEQ ID No 3    (446)  GKVFYDLTGNRSDTVTINSDGWGEFKVNGGSVSVWVPRKTTVSTIARPIT
SEQ ID No 4    (446)  GKVFYDLTGNRSDTVTINSDGWGEFKVNGGSVSVWVPRKTTVSTIARPIT
SEQ ID No 5    (446)  GKVFYDLTGNRSDTVTINSDGWGEFKVNGGSVSVWVPRKTTVSTIARPIT
SEQ ID No 6    (448)  GQVWSDITGNRTGTVTINADGWGNFSVNGGSVSIWVNK------------
```

```
SEQ ID No 7    (446)  GETWHDITGNRSEPVVINSEGWGEFHVNGGSVSIYVQR------------
SEQ ID No 8    (446)  GETWHDITGNRSEPVVINSEGWGEFHVNGGSVSIYVQR------------
SEQ ID No 9    (446)  GETWYDITGNRSDTVKIGSDGWGEFHVNDGSVSIYVQK------------
SEQ ID No 10   (448)  GQVWTDITGNRAGTVTINADGWGNFSVNGGSVSIWVNK------------
SEQ ID No 11   (448)  GQVWHDITGNKPGTVTINADGWANFSVNGGSVSIWVKR------------
SEQ ID No 12   (448)  GQVWRDITGNRSGTVTINADGWGNFTVNGGAVSVWVKQ------------
SEQ ID No 13   (443)  GQTWTDLTGNNGASVTINGDGWGEFFTNGGSVSVYVNQ------------
SEQ ID No 14   (443)  GQTWTDLTGNHAASVTINGDGWGEFFTNGGSVSVYVNQ------------
SEQ ID No 15   (444)  GKVFYDLTGNRSDTVTINSDGWGEFKVNGGSVSVWVPRKTTVS-------

Consensus      (451)  G VWYDLTGNRSDTVTINSDGWGEF VNGGSVSVWV R 501                520
SEQ ID No 1    (496)  TRPWTGEFVRWTEPRLVAWP
SEQ ID No 2    (487)  --------------------
SEQ ID No 3    (496)  TRPWTGEFVRWTEPRLVAWP
SEQ ID No 4    (496)  TRPWTGEFVRWTEPRLVAWP
SEQ ID No 5    (496)  TRPWTGEFVRWTEPRLVAWP
SEQ ID No 6    (486)  --------------------
SEQ ID No 7    (484)  --------------------
SEQ ID No 8    (484)  --------------------
SEQ ID No 9    (484)  --------------------
SEQ ID No 10   (486)  --------------------
SEQ ID No 11   (486)  --------------------
SEQ ID No 12   (486)  --------------------
SEQ ID No 13   (481)  --------------------
SEQ ID No 14   (481)  --------------------
SEQ ID No 15   (487)  --------------------

Consensus      (501)

SEQ ID NO: 16: Truncated Geobacillus stearothermophilus α-amylase (AmyS,
a/k/a "Ethyl3") protein sequence. The signal sequence is shown in bold.
     1    MLTFHRIIRK GWMFLLAFLL TASLFCPTGQ HAKAAAPFNG TMMQYFEWYL

51    PDDGTLWTKV ANEANNLSSL GITALWLPPA YKGTSRSDVG YGVYDLYDLG

101    EFNQKGTVRT KYGTKAQYLQ AIQAAHAAGM QVYADVVFDH KGGADGTEWV

151    DAVEVNPSDR NQEISGTYQI QAWTKFDFPG RGNTYSSFKW RWYHFDGVDW

201    DESRKLSRIY KFIGKAWDWE VDTENGNYDY LMYADLDMDH PEVVTELKNW

251    GKWYVNTTNI DGFRLDAVKH IKFSFFPDWL SYVRSQTGKP LFTVGEYWSY

301    DINKLHNYIT KTNGTMSLFD APLHNKFYTA SKSGGAFDMR TLMTNTLMKD

351    QPTLAVTFVD NHDTEPGQAL QSWVDPWFKP LAYAFILTRQ EGYPCVFYGD

401    YYGIPQYNIP SLKSKIDPLL IARRDYAYGT QHDYLDHSDI IGWTREGVTE

451    KPGSGLAALI TDGPGGSKWM YVGKQHAGKV FYDLTGNRSD TVTINSDGWG

501    EFKVNGGSVS VWVPRKTT
```

SEQ ID NO: 17: S242 primer for mutagenesis:
S242 F: 5' [Phos]GTCAAGCATATTAAGTTCNNSTTTTTTCCTGATTGGTTG 3'

SEQ ID NO: 18: S242 primer for mutagenesis:
S242 R: 5' [Phos]CAACCAATCAGGAAAAAASNNGAACTTAATATGCTTGAC 3'

SEQ ID NO: 19: Mature protein sequence of Buttiauxella BP-17 phytase
NDTPASGYQV EKVVILSRHG VRAPTKMTQT MRDVTPNTWP EWPVKLGYIT

PRGEHLISLM GGFYRQKFQQ QGILSQGSCP TPNSIYVWAD VDQRTLKTGE

AFLAGLAPQC GLTIHHQQNL EKADPLFHPV KAGTCSMDKT QVQQAVEKEA

QTPIDNLNQH YIPFLALMNT TLNFSTSAWC QKHSADKSCD LGLSMPSKLS

IKDNGNKVAL DGAIGLSSTL AEIFLLEYAQ GMPQAAWGNI HSEQEWASLL

KLHNVQFDLM ARTPYIARHN GTPLLQAISN ALNPNATESK LPDISPDNKI

LFIAGHDTNI ANIAGMLNMR WTLPGQPDNT PPGGALVFER LADKSGKQYV

SVSMVYQTLE QLRSQTPLSL NQPAGSVQLK IPGCNDQTAE GYCPLSTFTR

VVSQSVEPGC QLQ

SEQ ID NO: 20: SPEZYME ® FRED α-amylase amino acid sequence.
```
  1    ANLNGTLMQY FEWYTPNDGQ HWKRLQNDSA YLAEHGITAV WIPPAYKGTS

51    QADVGYGAYD LYDLGEFHQK GTVRTKYGTK GELQSAIKSL HSRDINVYGD

101    VVINHKGGAD ATEDVTAVEV DPADRNRVIS GEYLIKAWTH FHFPGRGSTY

151    SDFKWHWYHF DGTDWDESRK LNRIYKFQGK AWDWEVSSEN GNYDYLMYAD

201    IDYDHPDVVA EIKRWGTWYA NELQLDGFRL DAVKHIKFSF LRDWVNHVRE

251    KTGKEMFTVA EYWQNDLGAL ENYLNKTNFN HSVFDVPLHY QFHAASTQGG

301    GYDMRKLLNG TVVSKHPLKS VTFVDNHDTQ PGQSLESTVQ TWFKPLAYAF

351    ILTRESGYPQ VFYGDMYGTK GDSQREIPAL KHKIEPILKA RKQYAYGAQH

401    DYFDHHDIVG WTREGDSSVA NSGLAALITD GPGGAKRMYV GRQNAGETWH

451    DITGNRSEPV VINSEGWGEF HVNGGSVSIY VQR
```

---

What is claimed is:

1. An alpha-amylase blend, comprising:
   (i) a *B. stearothermophilus* alpha-amylase (AmyS) comprising the polypeptide sequence of SEQ ID NO: 2, wherein the amino acid at position S242 is substituted, using the amino acid number system shown in SEQ ID NO: 2; and
   (ii) a *B. licheniformis* alpha-amylase.

2. The alpha-amylase blend of claim 1, further comprising a phytase.

3. The alpha-amylase blend of claim 1, wherein the blend comprises a weight ratio of about 40% of the AmyS with the S242 substitution and about 60% *B. licheniformis* alpha-amylase.

4. The alpha-amylase blend of claim 1, wherein the weight ratio of AmyS with the S242 substitution to *B. licheniformis* alpha-amylase is 10:90.

5. The alpha-amylase blend of claim 1, further comprising an activity ratio of from about 1400 AAU/g to about 14000 AAU/g of the AmyS with the S242 substitution, and from about 8000 LU/g to about 19000 LU/g *B. licheniformis* alpha-amylase.

6. The alpha-amylase blend of claim 1, wherein the AmyS comprises the polypeptide sequence of SEQ ID NO: 1 or SEQ ID NO: 2.

7. The alpha-amylase blend of claim 1, wherein the S242 substitution is an S242A, S242E, S242Q, S242F, S242H, or S242N substitution.

8. The alpha-amylase blend of claim 1, wherein the AmyS with the substitution at position S242 has a higher thermostability between about 80° C. and about 95° C. compared to an AmyS without the S242 substitution.

9. The alpha-amylase blend of claim 1, wherein the AmyS comprises an amino acid sequence having at least 90%, 95%, 98%, or 99% sequence identity to the AmyS of SEQ ID NO: 1, and wherein the AmyS has alpha-amylase activity.

10. The alpha-amylase blend of claim 1, wherein the *B. licheniformis* alpha-amylase comprises a purified wild-type enzyme.

11. The alpha-amylase blend of claim 1, wherein the *B. licheniformis* alpha-amylase comprises one or more amino acid substitutions of the wild-type sequence selected from the group consisting of M15T, H133Y, N188S, and A209V.

12. The alpha-amylase blend of claim 1, wherein the *B. licheniformis* alpha-amylase comprises the amino acid sequence shown in SEQ ID NO: 20.

13. The alpha-amylase blend of claim 1, wherein the *B. licheniformis* alpha-amylase comprises an amino acid sequence having at least 90%, 95%, 96%, 97% 98%, or 99% sequence identity to SEQ ID NO: 20.

* * * * *

SEQUENCE LISTING

<160> NUMBER OF SEQ IDS: 20

<210> SEQ ID NO 1
<211> LENGTH: 515
<212> TYPE: PRT
<213> ORGANISM: Artificial Sequence
<220> FEATURE:
<223> OTHER INFORMATION: Chemically synthesized AmyS sequence

<400> SEQUENCE: 1

Ala Ala Pro Phe Asn Gly Thr Met Met Gln Tyr Phe Glu Trp Tyr Leu
1               5                  10                  15

Pro Asp Asp Gly Thr Leu Trp Thr Lys Val Ala Asn Glu Ala Asn Asn
            20                  25                  30

Leu Ser Ser Leu Gly Ile Thr Ala Leu Trp Leu Pro Pro Ala Tyr Lys
        35                  40                  45

Gly Thr Ser Arg Ser Asp Val Gly Tyr Gly Val Tyr Asp Leu Tyr Asp
    50                  55                  60

Leu Gly Glu Phe Asn Gln Lys Gly Thr Val Arg Thr Lys Tyr Gly Thr
65                  70                  75                  80

Lys Ala Gln Tyr Leu Gln Ala Ile Gln Ala Ala His Ala Ala Gly Met

-continued

```
                85                  90                  95
Gln Val Tyr Ala Asp Val Val Phe Asp His Lys Gly Ala Asp Gly
                100                 105                 110

Thr Glu Trp Val Asp Ala Val Glu Val Asn Pro Ser Asp Arg Asn Gln
                115                 120                 125

Glu Ile Ser Gly Thr Tyr Gln Ile Gln Ala Trp Thr Lys Phe Asp Phe
                130                 135                 140

Pro Gly Arg Gly Asn Thr Tyr Ser Ser Phe Lys Trp Arg Trp Tyr His
145                 150                 155                 160

Phe Asp Gly Val Asp Trp Asp Glu Ser Arg Lys Leu Ser Arg Ile Tyr
                165                 170                 175

Lys Phe Arg Gly Ile Gly Lys Ala Trp Asp Trp Glu Val Asp Thr Glu
                180                 185                 190

Asn Gly Asn Tyr Asp Tyr Leu Met Tyr Ala Asp Leu Asp Met Asp His
                195                 200                 205

Pro Glu Val Val Thr Glu Leu Lys Asn Trp Gly Lys Trp Tyr Val Asn
210                 215                 220

Thr Thr Asn Ile Asp Gly Phe Arg Leu Asp Ala Val Lys His Ile Lys
225                 230                 235                 240

Phe Ser Phe Phe Pro Asp Trp Leu Ser Tyr Val Arg Ser Gln Thr Gly
                245                 250                 255

Lys Pro Leu Phe Thr Val Gly Glu Tyr Trp Ser Tyr Asp Ile Asn Lys
                260                 265                 270

Leu His Asn Tyr Ile Thr Lys Thr Asn Gly Thr Met Ser Leu Phe Asp
                275                 280                 285

Ala Pro Leu His Asn Lys Phe Tyr Thr Ala Ser Lys Ser Gly Gly Ala
                290                 295                 300

Phe Asp Met Arg Thr Leu Met Thr Asn Thr Leu Met Lys Asp Gln Pro
305                 310                 315                 320

Thr Leu Ala Val Thr Phe Val Asp Asn His Asp Thr Glu Pro Gly Gln
                325                 330                 335

Ala Leu Gln Ser Trp Val Asp Pro Trp Phe Lys Pro Leu Ala Tyr Ala
                340                 345                 350

Phe Ile Leu Thr Arg Gln Glu Gly Tyr Pro Cys Val Phe Tyr Gly Asp
                355                 360                 365

Tyr Tyr Gly Ile Pro Gln Tyr Asn Ile Pro Ser Leu Lys Ser Lys Ile
                370                 375                 380

Asp Pro Leu Leu Ile Ala Arg Arg Asp Tyr Ala Tyr Gly Thr Gln His
385                 390                 395                 400

Asp Tyr Leu Asp His Ser Asp Ile Ile Gly Trp Thr Arg Glu Gly Val
                405                 410                 415

Thr Glu Lys Pro Gly Ser Gly Leu Ala Ala Leu Ile Thr Asp Gly Pro
                420                 425                 430

Gly Gly Ser Lys Trp Met Tyr Val Gly Lys Gln His Ala Gly Lys Val
                435                 440                 445

Phe Tyr Asp Leu Thr Gly Asn Arg Ser Asp Thr Val Thr Ile Asn Ser
450                 455                 460

Asp Gly Trp Gly Glu Phe Lys Val Asn Gly Gly Ser Val Ser Val Trp
465                 470                 475                 480

Val Pro Arg Lys Thr Thr Val Ser Thr Ile Ala Arg Pro Ile Thr Thr
                485                 490                 495

Arg Pro Trp Thr Gly Glu Phe Val Arg Trp Thr Glu Pro Arg Leu Val
                500                 505                 510
```

```
Ala Trp Pro
        515

<210> SEQ ID NO 2
<211> LENGTH: 486
<212> TYPE: PRT
<213> ORGANISM: Artificial Sequence
<220> FEATURE:
<223> OTHER INFORMATION: Chemically synthesized AmyS sequence

<400> SEQUENCE: 2

Ala Ala Pro Phe Asn Gly Thr Met Met Gln Tyr Phe Glu Trp Tyr Leu
1               5                   10                  15

Pro Asp Asp Gly Thr Leu Trp Thr Lys Val Ala Asn Glu Ala Asn Asn
            20                  25                  30

Leu Ser Ser Leu Gly Ile Thr Ala Leu Trp Leu Pro Pro Ala Tyr Lys
        35                  40                  45

Gly Thr Ser Arg Ser Asp Val Gly Tyr Gly Val Tyr Asp Leu Tyr Asp
    50                  55                  60

Leu Gly Glu Phe Asn Gln Lys Gly Thr Val Arg Thr Lys Tyr Gly Thr
65                  70                  75                  80

Lys Ala Gln Tyr Leu Gln Ala Ile Gln Ala His Ala Ala Gly Met
                85                  90                  95

Gln Val Tyr Ala Asp Val Val Phe Asp His Lys Gly Ala Asp Gly
                100                 105                 110

Thr Glu Trp Val Asp Ala Val Glu Val Asn Pro Ser Asp Arg Asn Gln
            115                 120                 125

Glu Ile Ser Gly Thr Tyr Gln Ile Gln Ala Trp Thr Lys Phe Asp Phe
130                 135                 140

Pro Gly Arg Gly Asn Thr Tyr Ser Ser Phe Lys Trp Arg Trp Tyr His
145                 150                 155                 160

Phe Asp Gly Val Asp Trp Asp Glu Ser Arg Lys Leu Ser Arg Ile Tyr
                165                 170                 175

Lys Phe Arg Gly Ile Gly Lys Ala Trp Asp Trp Glu Val Asp Thr Glu
            180                 185                 190

Asn Gly Asn Tyr Asp Tyr Leu Met Tyr Ala Asp Leu Asp Met Asp His
        195                 200                 205

Pro Glu Val Val Thr Glu Leu Lys Asn Trp Gly Lys Trp Tyr Val Asn
    210                 215                 220

Thr Thr Asn Ile Asp Gly Phe Arg Leu Asp Ala Val Lys His Ile Lys
225                 230                 235                 240

Phe Ser Phe Phe Pro Asp Trp Leu Ser Tyr Val Arg Ser Gln Thr Gly
                245                 250                 255

Lys Pro Leu Phe Thr Val Gly Glu Tyr Trp Ser Tyr Asp Ile Asn Lys
            260                 265                 270

Leu His Asn Tyr Ile Thr Lys Thr Asn Gly Thr Met Ser Leu Phe Asp
        275                 280                 285

Ala Pro Leu His Asn Lys Phe Tyr Thr Ala Ser Lys Ser Gly Gly Ala
    290                 295                 300

Phe Asp Met Arg Thr Leu Met Thr Asn Thr Leu Met Lys Asp Gln Pro
305                 310                 315                 320

Thr Leu Ala Val Thr Phe Val Asp Asn His Asp Thr Glu Pro Gly Gln
                325                 330                 335

Ala Leu Gln Ser Trp Val Asp Pro Trp Phe Lys Pro Leu Ala Tyr Ala
            340                 345                 350

Phe Ile Leu Thr Arg Gln Glu Gly Tyr Pro Cys Val Phe Tyr Gly Asp
```

```
                355                 360                 365
Tyr Tyr Gly Ile Pro Gln Tyr Asn Ile Pro Ser Leu Lys Ser Lys Ile
370                 375                 380

Asp Pro Leu Leu Ile Ala Arg Arg Asp Tyr Ala Tyr Gly Thr Gln His
385                 390                 395                 400

Asp Tyr Leu Asp His Ser Asp Ile Ile Gly Trp Thr Arg Glu Gly Val
                405                 410                 415

Thr Glu Lys Pro Gly Ser Gly Leu Ala Ala Leu Ile Thr Asp Gly Pro
                420                 425                 430

Gly Gly Ser Lys Trp Met Tyr Val Gly Lys Gln His Ala Gly Lys Val
                435                 440                 445

Phe Tyr Asp Leu Thr Gly Asn Arg Ser Asp Thr Val Thr Ile Asn Ser
                450                 455                 460

Asp Gly Trp Gly Glu Phe Lys Val Asn Gly Gly Ser Val Ser Val Trp
465                 470                 475                 480

Val Pro Arg Lys Thr Thr
                485

<210> SEQ ID NO 3
<211> LENGTH: 515
<212> TYPE: PRT
<213> ORGANISM: Artificial Sequence
<220> FEATURE:
<223> OTHER INFORMATION: Chemically synthesized AmyS sequence

<400> SEQUENCE: 3

Ala Ala Pro Phe Asn Gly Thr Met Met Gln Tyr Phe Glu Trp Tyr Leu
1               5                   10                  15

Pro Asp Asp Gly Thr Leu Trp Thr Lys Val Ala Asn Glu Ala Asn Asn
                20                  25                  30

Leu Ser Ser Leu Gly Ile Thr Ala Leu Trp Leu Pro Pro Ala Tyr Lys
            35                  40                  45

Gly Thr Ser Arg Ser Asp Val Gly Tyr Gly Val Tyr Asp Leu Tyr Asp
        50                  55                  60

Leu Gly Glu Phe Asn Gln Lys Gly Thr Val Arg Thr Lys Tyr Gly Thr
65                  70                  75                  80

Lys Ala Gln Tyr Leu Gln Ala Ile Gln Ala Ala His Ala Ala Gly Met
                85                  90                  95

Gln Val Tyr Ala Asp Val Val Phe Asp His Lys Gly Gly Ala Asp Gly
                100                 105                 110

Thr Glu Trp Val Asp Ala Val Glu Val Asn Pro Ser Asp Arg Asn Gln
            115                 120                 125

Glu Ile Ser Gly Thr Tyr Gln Ile Gln Ala Trp Thr Lys Phe Asp Phe
        130                 135                 140

Pro Gly Arg Gly Asn Thr Tyr Ser Ser Phe Lys Trp Arg Trp Tyr His
145                 150                 155                 160

Phe Asp Gly Val Asp Trp Asp Glu Ser Arg Lys Leu Ser Arg Ile Tyr
                165                 170                 175

Lys Phe Arg Gly Ile Gly Lys Ala Trp Asp Trp Glu Val Asp Thr Glu
                180                 185                 190

Asn Gly Asn Tyr Asp Tyr Leu Met Tyr Ala Asp Leu Asp Met Asp His
            195                 200                 205

Pro Glu Val Val Thr Glu Leu Lys Asn Trp Gly Lys Trp Tyr Val Asn
        210                 215                 220

Thr Thr Asn Ile Asp Gly Phe Arg Leu Asp Ala Val Lys His Ile Lys
225                 230                 235                 240
```

-continued

Phe Ala Phe Phe Pro Asp Trp Leu Ser Tyr Val Arg Ser Gln Thr Gly
                245                 250                 255

Lys Pro Leu Phe Thr Val Gly Glu Tyr Trp Ser Tyr Asp Ile Asn Lys
            260                 265                 270

Leu His Asn Tyr Ile Thr Lys Thr Asn Gly Thr Met Ser Leu Phe Asp
        275                 280                 285

Ala Pro Leu His Asn Lys Phe Tyr Thr Ala Ser Lys Ser Gly Gly Ala
    290                 295                 300

Phe Asp Met Arg Thr Leu Met Thr Asn Thr Leu Met Lys Asp Gln Pro
305                 310                 315                 320

Thr Leu Ala Val Thr Phe Val Asp Asn His Asp Thr Glu Pro Gly Gln
                325                 330                 335

Ala Leu Gln Ser Trp Val Asp Pro Trp Phe Lys Pro Leu Ala Tyr Ala
            340                 345                 350

Phe Ile Leu Thr Arg Gln Glu Gly Tyr Pro Cys Val Phe Tyr Gly Asp
        355                 360                 365

Tyr Tyr Gly Ile Pro Gln Tyr Asn Ile Pro Ser Leu Lys Ser Lys Ile
    370                 375                 380

Asp Pro Leu Leu Ile Ala Arg Arg Asp Tyr Ala Tyr Gly Thr Gln His
385                 390                 395                 400

Asp Tyr Leu Asp His Ser Asp Ile Ile Gly Trp Thr Arg Glu Gly Val
                405                 410                 415

Thr Glu Lys Pro Gly Ser Gly Leu Ala Ala Leu Ile Thr Asp Gly Pro
            420                 425                 430

Gly Gly Ser Lys Trp Met Tyr Val Gly Lys Gln His Ala Gly Lys Val
        435                 440                 445

Phe Tyr Asp Leu Thr Gly Asn Arg Ser Asp Thr Val Thr Ile Asn Ser
    450                 455                 460

Asp Gly Trp Gly Glu Phe Lys Val Asn Gly Gly Ser Val Ser Val Trp
465                 470                 475                 480

Val Pro Arg Lys Thr Thr Val Ser Thr Ile Ala Arg Pro Ile Thr Thr
                485                 490                 495

Arg Pro Trp Thr Gly Glu Phe Val Arg Trp Thr Glu Pro Arg Leu Val
            500                 505                 510

Ala Trp Pro
        515

<210> SEQ ID NO 4
<211> LENGTH: 515
<212> TYPE: PRT
<213> ORGANISM: Artificial Sequence
<220> FEATURE:
<223> OTHER INFORMATION: Chemically synthesized AmyS sequence

<400> SEQUENCE: 4

Ala Ala Pro Phe Asn Gly Thr Met Met Gln Tyr Phe Glu Trp Tyr Leu
1               5                   10                  15

Pro Asp Asp Gly Thr Leu Trp Thr Lys Val Ala Asn Glu Ala Asn Asn
            20                  25                  30

Leu Ser Ser Leu Gly Ile Thr Ala Leu Trp Leu Pro Pro Ala Tyr Lys
        35                  40                  45

Gly Thr Ser Arg Ser Asp Val Gly Tyr Gly Val Tyr Asp Leu Tyr Asp
    50                  55                  60

Leu Gly Glu Phe Asn Gln Lys Gly Thr Val Arg Thr Lys Tyr Gly Thr
65                  70                  75                  80

-continued

```
Lys Ala Gln Tyr Leu Gln Ala Ile Gln Ala Ala His Ala Ala Gly Met
                 85                  90                  95
Gln Val Tyr Ala Asp Val Val Phe Asp His Lys Gly Gly Ala Asp Gly
            100                 105                 110
Thr Glu Trp Val Asp Ala Val Glu Val Asn Pro Ser Asp Arg Asn Gln
        115                 120                 125
Glu Ile Ser Gly Thr Tyr Gln Ile Gln Ala Trp Thr Lys Phe Asp Phe
    130                 135                 140
Pro Gly Arg Gly Asn Thr Tyr Ser Ser Phe Lys Trp Arg Trp Tyr His
145                 150                 155                 160
Phe Asp Gly Val Asp Trp Asp Glu Ser Arg Lys Leu Ser Arg Ile Tyr
                165                 170                 175
Lys Phe Arg Gly Ile Gly Lys Ala Trp Asp Trp Glu Val Asp Thr Glu
            180                 185                 190
Asn Gly Asn Tyr Asp Tyr Leu Met Tyr Ala Asp Leu Asp Met Asp His
        195                 200                 205
Pro Glu Val Val Thr Glu Leu Lys Asn Trp Gly Lys Trp Tyr Val Asn
    210                 215                 220
Thr Thr Asn Ile Asp Gly Phe Arg Leu Asp Ala Val Lys His Ile Lys
225                 230                 235                 240
Phe Gln Phe Phe Pro Asp Trp Leu Ser Tyr Val Arg Ser Gln Thr Gly
                245                 250                 255
Lys Pro Leu Phe Thr Val Gly Glu Tyr Trp Ser Tyr Asp Ile Asn Lys
            260                 265                 270
Leu His Asn Tyr Ile Thr Lys Thr Asn Gly Thr Met Ser Leu Phe Asp
        275                 280                 285
Ala Pro Leu His Asn Lys Phe Tyr Thr Ala Ser Lys Ser Gly Gly Ala
    290                 295                 300
Phe Asp Met Arg Thr Leu Met Thr Asn Thr Leu Met Lys Asp Gln Pro
305                 310                 315                 320
Thr Leu Ala Val Thr Phe Val Asp Asn His Asp Thr Glu Pro Gly Gln
                325                 330                 335
Ala Leu Gln Ser Trp Val Asp Pro Trp Phe Lys Pro Leu Ala Tyr Ala
            340                 345                 350
Phe Ile Leu Thr Arg Gln Glu Gly Tyr Pro Cys Val Phe Tyr Gly Asp
        355                 360                 365
Tyr Tyr Gly Ile Pro Gln Tyr Asn Ile Pro Ser Leu Lys Ser Lys Ile
    370                 375                 380
Asp Pro Leu Leu Ile Ala Arg Arg Asp Tyr Ala Tyr Gly Thr Gln His
385                 390                 395                 400
Asp Tyr Leu Asp His Ser Asp Ile Ile Gly Trp Thr Arg Glu Gly Val
                405                 410                 415
Thr Glu Lys Pro Gly Ser Gly Leu Ala Ala Leu Ile Thr Asp Gly Pro
            420                 425                 430
Gly Gly Ser Lys Trp Met Tyr Val Gly Lys Gln His Ala Gly Lys Val
        435                 440                 445
Phe Tyr Asp Leu Thr Gly Asn Arg Ser Asp Thr Val Thr Ile Asn Ser
    450                 455                 460
Asp Gly Trp Gly Glu Phe Lys Val Asn Gly Gly Ser Val Ser Val Trp
465                 470                 475                 480
Val Pro Arg Lys Thr Thr Val Ser Thr Ile Ala Arg Pro Ile Thr Thr
                485                 490                 495
Arg Pro Trp Thr Gly Glu Phe Val Arg Trp Thr Glu Pro Arg Leu Val
            500                 505                 510
```

Ala Trp Pro
        515

<210> SEQ ID NO 5
<211> LENGTH: 515
<212> TYPE: PRT
<213> ORGANISM: Artificial Sequence
<220> FEATURE:
<223> OTHER INFORMATION: Chemically synthesized AmyS sequence

<400> SEQUENCE: 5

Ala Ala Pro Phe Asn Gly Thr Met Met Gln Tyr Phe Glu Trp Tyr Leu
1               5                   10                  15

Pro Asp Asp Gly Thr Leu Trp Thr Lys Val Ala Asn Glu Ala Asn Asn
            20                  25                  30

Leu Ser Ser Leu Gly Ile Thr Ala Leu Trp Leu Pro Pro Ala Tyr Lys
        35                  40                  45

Gly Thr Ser Arg Ser Asp Val Gly Tyr Gly Val Tyr Asp Leu Tyr Asp
    50                  55                  60

Leu Gly Glu Phe Asn Gln Lys Gly Thr Val Arg Thr Lys Tyr Gly Thr
65                  70                  75                  80

Lys Ala Gln Tyr Leu Gln Ala Ile Gln Ala Ala His Ala Ala Gly Met
                85                  90                  95

Gln Val Tyr Ala Asp Val Val Phe Asp His Lys Gly Gly Ala Asp Gly
            100                 105                 110

Thr Glu Trp Val Asp Ala Val Glu Val Asn Pro Ser Asp Arg Asn Gln
        115                 120                 125

Glu Ile Ser Gly Thr Tyr Gln Ile Gln Ala Trp Thr Lys Phe Asp Phe
    130                 135                 140

Pro Gly Arg Gly Asn Thr Tyr Ser Ser Phe Lys Trp Arg Trp Tyr His
145                 150                 155                 160

Phe Asp Gly Val Asp Trp Asp Glu Ser Arg Lys Leu Ser Arg Ile Tyr
                165                 170                 175

Lys Phe Arg Gly Ile Gly Lys Ala Trp Asp Trp Glu Val Asp Thr Glu
            180                 185                 190

Asn Gly Asn Tyr Asp Tyr Leu Met Tyr Ala Asp Leu Asp Met Asp His
        195                 200                 205

Pro Glu Val Val Thr Glu Leu Lys Asn Trp Gly Lys Trp Tyr Val Asn
    210                 215                 220

Thr Thr Asn Ile Asp Gly Phe Arg Leu Asp Ala Val Lys His Ile Lys
225                 230                 235                 240

Phe Glu Phe Phe Pro Asp Trp Leu Ser Tyr Val Arg Ser Gln Thr Gly
                245                 250                 255

Lys Pro Leu Phe Thr Val Gly Glu Tyr Trp Ser Tyr Asp Ile Asn Lys
            260                 265                 270

Leu His Asn Tyr Ile Thr Lys Thr Asn Gly Thr Met Ser Leu Phe Asp
        275                 280                 285

Ala Pro Leu His Asn Lys Phe Tyr Thr Ala Ser Lys Ser Gly Gly Ala
    290                 295                 300

Phe Asp Met Arg Thr Leu Met Thr Asn Thr Leu Met Lys Asp Gln Pro
305                 310                 315                 320

Thr Leu Ala Val Thr Phe Val Asp Asn His Asp Thr Glu Pro Gly Gln
                325                 330                 335

Ala Leu Gln Ser Trp Val Asp Pro Trp Phe Lys Pro Leu Ala Tyr Ala
            340                 345                 350

```
Phe Ile Leu Thr Arg Gln Glu Gly Tyr Pro Cys Val Phe Tyr Gly Asp
            355                 360                 365

Tyr Tyr Gly Ile Pro Gln Tyr Asn Ile Pro Ser Leu Lys Ser Lys Ile
370                 375                 380

Asp Pro Leu Leu Ile Ala Arg Arg Asp Tyr Ala Tyr Gly Thr Gln His
385                 390                 395                 400

Asp Tyr Leu Asp His Ser Asp Ile Ile Gly Trp Thr Arg Glu Gly Val
            405                 410                 415

Thr Glu Lys Pro Gly Ser Gly Leu Ala Ala Leu Ile Thr Asp Gly Pro
            420                 425                 430

Gly Gly Ser Lys Trp Met Tyr Val Gly Lys Gln His Ala Gly Lys Val
            435                 440                 445

Phe Tyr Asp Leu Thr Gly Asn Arg Ser Asp Thr Val Thr Ile Asn Ser
450                 455                 460

Asp Gly Trp Gly Glu Phe Lys Val Asn Gly Gly Ser Val Ser Val Trp
465                 470                 475                 480

Val Pro Arg Lys Thr Thr Val Ser Thr Ile Ala Arg Pro Ile Thr Thr
            485                 490                 495

Arg Pro Trp Thr Gly Glu Phe Val Arg Trp Thr Glu Pro Arg Leu Val
            500                 505                 510

Ala Trp Pro
        515

<210> SEQ ID NO 6
<211> LENGTH: 485
<212> TYPE: PRT
<213> ORGANISM: Artificial Sequence
<220> FEATURE:
<223> OTHER INFORMATION: Chemically synthesized AmyS sequence

<400> SEQUENCE: 6

His His Asn Gly Thr Asn Gly Thr Met Met Gln Tyr Phe Glu Trp Tyr
1               5                   10                  15

Leu Pro Asn Asp Gly Asn His Trp Asn Arg Leu Asn Ser Asp Ala Ser
            20                  25                  30

Asn Leu Lys Ser Lys Gly Ile Thr Ala Val Trp Ile Pro Pro Ala Trp
        35                  40                  45

Lys Gly Ala Ser Gln Asn Asp Val Gly Tyr Gly Ala Tyr Asp Leu Tyr
50                  55                  60

Asp Leu Gly Glu Phe Asn Gln Lys Gly Thr Val Arg Thr Lys Tyr Gly
65                  70                  75                  80

Thr Arg Ser Gln Leu Gln Ala Ala Val Thr Ser Leu Lys Asn Asn Gly
            85                  90                  95

Ile Gln Val Tyr Gly Asp Val Val Met Asn His Lys Gly Gly Ala Asp
        100                 105                 110

Ala Thr Glu Met Val Arg Ala Val Glu Val Asn Pro Asn Asn Arg Asn
    115                 120                 125

Gln Glu Val Thr Gly Glu Tyr Thr Ile Glu Ala Trp Thr Arg Phe Asp
130                 135                 140

Phe Pro Gly Arg Gly Asn Thr His Ser Ser Phe Lys Trp Arg Trp Tyr
145                 150                 155                 160

His Phe Asp Gly Val Asp Trp Asp Gln Ser Arg Arg Leu Asn Asn Arg
                165                 170                 175

Ile Tyr Lys Phe Arg Gly His Gly Lys Ala Trp Asp Trp Glu Val Asp
            180                 185                 190

Thr Glu Asn Gly Asn Tyr Asp Tyr Leu Met Tyr Ala Asp Ile Asp Met
```

```
                195                 200                 205
Asp His Pro Glu Val Val Asn Glu Leu Arg Asn Trp Gly Val Trp Tyr
    210                 215                 220

Thr Asn Thr Leu Gly Leu Asp Gly Phe Arg Ile Asp Ala Val Lys His
225                 230                 235                 240

Ile Lys Tyr Ser Phe Thr Arg Asp Trp Ile Asn His Val Arg Ser Ala
                245                 250                 255

Thr Gly Lys Asn Met Phe Ala Val Ala Glu Phe Trp Lys Asn Asp Leu
            260                 265                 270

Gly Ala Ile Glu Asn Tyr Leu Gln Lys Thr Asn Trp Asn His Ser Val
        275                 280                 285

Phe Asp Val Pro Leu His Tyr Asn Leu Tyr Asn Ala Ser Lys Ser Gly
    290                 295                 300

Gly Asn Tyr Asp Met Arg Asn Ile Phe Asn Gly Thr Val Val Gln Arg
305                 310                 315                 320

His Pro Ser His Ala Val Thr Phe Val Asp Asn His Asp Ser Gln Pro
                325                 330                 335

Glu Glu Ala Leu Glu Ser Phe Val Glu Trp Phe Lys Pro Leu Ala
            340                 345                 350

Tyr Ala Leu Thr Leu Thr Arg Glu Gln Gly Tyr Pro Ser Val Phe Tyr
        355                 360                 365

Gly Asp Tyr Tyr Gly Ile Pro Thr His Gly Val Pro Ala Met Arg Ser
    370                 375                 380

Lys Ile Asp Pro Ile Leu Glu Ala Arg Gln Lys Tyr Ala Tyr Gly Lys
385                 390                 395                 400

Gln Asn Asp Tyr Leu Asp His His Asn Ile Ile Gly Trp Thr Arg Glu
                405                 410                 415

Gly Asn Thr Ala His Pro Asn Ser Gly Leu Ala Thr Ile Met Ser Asp
            420                 425                 430

Gly Ala Gly Gly Ser Lys Trp Met Phe Val Gly Arg Asn Lys Ala Gly
        435                 440                 445

Gln Val Trp Ser Asp Ile Thr Gly Asn Arg Thr Gly Thr Val Thr Ile
    450                 455                 460

Asn Ala Asp Gly Trp Gly Asn Phe Ser Val Asn Gly Gly Ser Val Ser
465                 470                 475                 480

Ile Trp Val Asn Lys
            485

<210> SEQ ID NO 7
<211> LENGTH: 483
<212> TYPE: PRT
<213> ORGANISM: Artificial Sequence
<220> FEATURE:
<223> OTHER INFORMATION: Chemically synthesized AmyS sequence

<400> SEQUENCE: 7

Ala Asn Leu Asn Gly Thr Leu Met Gln Tyr Phe Glu Trp Tyr Met Pro
1               5                   10                  15

Asn Asp Gly Gln His Trp Lys Arg Leu Gln Asn Asp Ser Ala Tyr Leu
            20                  25                  30

Ala Glu His Gly Ile Thr Ala Val Trp Ile Pro Pro Ala Tyr Lys Gly
        35                  40                  45

Thr Ser Gln Ala Asp Val Gly Tyr Gly Ala Tyr Asp Leu Tyr Asp Leu
    50                  55                  60

Gly Glu Phe His Gln Lys Gly Thr Val Arg Thr Lys Tyr Gly Thr Lys
65                  70                  75                  80
```

Gly Glu Leu Gln Ser Ala Ile Lys Ser Leu His Ser Arg Asp Ile Asn
                    85                  90                  95

Val Tyr Gly Asp Val Val Ile Asn His Lys Gly Ala Asp Ala Thr
                100                 105                 110

Glu Asp Val Thr Ala Val Glu Val Asp Pro Ala Asp Arg Asn Arg Val
                    115                 120                 125

Ile Ser Gly Glu His Leu Ile Lys Ala Trp Thr His Phe His Phe Pro
130                 135                 140

Gly Arg Gly Ser Thr Tyr Ser Asp Phe Lys Trp His Trp Tyr His Phe
145                 150                 155                 160

Asp Gly Thr Asp Trp Asp Glu Ser Arg Lys Leu Asn Arg Ile Tyr Lys
                165                 170                 175

Phe Gln Gly Lys Ala Trp Asp Trp Glu Val Ser Asn Glu Asn Gly Asn
                180                 185                 190

Tyr Asp Tyr Leu Met Tyr Ala Asp Ile Asp Tyr Asp His Pro Asp Val
                195                 200                 205

Ala Ala Glu Ile Lys Arg Trp Gly Thr Trp Tyr Ala Asn Glu Leu Gln
210                 215                 220

Leu Asp Gly Phe Arg Leu Asp Ala Val Lys His Ile Lys Phe Ser Phe
225                 230                 235                 240

Leu Arg Asp Trp Val Asn His Val Arg Glu Lys Thr Gly Lys Glu Met
                245                 250                 255

Phe Thr Val Ala Glu Tyr Trp Gln Asn Asp Leu Gly Ala Leu Glu Asn
                260                 265                 270

Tyr Leu Asn Lys Thr Asn Phe Asn His Ser Val Phe Asp Val Pro Leu
                275                 280                 285

His Tyr Gln Phe His Ala Ala Ser Thr Gln Gly Gly Tyr Asp Met
290                 295                 300

Arg Lys Leu Leu Asn Gly Thr Val Val Ser Lys His Pro Leu Lys Ser
305                 310                 315                 320

Val Thr Phe Val Asp Asn His Asp Thr Gln Pro Gly Gln Ser Leu Glu
                325                 330                 335

Ser Thr Val Gln Thr Trp Phe Lys Pro Leu Ala Tyr Ala Phe Ile Leu
                340                 345                 350

Thr Arg Glu Ser Gly Tyr Pro Gln Val Phe Tyr Gly Asp Met Tyr Gly
                355                 360                 365

Thr Lys Gly Asp Ser Gln Arg Glu Ile Pro Ala Leu Lys His Lys Ile
370                 375                 380

Glu Pro Ile Leu Lys Ala Arg Lys Gln Tyr Ala Tyr Gly Ala Gln His
385                 390                 395                 400

Asp Tyr Phe Asp His His Asp Ile Val Gly Trp Thr Arg Glu Gly Asp
                405                 410                 415

Ser Ser Val Ala Asn Ser Gly Leu Ala Ala Leu Ile Thr Asp Gly Pro
                420                 425                 430

Gly Gly Ala Lys Arg Met Tyr Val Gly Arg Gln Asn Ala Gly Glu Thr
                435                 440                 445

Trp His Asp Ile Thr Gly Asn Arg Ser Glu Pro Val Val Ile Asn Ser
450                 455                 460

Glu Gly Trp Gly Glu Phe His Val Asn Gly Gly Ser Val Ser Ile Tyr
465                 470                 475                 480

Val Gln Arg

<210> SEQ ID NO 8

<211> LENGTH: 483
<212> TYPE: PRT
<213> ORGANISM: Artificial Sequence
<220> FEATURE:
<223> OTHER INFORMATION: Chemically synthesized AmyS sequence

<400> SEQUENCE: 8

```
Ala Asn Leu Asn Gly Thr Leu Met Gln Tyr Phe Glu Trp Tyr Met Pro
1               5                   10                  15

Asn Asp Gly Gln His Trp Arg Arg Leu Gln Asn Asp Ser Ala Tyr Leu
            20                  25                  30

Ala Glu His Gly Ile Thr Ala Val Trp Ile Pro Pro Ala Tyr Lys Gly
        35                  40                  45

Thr Ser Gln Ala Asp Val Gly Tyr Gly Ala Tyr Asp Leu Tyr Asp Leu
    50                  55                  60

Gly Glu Phe His Gln Lys Gly Thr Val Arg Thr Lys Tyr Gly Thr Lys
65                  70                  75                  80

Gly Glu Leu Gln Ser Ala Ile Lys Ser Leu His Ser Arg Asp Ile Asn
                85                  90                  95

Val Tyr Gly Asp Val Val Ile Asn His Lys Gly Gly Ala Asp Ala Thr
            100                 105                 110

Glu Asp Val Thr Ala Val Glu Val Asp Pro Ala Asp Arg Asn Arg Val
        115                 120                 125

Ile Ser Gly Glu His Leu Ile Lys Ala Trp Thr His Phe His Phe Pro
    130                 135                 140

Gly Arg Gly Ser Thr Tyr Ser Asp Phe Lys Trp His Trp Tyr His Phe
145                 150                 155                 160

Asp Gly Thr Asp Trp Asp Glu Ser Arg Lys Leu Asn Arg Ile Tyr Lys
                165                 170                 175

Phe Gln Gly Lys Ala Trp Asp Trp Glu Val Ser Asn Glu Asn Gly Asn
            180                 185                 190

Tyr Asp Tyr Leu Met Tyr Ala Asp Ile Asp Tyr Asp His Pro Asp Val
        195                 200                 205

Ala Ala Glu Ile Lys Arg Trp Gly Thr Trp Tyr Ala Asn Glu Leu Gln
    210                 215                 220

Leu Asp Gly Phe Arg Leu Asp Ala Val Lys His Ile Lys Phe Ser Phe
225                 230                 235                 240

Leu Arg Asp Trp Val Asn His Val Arg Glu Lys Thr Gly Lys Glu Met
                245                 250                 255

Phe Thr Val Ala Glu Tyr Trp Gln Asn Asp Leu Gly Ala Leu Glu Asn
            260                 265                 270

Tyr Leu Asn Lys Thr Asn Phe Asn His Ser Val Phe Asp Val Pro Leu
        275                 280                 285

His Tyr Gln Phe His Ala Ala Ser Thr Gln Gly Gly Gly Tyr Asp Met
    290                 295                 300

Arg Lys Leu Leu Asn Gly Thr Val Val Ser Lys His Pro Leu Lys Ser
305                 310                 315                 320

Val Thr Phe Val Asp Asn His Asp Thr Gln Pro Gly Gln Ser Leu Glu
                325                 330                 335

Ser Thr Val Gln Thr Trp Phe Lys Pro Leu Ala Tyr Ala Phe Ile Leu
            340                 345                 350

Thr Arg Glu Ser Gly Tyr Pro Gln Val Phe Tyr Gly Asp Met Tyr Gly
        355                 360                 365

Thr Lys Gly Asp Ser Gln Arg Glu Ile Pro Ala Leu Lys His Lys Ile
    370                 375                 380
```

```
Glu Pro Ile Leu Lys Ala Arg Lys Gln Tyr Ala Tyr Gly Ala Gln His
385                 390                 395                 400

Asp Tyr Phe Asp His His Asp Ile Val Gly Trp Thr Arg Glu Gly Asp
            405                 410                 415

Ser Ser Val Ala Asn Ser Gly Leu Ala Ala Leu Ile Thr Asp Gly Pro
        420                 425                 430

Gly Gly Ala Lys Arg Met Tyr Val Gly Arg Gln Asn Ala Gly Glu Thr
    435                 440                 445

Trp His Asp Ile Thr Gly Asn Arg Ser Glu Pro Val Val Ile Asn Ser
    450                 455                 460

Glu Gly Trp Gly Glu Phe His Val Asn Gly Gly Ser Val Ser Ile Tyr
465                 470                 475                 480

Val Gln Arg

<210> SEQ ID NO 9
<211> LENGTH: 483
<212> TYPE: PRT
<213> ORGANISM: Artificial Sequence
<220> FEATURE:
<223> OTHER INFORMATION: Chemically synthesized AmyS sequence

<400> SEQUENCE: 9

Val Asn Gly Thr Leu Met Gln Tyr Phe Glu Trp Tyr Thr Pro Asn Asp
1               5                   10                  15

Gly Gln His Trp Lys Arg Leu Gln Asn Asp Ala Glu His Leu Ser Asp
            20                  25                  30

Ile Gly Ile Thr Ala Val Trp Ile Pro Pro Ala Tyr Lys Gly Leu Ser
        35                  40                  45

Gln Ser Asp Asn Gly Tyr Gly Pro Tyr Asp Leu Tyr Asp Leu Gly Glu
    50                  55                  60

Phe Gln Gln Lys Gly Thr Val Arg Thr Lys Tyr Gly Thr Lys Ser Glu
65                  70                  75                  80

Leu Gln Asp Ala Ile Gly Ser Leu His Ser Arg Asn Val Gln Val Tyr
                85                  90                  95

Gly Asp Val Val Leu Asn His Lys Ala Gly Ala Asp Ala Thr Glu Asp
            100                 105                 110

Val Thr Ala Val Glu Val Asn Pro Ala Asn Arg Asn Gln Glu Thr Ser
        115                 120                 125

Glu Glu Tyr Gln Ile Lys Ala Trp Thr Asp Phe Arg Phe Pro Gly Arg
130                 135                 140

Gly Asn Thr Tyr Ser Asp Phe Lys Trp His Trp Tyr His Phe Asp Gly
145                 150                 155                 160

Ala Asp Trp Asp Glu Ser Arg Lys Ile Ser Arg Ile Phe Lys Phe Arg
                165                 170                 175

Gly Glu Gly Lys Ala Trp Asp Trp Glu Val Ser Ser Glu Asn Gly Asn
            180                 185                 190

Tyr Asp Tyr Leu Met Tyr Ala Asp Val Asp Tyr Asp His Pro Asp Val
        195                 200                 205

Val Ala Glu Thr Lys Lys Trp Gly Ile Trp Tyr Ala Asn Glu Leu Ser
210                 215                 220

Leu Asp Gly Phe Arg Ile Asp Ala Ala Lys His Ile Lys Phe Ser Phe
225                 230                 235                 240

Leu Arg Asp Trp Val Gln Ala Val Arg Gln Ala Thr Gly Lys Glu Met
                245                 250                 255

Phe Thr Val Ala Glu Tyr Trp Gln Asn Asn Ala Gly Lys Leu Glu Asn
            260                 265                 270
```

```
Tyr Leu Asn Lys Thr Ser Phe Asn Gln Ser Val Phe Asp Val Pro Leu
        275                 280                 285

His Phe Asn Leu Gln Ala Ala Ser Ser Gln Gly Gly Tyr Asp Met
    290                 295                 300

Arg Arg Leu Leu Asp Gly Thr Val Val Ser Arg His Pro Glu Lys Ala
305                 310                 315                 320

Val Thr Phe Val Glu Asn His Asp Thr Gln Pro Gly Gln Ser Leu Glu
                325                 330                 335

Ser Thr Val Gln Thr Trp Phe Lys Pro Leu Ala Tyr Ala Phe Ile Leu
            340                 345                 350

Thr Arg Glu Ser Gly Tyr Pro Gln Val Phe Tyr Gly Asp Met Tyr Gly
        355                 360                 365

Thr Lys Gly Thr Ser Pro Lys Glu Ile Pro Ser Leu Lys Asp Asn Ile
    370                 375                 380

Glu Pro Ile Leu Lys Ala Arg Lys Glu Tyr Ala Tyr Gly Pro Gln His
385                 390                 395                 400

Asp Tyr Ile Asp His Pro Asp Val Ile Gly Trp Thr Arg Glu Gly Asp
                405                 410                 415

Ser Ser Ala Ala Lys Ser Gly Leu Ala Ala Leu Ile Thr Asp Gly Pro
            420                 425                 430

Gly Gly Ser Lys Arg Met Tyr Ala Gly Leu Lys Asn Ala Gly Glu Thr
        435                 440                 445

Trp Tyr Asp Ile Thr Gly Asn Arg Ser Asp Thr Val Lys Ile Gly Ser
    450                 455                 460

Asp Gly Trp Gly Glu Phe His Val Asn Asp Gly Ser Val Ser Ile Tyr
465                 470                 475                 480

Val Gln Lys

<210> SEQ ID NO 10
<211> LENGTH: 485
<212> TYPE: PRT
<213> ORGANISM: Artificial Sequence
<220> FEATURE:
<223> OTHER INFORMATION: Chemically synthesized AmyS sequence

<400> SEQUENCE: 10

His His Asn Gly Thr Asn Gly Thr Met Met Gln Tyr Phe Glu Trp Tyr
1               5                   10                  15

Leu Pro Asn Asp Gly Asn His Trp Asn Arg Leu Arg Ser Asp Ala Ser
            20                  25                  30

Asn Leu Lys Asp Lys Gly Ile Ser Ala Val Trp Ile Pro Pro Ala Trp
        35                  40                  45

Lys Gly Ala Ser Gln Asn Asp Val Gly Tyr Gly Ala Tyr Asp Leu Tyr
    50                  55                  60

Asp Leu Gly Glu Phe Asn Gln Lys Gly Thr Ile Arg Thr Lys Tyr Gly
65                  70                  75                  80

Thr Arg Asn Gln Leu Gln Ala Ala Val Asn Ala Leu Lys Ser Asn Gly
                85                  90                  95

Ile Gln Val Tyr Gly Asp Val Val Met Asn His Lys Gly Gly Ala Asp
            100                 105                 110

Ala Thr Glu Met Val Arg Ala Val Glu Val Asn Pro Asn Asn Arg Asn
        115                 120                 125

Gln Glu Val Ser Gly Glu Tyr Thr Ile Glu Ala Trp Thr Lys Phe Asp
    130                 135                 140

Phe Pro Gly Arg Gly Asn Thr His Ser Asn Phe Lys Trp Arg Trp Tyr
```

```
            145                 150                 155                 160
His Phe Asp Gly Val Asp Trp Asp Gln Ser Arg Lys Leu Asn Asn Arg
                165                 170                 175
Ile Tyr Lys Phe Arg Gly Asp Gly Lys Gly Trp Asp Trp Glu Val Asp
                180                 185                 190
Thr Glu Asn Gly Asn Tyr Asp Tyr Leu Met Tyr Ala Asp Ile Asp Met
                195                 200                 205
Asp His Pro Glu Val Val Asn Glu Leu Arg Asn Trp Gly Val Trp Tyr
            210                 215                 220
Thr Asn Thr Leu Gly Leu Asp Gly Phe Arg Ile Asp Ala Val Lys His
225                 230                 235                 240
Ile Lys Tyr Ser Phe Thr Arg Asp Trp Ile Asn His Val Arg Ser Ala
                245                 250                 255
Thr Gly Lys Asn Met Phe Ala Val Ala Glu Phe Trp Lys Asn Asp Leu
                260                 265                 270
Gly Ala Ile Glu Asn Tyr Leu Asn Lys Thr Asn Trp Asn His Ser Val
                275                 280                 285
Phe Asp Val Pro Leu His Tyr Asn Leu Tyr Asn Ala Ser Lys Ser Gly
            290                 295                 300
Gly Asn Tyr Asp Met Arg Gln Ile Phe Asn Gly Thr Val Val Gln Arg
305                 310                 315                 320
His Pro Met His Ala Val Thr Phe Val Asp Asn His Asp Ser Gln Pro
                325                 330                 335
Glu Glu Ala Leu Glu Ser Phe Val Glu Glu Trp Phe Lys Pro Leu Ala
                340                 345                 350
Tyr Ala Leu Thr Leu Thr Arg Glu Gln Gly Tyr Pro Ser Val Phe Tyr
                355                 360                 365
Gly Asp Tyr Tyr Gly Ile Pro Thr His Gly Val Pro Ala Met Lys Ser
            370                 375                 380
Lys Ile Asp Pro Ile Leu Glu Ala Arg Gln Lys Tyr Ala Tyr Gly Arg
385                 390                 395                 400
Gln Asn Asp Tyr Leu Asp His His Asn Ile Ile Gly Trp Thr Arg Glu
                405                 410                 415
Gly Asn Thr Ala His Pro Asn Ser Gly Leu Ala Thr Ile Met Ser Asp
                420                 425                 430
Gly Ala Gly Gly Asn Lys Trp Met Phe Val Gly Arg Asn Lys Ala Gly
            435                 440                 445
Gln Val Trp Thr Asp Ile Thr Gly Asn Arg Ala Gly Thr Val Thr Ile
            450                 455                 460
Asn Ala Asp Gly Trp Gly Asn Phe Ser Val Asn Gly Gly Ser Val Ser
465                 470                 475                 480
Ile Trp Val Asn Lys
            485

<210> SEQ ID NO 11
<211> LENGTH: 485
<212> TYPE: PRT
<213> ORGANISM: Artificial Sequence
<220> FEATURE:
<223> OTHER INFORMATION: Chemically synthesized AmyS sequence

<400> SEQUENCE: 11

His His Asn Gly Thr Asn Gly Thr Met Met Gln Tyr Phe Glu Trp His
1               5                   10                  15
Leu Pro Asn Asp Gly Asn His Trp Asn Arg Leu Arg Asp Asp Ala Ser
                20                  25                  30
```

-continued

Asn Leu Arg Asn Arg Gly Ile Thr Ala Ile Trp Ile Pro Pro Ala Trp
        35                  40                  45

Lys Gly Thr Ser Gln Asn Asp Val Gly Tyr Gly Ala Tyr Asp Leu Tyr
 50                  55                  60

Asp Leu Gly Glu Phe Asn Gln Lys Gly Thr Val Arg Thr Lys Tyr Gly
 65                  70                  75                  80

Thr Arg Ser Gln Leu Glu Ser Ala Ile His Ala Leu Lys Asn Asn Gly
                 85                  90                  95

Val Gln Val Tyr Gly Asp Val Val Met Asn His Lys Gly Gly Ala Asp
            100                 105                 110

Ala Thr Glu Asn Val Leu Ala Val Glu Val Asn Pro Asn Asn Arg Asn
        115                 120                 125

Gln Glu Ile Ser Gly Asp Tyr Thr Ile Glu Ala Trp Thr Lys Phe Asp
    130                 135                 140

Phe Pro Gly Arg Gly Asn Thr Tyr Ser Asp Phe Lys Trp Arg Trp Tyr
145                 150                 155                 160

His Phe Asp Gly Val Asp Trp Asp Gln Ser Arg Gln Phe Gln Asn Arg
                165                 170                 175

Ile Tyr Lys Phe Arg Gly Asp Gly Lys Ala Trp Asp Trp Glu Val Asp
            180                 185                 190

Ser Glu Asn Gly Asn Tyr Asp Tyr Leu Met Tyr Ala Asp Val Asp Met
        195                 200                 205

Asp His Pro Glu Val Val Asn Glu Leu Arg Arg Trp Gly Glu Trp Tyr
    210                 215                 220

Thr Asn Thr Leu Asn Leu Asp Gly Phe Arg Ile Asp Ala Val Lys His
225                 230                 235                 240

Ile Lys Tyr Ser Phe Thr Arg Asp Trp Leu Thr His Val Arg Asn Ala
                245                 250                 255

Thr Gly Lys Glu Met Phe Ala Val Ala Glu Phe Trp Lys Asn Asp Leu
            260                 265                 270

Gly Ala Leu Glu Asn Tyr Leu Asn Lys Thr Asn Trp Asn His Ser Val
        275                 280                 285

Phe Asp Val Pro Leu His Tyr Asn Leu Tyr Asn Ala Ser Asn Ser Gly
    290                 295                 300

Gly Asn Tyr Asp Met Ala Lys Leu Leu Asn Gly Thr Val Val Gln Lys
305                 310                 315                 320

His Pro Met His Ala Val Thr Phe Val Asp Asn His Asp Ser Gln Pro
                325                 330                 335

Gly Glu Ser Leu Glu Ser Phe Val Gln Glu Trp Phe Lys Pro Leu Ala
            340                 345                 350

Tyr Ala Leu Ile Leu Thr Arg Glu Gln Gly Tyr Pro Ser Val Phe Tyr
        355                 360                 365

Gly Asp Tyr Tyr Gly Ile Pro Thr His Ser Val Pro Ala Met Lys Ala
    370                 375                 380

Lys Ile Asp Pro Ile Leu Glu Ala Arg Gln Asn Phe Ala Tyr Gly Thr
385                 390                 395                 400

Gln His Asp Tyr Phe Asp His His Asn Ile Ile Gly Trp Thr Arg Glu
                405                 410                 415

Gly Asn Thr Thr His Pro Asn Ser Gly Leu Ala Thr Ile Met Ser Asp
            420                 425                 430

Gly Pro Gly Gly Glu Lys Trp Met Tyr Val Gly Gln Asn Lys Ala Gly
        435                 440                 445

Gln Val Trp His Asp Ile Thr Gly Asn Lys Pro Gly Thr Val Thr Ile

```
                    450                 455                 460
Asn Ala Asp Gly Trp Ala Asn Phe Ser Val Asn Gly Gly Ser Val Ser
465                 470                 475                 480

Ile Trp Val Lys Arg
                485

<210> SEQ ID NO 12
<211> LENGTH: 485
<212> TYPE: PRT
<213> ORGANISM: Artificial Sequence
<220> FEATURE:
<223> OTHER INFORMATION: Chemically synthesized AmyS sequence

<400> SEQUENCE: 12

His His Asn Gly Thr Asn Gly Thr Met Met Gln Tyr Phe Glu Trp His
1               5                   10                  15

Leu Pro Asn Asp Gly Asn His Trp Asn Arg Leu Arg Asp Asp Ala Ala
            20                  25                  30

Asn Leu Lys Ser Lys Gly Ile Thr Ala Val Trp Ile Pro Pro Ala Trp
        35                  40                  45

Lys Gly Thr Ser Gln Asn Asp Val Gly Tyr Gly Ala Tyr Asp Leu Tyr
50                  55                  60

Asp Leu Gly Glu Phe Asn Gln Lys Gly Thr Val Arg Thr Lys Tyr Gly
65                  70                  75                  80

Thr Arg Ser Gln Leu Gln Gly Ala Val Thr Ser Leu Lys Asn Asn Gly
                85                  90                  95

Ile Gln Val Tyr Gly Asp Val Val Met Asn His Lys Gly Gly Ala Asp
            100                 105                 110

Gly Thr Glu Met Val Asn Ala Val Glu Val Asn Arg Ser Asn Arg Asn
        115                 120                 125

Gln Glu Ile Ser Gly Glu Tyr Thr Ile Glu Ala Trp Thr Lys Phe Asp
130                 135                 140

Phe Pro Gly Arg Gly Asn Thr His Ser Asn Phe Lys Trp Arg Trp Tyr
145                 150                 155                 160

His Phe Asp Gly Thr Asp Trp Asp Gln Ser Arg Gln Leu Gln Asn Lys
                165                 170                 175

Ile Tyr Lys Phe Arg Gly Thr Gly Lys Ala Trp Asp Trp Glu Val Asp
            180                 185                 190

Ile Glu Asn Gly Asn Tyr Asp Tyr Leu Met Tyr Ala Asp Ile Asp Met
        195                 200                 205

Asp His Pro Glu Val Ile Glu Leu Arg Asn Trp Gly Val Trp Tyr
210                 215                 220

Thr Asn Thr Leu Asn Leu Asp Gly Phe Arg Ile Asp Ala Val Lys His
225                 230                 235                 240

Ile Lys Tyr Ser Tyr Thr Arg Asp Trp Leu Thr His Val Arg Asn Thr
                245                 250                 255

Thr Gly Lys Pro Met Phe Ala Val Ala Glu Phe Trp Lys Asn Asp Leu
            260                 265                 270

Ala Ala Ile Glu Asn Tyr Leu Asn Lys Thr Ser Trp Asn His Ser Val
        275                 280                 285

Phe Asp Val Pro Leu His Tyr Asn Leu Tyr Asn Ala Ser Asn Ser Gly
290                 295                 300

Gly Tyr Phe Asp Met Arg Asn Ile Leu Asn Gly Ser Val Val Gln Lys
305                 310                 315                 320

His Pro Ile His Ala Val Thr Phe Val Asp Asn His Asp Ser Gln Pro
                325                 330                 335
```

Gly Glu Ala Leu Glu Ser Phe Val Gln Ser Trp Phe Lys Pro Leu Ala
            340                 345                 350

Tyr Ala Leu Ile Leu Thr Arg Glu Gln Gly Tyr Pro Ser Val Phe Tyr
            355                 360                 365

Gly Asp Tyr Tyr Gly Ile Pro Thr His Gly Val Pro Ser Met Lys Ser
370                 375                 380

Lys Ile Asp Pro Leu Leu Gln Ala Arg Gln Thr Tyr Ala Tyr Gly Thr
385                 390                 395                 400

Gln His Asp Tyr Phe Asp His His Asp Ile Ile Gly Trp Thr Arg Glu
                405                 410                 415

Gly Asp Ser Ser His Pro Asn Ser Gly Leu Ala Thr Ile Met Ser Asp
            420                 425                 430

Gly Pro Gly Gly Asn Lys Trp Met Tyr Val Gly Lys His Lys Ala Gly
            435                 440                 445

Gln Val Trp Arg Asp Ile Thr Gly Asn Arg Ser Gly Thr Val Thr Ile
450                 455                 460

Asn Ala Asp Gly Trp Gly Asn Phe Thr Val Asn Gly Gly Ala Val Ser
465                 470                 475                 480

Val Trp Val Lys Gln
            485

<210> SEQ ID NO 13
<211> LENGTH: 480
<212> TYPE: PRT
<213> ORGANISM: Artificial Sequence
<220> FEATURE:
<223> OTHER INFORMATION: Chemically synthesized AmyS sequence

<400> SEQUENCE: 13

Asp Gly Leu Asn Gly Thr Met Met Gln Tyr Tyr Glu Trp His Leu Glu
1               5                   10                  15

Asn Asp Gly Gln His Trp Asn Arg Leu His Asp Ala Ala Ala Leu
            20                  25                  30

Ser Asp Ala Gly Ile Thr Ala Ile Trp Ile Pro Pro Ala Tyr Lys Gly
        35                  40                  45

Asn Ser Gln Ala Asp Val Gly Tyr Gly Ala Tyr Asp Leu Tyr Asp Leu
    50                  55                  60

Gly Glu Phe Asn Gln Lys Gly Thr Val Arg Thr Lys Tyr Gly Thr Lys
65                  70                  75                  80

Ala Gln Leu Glu Arg Ala Ile Gly Ser Leu Lys Ser Asn Asp Ile Asn
            85                  90                  95

Val Tyr Gly Asp Val Val Met Asn His Lys Met Gly Ala Asp Phe Thr
        100                 105                 110

Glu Ala Val Gln Ala Val Gln Val Asn Pro Thr Asn Arg Trp Gln Asp
    115                 120                 125

Ile Ser Gly Ala Tyr Thr Ile Asp Ala Trp Thr Gly Phe Asp Phe Ser
130                 135                 140

Gly Arg Asn Asn Ala Tyr Ser Asp Phe Lys Trp Arg Trp Phe His Phe
145                 150                 155                 160

Asn Gly Val Asp Trp Asp Gln Arg Tyr Gln Glu Asn His Ile Phe Arg
            165                 170                 175

Phe Ala Asn Thr Asn Trp Asn Trp Arg Val Asp Glu Glu Asn Gly Asn
        180                 185                 190

Tyr Asp Tyr Leu Leu Gly Ser Asn Ile Asp Phe Ser His Pro Glu Val
    195                 200                 205

```
Gln Asp Glu Leu Lys Asp Trp Gly Ser Trp Phe Thr Asp Glu Leu Asp
    210                 215                 220

Leu Asp Gly Tyr Arg Leu Asp Ala Ile Lys His Ile Pro Phe Trp Tyr
225                 230                 235                 240

Thr Ser Asp Trp Val Arg His Gln Arg Asn Glu Ala Asp Gln Asp Leu
                245                 250                 255

Phe Val Val Gly Glu Tyr Trp Lys Asp Val Gly Ala Leu Glu Phe
            260                 265                 270

Tyr Leu Asp Glu Met Asn Trp Glu Met Ser Leu Phe Asp Val Pro Leu
        275                 280                 285

Asn Tyr Asn Phe Tyr Arg Ala Ser Gln Gln Gly Gly Ser Tyr Asp Met
    290                 295                 300

Arg Asn Ile Leu Arg Gly Ser Leu Val Glu Ala His Pro Met His Ala
305                 310                 315                 320

Val Thr Phe Val Asp Asn His Asp Thr Gln Pro Gly Glu Ser Leu Glu
                325                 330                 335

Ser Trp Val Ala Asp Trp Phe Lys Pro Leu Ala Tyr Ala Thr Ile Leu
            340                 345                 350

Thr Arg Glu Gly Gly Tyr Pro Asn Val Phe Tyr Gly Asp Tyr Tyr Gly
        355                 360                 365

Ile Pro Asn Asp Asn Ile Ser Ala Lys Lys Asp Met Ile Asp Glu Leu
370                 375                 380

Leu Asp Ala Arg Gln Asn Tyr Ala Tyr Gly Thr Gln His Asp Tyr Phe
385                 390                 395                 400

Asp His Trp Asp Val Val Gly Trp Thr Arg Glu Gly Ser Ser Ser Arg
                405                 410                 415

Pro Asn Ser Gly Leu Ala Thr Ile Met Ser Asn Gly Pro Gly Gly Ser
            420                 425                 430

Lys Trp Met Tyr Val Gly Arg Gln Asn Ala Gly Gln Thr Trp Thr Asp
        435                 440                 445

Leu Thr Gly Asn Asn Gly Ala Ser Val Thr Ile Asn Gly Asp Gly Trp
    450                 455                 460

Gly Glu Phe Phe Thr Asn Gly Gly Ser Val Ser Val Tyr Val Asn Gln
465                 470                 475                 480

<210> SEQ ID NO 14
<211> LENGTH: 480
<212> TYPE: PRT
<213> ORGANISM: Artificial Sequence
<220> FEATURE:
<223> OTHER INFORMATION: Chemically synthesized AmyS sequence

<400> SEQUENCE: 14

Asp Gly Leu Asn Gly Thr Met Met Gln Tyr Tyr Glu Trp His Leu Glu
1               5                   10                  15

Asn Asp Gly Gln His Trp Asn Arg Leu His Asp Asp Ala Glu Ala Leu
            20                  25                  30

Ser Asn Ala Gly Ile Thr Ala Ile Trp Ile Pro Pro Ala Tyr Lys Gly
        35                  40                  45

Asn Ser Gln Ala Asp Val Gly Tyr Gly Ala Tyr Asp Leu Tyr Asp Leu
    50                  55                  60

Gly Glu Phe Asn Gln Lys Gly Thr Val Arg Thr Lys Tyr Gly Thr Lys
65                  70                  75                  80

Ala Gln Leu Glu Arg Ala Ile Gly Ser Leu Lys Ser Asn Asp Ile Asn
                85                  90                  95

Val Tyr Gly Asp Val Val Met Asn His Lys Leu Gly Ala Asp Phe Thr
```

```
            100                 105                 110
Glu Ala Val Gln Ala Val Gln Val Asn Pro Ser Asn Arg Trp Gln Asp
        115                 120                 125
Ile Ser Gly Val Tyr Thr Ile Asp Ala Trp Thr Gly Phe Asp Phe Pro
    130                 135                 140
Gly Arg Asn Asn Ala Tyr Ser Asp Phe Lys Trp Arg Trp Phe His Phe
145                 150                 155                 160
Asn Gly Val Asp Trp Asp Gln Arg Tyr Gln Glu Asn His Leu Phe Arg
                165                 170                 175
Phe Ala Asn Thr Asn Trp Asn Trp Arg Val Asp Glu Glu Asn Gly Asn
            180                 185                 190
Tyr Asp Tyr Leu Leu Gly Ser Asn Ile Asp Phe Ser His Pro Glu Val
        195                 200                 205
Gln Glu Glu Leu Lys Asp Trp Gly Ser Trp Phe Thr Asp Glu Leu Asp
    210                 215                 220
Leu Asp Gly Tyr Arg Leu Asp Ala Ile Lys His Ile Pro Phe Trp Tyr
225                 230                 235                 240
Thr Ser Asp Trp Val Arg His Gln Arg Ser Glu Ala Asp Gln Asp Leu
                245                 250                 255
Phe Val Val Gly Glu Tyr Trp Lys Asp Asp Val Gly Ala Leu Glu Phe
            260                 265                 270
Tyr Leu Asp Glu Met Asn Trp Glu Met Ser Leu Phe Asp Val Pro Leu
        275                 280                 285
Asn Tyr Asn Phe Tyr Arg Ala Ser Lys Gln Gly Gly Ser Tyr Asp Met
    290                 295                 300
Arg Asn Ile Leu Arg Gly Ser Leu Val Glu Ala His Pro Ile His Ala
305                 310                 315                 320
Val Thr Phe Val Asp Asn His Asp Thr Gln Pro Gly Glu Ser Leu Glu
                325                 330                 335
Ser Trp Val Ala Asp Trp Phe Lys Pro Leu Ala Tyr Ala Thr Ile Leu
            340                 345                 350
Thr Arg Glu Gly Gly Tyr Pro Asn Val Phe Tyr Gly Asp Tyr Tyr Gly
        355                 360                 365
Ile Pro Asn Asp Asn Ile Ser Ala Lys Lys Asp Met Ile Asp Glu Leu
    370                 375                 380
Leu Asp Ala Arg Gln Asn Tyr Ala Tyr Gly Thr Gln His Asp Tyr Phe
385                 390                 395                 400
Asp His Trp Asp Ile Val Gly Trp Thr Arg Glu Gly Thr Ser Ser Arg
                405                 410                 415
Pro Asn Ser Gly Leu Ala Thr Ile Met Ser Asn Gly Pro Gly Gly Ser
            420                 425                 430
Lys Trp Met Tyr Val Gly Gln Gln His Ala Gly Gln Thr Trp Thr Asp
        435                 440                 445
Leu Thr Gly Asn His Ala Ala Ser Val Thr Ile Asn Gly Asp Gly Trp
    450                 455                 460
Gly Glu Phe Phe Thr Asn Gly Gly Ser Val Ser Val Tyr Val Asn Gln
465                 470                 475                 480

<210> SEQ ID NO 15
<211> LENGTH: 486
<212> TYPE: PRT
<213> ORGANISM: Artificial Sequence
<220> FEATURE:
<223> OTHER INFORMATION: Chemically synthesized AmyS sequence

<400> SEQUENCE: 15
```

```
Ala Ala Pro Phe Asn Gly Thr Met Met Gln Tyr Phe Glu Trp Tyr Leu
1               5                   10                  15

Pro Asp Asp Gly Thr Leu Trp Thr Lys Val Ala Asn Glu Ala Asn Asn
            20                  25                  30

Leu Ser Ser Leu Gly Ile Thr Ala Leu Trp Leu Pro Pro Ala Tyr Lys
        35                  40                  45

Gly Thr Ser Arg Ser Asp Val Gly Tyr Gly Val Tyr Asp Leu Tyr Asp
    50                  55                  60

Leu Gly Glu Phe Asn Gln Lys Gly Thr Val Arg Thr Lys Tyr Gly Thr
65                  70                  75                  80

Lys Ala Gln Tyr Leu Gln Ala Ile Gln Ala Ala His Ala Ala Gly Met
                85                  90                  95

Gln Val Tyr Ala Asp Val Val Phe Asp His Lys Gly Gly Ala Asp Gly
                100                 105                 110

Thr Glu Trp Val Asp Ala Val Glu Val Asn Pro Ser Asp Arg Asn Gln
            115                 120                 125

Glu Ile Ser Gly Thr Tyr Gln Ile Gln Ala Trp Thr Lys Phe Asp Phe
        130                 135                 140

Pro Gly Arg Gly Asn Thr Tyr Ser Ser Phe Lys Trp Arg Trp Tyr His
145                 150                 155                 160

Phe Asp Gly Val Asp Trp Asp Glu Ser Arg Lys Leu Ser Arg Ile Tyr
                165                 170                 175

Lys Phe Arg Gly Lys Ala Trp Asp Trp Glu Val Asp Thr Glu Phe Gly
                180                 185                 190

Asn Tyr Asp Tyr Leu Met Tyr Ala Asp Leu Asp Met Asp His Pro Glu
                195                 200                 205

Val Val Thr Glu Leu Lys Asn Trp Gly Lys Trp Tyr Val Asn Thr Thr
210                 215                 220

Asn Ile Asp Gly Phe Arg Leu Asp Ala Val Lys His Ile Lys Phe Ser
225                 230                 235                 240

Phe Phe Pro Asp Trp Leu Ser Tyr Val Arg Ser Gln Thr Gly Lys Pro
            245                 250                 255

Leu Phe Thr Val Gly Glu Tyr Trp Ser Tyr Asp Ile Asn Lys Leu His
        260                 265                 270

Asn Tyr Ile Thr Lys Thr Asn Gly Thr Met Ser Leu Phe Asp Ala Pro
        275                 280                 285

Leu His Asn Lys Phe Tyr Thr Ala Ser Lys Ser Gly Gly Ala Phe Asp
    290                 295                 300

Met Arg Thr Leu Met Thr Asn Thr Leu Met Lys Asp Gln Pro Thr Leu
305                 310                 315                 320

Ala Val Thr Phe Val Asp Asn His Asp Thr Glu Pro Gly Gln Ala Leu
                325                 330                 335

Gln Ser Trp Val Asp Pro Trp Phe Lys Pro Leu Ala Tyr Ala Phe Ile
            340                 345                 350

Leu Thr Arg Gln Glu Gly Tyr Pro Cys Val Phe Tyr Gly Asp Tyr Tyr
        355                 360                 365

Gly Ile Pro Gln Tyr Asn Ile Pro Ser Leu Lys Ser Lys Ile Asp Pro
    370                 375                 380

Leu Leu Ile Ala Arg Arg Asp Tyr Ala Tyr Gly Thr Gln His Asp Tyr
385                 390                 395                 400

Leu Asp His Ser Asp Ile Ile Gly Trp Thr Arg Glu Gly Gly Thr Glu
                405                 410                 415

Lys Pro Gly Ser Gly Leu Ala Ala Leu Ile Thr Asp Gly Pro Gly Gly
```

```
                    420             425             430
Ser Lys Trp Met Tyr Val Gly Lys Gln His Ala Gly Lys Val Phe Tyr
            435                 440                 445

Asp Leu Thr Gly Asn Arg Ser Asp Thr Val Thr Ile Asn Ser Asp Gly
        450                 455                 460

Trp Gly Glu Phe Lys Val Asn Gly Gly Ser Val Ser Val Trp Val Pro
465                 470                 475                 480

Arg Lys Thr Thr Val Ser
                485

<210> SEQ ID NO 16
<211> LENGTH: 518
<212> TYPE: PRT
<213> ORGANISM: Geobacillus stearothermophilus
<220> FEATURE:
<221> NAME/KEY: misc_feature
<223> OTHER INFORMATION: Truncated Geobacillus stearothermophilus
      alpha-amylase sequence

<400> SEQUENCE: 16

Met Leu Thr Phe His Arg Ile Ile Arg Lys Gly Trp Met Phe Leu Leu
1               5                   10                  15

Ala Phe Leu Leu Thr Ala Ser Leu Phe Cys Pro Thr Gly Gln His Ala
            20                  25                  30

Lys Ala Ala Ala Pro Phe Asn Gly Thr Met Met Gln Tyr Phe Glu Trp
        35                  40                  45

Tyr Leu Pro Asp Asp Gly Thr Leu Trp Thr Lys Val Ala Asn Glu Ala
    50                  55                  60

Asn Asn Leu Ser Ser Leu Gly Ile Thr Ala Leu Trp Leu Pro Pro Ala
65              70                  75                  80

Tyr Lys Gly Thr Ser Arg Ser Asp Val Gly Tyr Gly Val Tyr Asp Leu
                85                  90                  95

Tyr Asp Leu Gly Glu Phe Asn Gln Lys Gly Thr Val Arg Thr Lys Tyr
            100                 105                 110

Gly Thr Lys Ala Gln Tyr Leu Gln Ala Ile Gln Ala Ala His Ala Ala
        115                 120                 125

Gly Met Gln Val Tyr Ala Asp Val Val Phe Asp His Lys Gly Gly Ala
    130                 135                 140

Asp Gly Thr Glu Trp Val Asp Ala Val Glu Val Asn Pro Ser Asp Arg
145                 150                 155                 160

Asn Gln Glu Ile Ser Gly Thr Tyr Gln Ile Gln Ala Trp Thr Lys Phe
                165                 170                 175

Asp Phe Pro Gly Arg Gly Asn Thr Tyr Ser Ser Phe Lys Trp Arg Trp
            180                 185                 190

Tyr His Phe Asp Gly Val Asp Trp Asp Glu Ser Arg Lys Leu Ser Arg
        195                 200                 205

Ile Tyr Lys Phe Ile Gly Lys Ala Trp Asp Trp Glu Val Asp Thr Glu
    210                 215                 220

Asn Gly Asn Tyr Asp Tyr Leu Met Tyr Ala Asp Leu Asp Met Asp His
225                 230                 235                 240

Pro Glu Val Val Thr Glu Leu Lys Asn Trp Gly Lys Trp Tyr Val Asn
                245                 250                 255

Thr Thr Asn Ile Asp Gly Phe Arg Leu Asp Ala Val Lys His Ile Lys
            260                 265                 270

Phe Ser Phe Phe Pro Asp Trp Leu Ser Tyr Val Arg Ser Gln Thr Gly
        275                 280                 285
```

Lys Pro Leu Phe Thr Val Gly Glu Tyr Trp Ser Tyr Asp Ile Asn Lys
            290                 295                 300

Leu His Asn Tyr Ile Thr Lys Thr Asn Gly Thr Met Ser Leu Phe Asp
305                 310                 315                 320

Ala Pro Leu His Asn Lys Phe Tyr Thr Ala Ser Lys Ser Gly Gly Ala
                325                 330                 335

Phe Asp Met Arg Thr Leu Met Thr Asn Thr Leu Met Lys Asp Gln Pro
                340                 345                 350

Thr Leu Ala Val Thr Phe Val Asp Asn His Asp Thr Glu Pro Gly Gln
            355                 360                 365

Ala Leu Gln Ser Trp Val Asp Pro Trp Phe Lys Pro Leu Ala Tyr Ala
        370                 375                 380

Phe Ile Leu Thr Arg Gln Glu Gly Tyr Pro Cys Val Phe Tyr Gly Asp
385                 390                 395                 400

Tyr Tyr Gly Ile Pro Gln Tyr Asn Ile Pro Ser Leu Lys Ser Lys Ile
                405                 410                 415

Asp Pro Leu Leu Ile Ala Arg Arg Asp Tyr Ala Tyr Gly Thr Gln His
            420                 425                 430

Asp Tyr Leu Asp His Ser Asp Ile Ile Gly Trp Thr Arg Glu Gly Val
        435                 440                 445

Thr Glu Lys Pro Gly Ser Gly Leu Ala Ala Leu Ile Thr Asp Gly Pro
    450                 455                 460

Gly Gly Ser Lys Trp Met Tyr Val Gly Lys Gln His Ala Gly Lys Val
465                 470                 475                 480

Phe Tyr Asp Leu Thr Gly Asn Arg Ser Asp Thr Val Thr Ile Asn Ser
                485                 490                 495

Asp Gly Trp Gly Glu Phe Lys Val Asn Gly Gly Ser Val Ser Val Trp
            500                 505                 510

Val Pro Arg Lys Thr Thr
        515

<210> SEQ ID NO 17
<211> LENGTH: 39
<212> TYPE: DNA
<213> ORGANISM: Artificial Sequence
<220> FEATURE:
<223> OTHER INFORMATION: Synthetic S242 primer for mutagenesis
<220> FEATURE:
<221> NAME/KEY: misc_feature
<222> LOCATION: (19)..(20)
<223> OTHER INFORMATION: n is a, c, g, or t

<400> SEQUENCE: 17
gtcaagcata ttaagttcnn stttttcct gattggttg                            39

<210> SEQ ID NO 18
<211> LENGTH: 39
<212> TYPE: DNA
<213> ORGANISM: Artificial Sequence
<220> FEATURE:
<223> OTHER INFORMATION: Synthetic S242 primer for mutagenesis
<220> FEATURE:
<221> NAME/KEY: misc_feature
<222> LOCATION: (20)..(21)
<223> OTHER INFORMATION: n is a, c, g, or t

<400> SEQUENCE: 18
caaccaatca ggaaaaaasn ngaacttaat atgcttgac                           39

<210> SEQ ID NO 19
<211> LENGTH: 413

```
<212> TYPE: PRT
<213> ORGANISM: Buttiauxella sp.
<220> FEATURE:
<221> NAME/KEY: misc_feature
<223> OTHER INFORMATION: Mature protein sequence of Buttiauxella BP-17
      phytase

<400> SEQUENCE: 19
```

| | | | | | | | | | | | | | | |
|---|---|---|---|---|---|---|---|---|---|---|---|---|---|---|
| Asn | Asp | Thr | Pro | Ala | Ser | Gly | Tyr | Gln | Val | Glu | Lys | Val | Ile | Leu |
| 1 | | | | 5 | | | | | 10 | | | | | 15 |
| Ser | Arg | His | Gly | Val | Arg | Ala | Pro | Thr | Lys | Met | Thr | Gln | Thr | Met | Arg |
| | | | 20 | | | | | 25 | | | | | 30 | |
| Asp | Val | Thr | Pro | Asn | Thr | Trp | Pro | Glu | Trp | Pro | Val | Lys | Leu | Gly | Tyr |
| | | 35 | | | | | 40 | | | | | 45 | | |
| Ile | Thr | Pro | Arg | Gly | Glu | His | Leu | Ile | Ser | Leu | Met | Gly | Gly | Phe | Tyr |
| | 50 | | | | | 55 | | | | | 60 | | | |
| Arg | Gln | Lys | Phe | Gln | Gln | Gln | Gly | Ile | Leu | Ser | Gln | Gly | Ser | Cys | Pro |
| 65 | | | | | 70 | | | | | 75 | | | | | 80 |
| Thr | Pro | Asn | Ser | Ile | Tyr | Val | Trp | Ala | Asp | Val | Asp | Gln | Arg | Thr | Leu |
| | | | | 85 | | | | | 90 | | | | | 95 | |
| Lys | Thr | Gly | Glu | Ala | Phe | Leu | Ala | Gly | Leu | Ala | Pro | Gln | Cys | Gly | Leu |
| | | | 100 | | | | | 105 | | | | | 110 | | |
| Thr | Ile | His | His | Gln | Gln | Asn | Leu | Glu | Lys | Ala | Asp | Pro | Leu | Phe | His |
| | | 115 | | | | | 120 | | | | | 125 | | | |
| Pro | Val | Lys | Ala | Gly | Thr | Cys | Ser | Met | Asp | Lys | Thr | Gln | Val | Gln | Gln |
| | 130 | | | | | 135 | | | | | 140 | | | | |
| Ala | Val | Glu | Lys | Glu | Ala | Gln | Thr | Pro | Ile | Asp | Asn | Leu | Asn | Gln | His |
| 145 | | | | | 150 | | | | | 155 | | | | | 160 |
| Tyr | Ile | Pro | Phe | Leu | Ala | Leu | Met | Asn | Thr | Thr | Leu | Asn | Phe | Ser | Thr |
| | | | | 165 | | | | | 170 | | | | | 175 | |
| Ser | Ala | Trp | Cys | Gln | Lys | His | Ser | Ala | Asp | Lys | Ser | Cys | Asp | Leu | Gly |
| | | | 180 | | | | | 185 | | | | | 190 | | |
| Leu | Ser | Met | Pro | Ser | Lys | Leu | Ser | Ile | Lys | Asp | Asn | Gly | Asn | Lys | Val |
| | | 195 | | | | | 200 | | | | | 205 | | | |
| Ala | Leu | Asp | Gly | Ala | Ile | Gly | Leu | Ser | Ser | Thr | Leu | Ala | Glu | Ile | Phe |
| | 210 | | | | | 215 | | | | | 220 | | | | |
| Leu | Leu | Glu | Tyr | Ala | Gln | Gly | Met | Pro | Gln | Ala | Ala | Trp | Gly | Asn | Ile |
| 225 | | | | | 230 | | | | | 235 | | | | | 240 |
| His | Ser | Glu | Gln | Glu | Trp | Ala | Ser | Leu | Leu | Lys | Leu | His | Asn | Val | Gln |
| | | | | 245 | | | | | 250 | | | | | 255 | |
| Phe | Asp | Leu | Met | Ala | Arg | Thr | Pro | Tyr | Ile | Ala | Arg | His | Asn | Gly | Thr |
| | | | 260 | | | | | 265 | | | | | 270 | | |
| Pro | Leu | Leu | Gln | Ala | Ile | Ser | Asn | Ala | Leu | Asn | Pro | Asn | Ala | Thr | Glu |
| | | 275 | | | | | 280 | | | | | 285 | | | |
| Ser | Lys | Leu | Pro | Asp | Ile | Ser | Pro | Asp | Asn | Lys | Ile | Leu | Phe | Ile | Ala |
| | 290 | | | | | 295 | | | | | 300 | | | | |
| Gly | His | Asp | Thr | Asn | Ile | Ala | Asn | Ile | Ala | Gly | Met | Leu | Asn | Met | Arg |
| 305 | | | | | 310 | | | | | 315 | | | | | 320 |
| Trp | Thr | Leu | Pro | Gly | Gln | Pro | Asp | Asn | Thr | Pro | Pro | Gly | Gly | Ala | Leu |
| | | | | 325 | | | | | 330 | | | | | 335 | |
| Val | Phe | Glu | Arg | Leu | Ala | Asp | Lys | Ser | Gly | Lys | Gln | Tyr | Val | Ser | Val |
| | | | 340 | | | | | 345 | | | | | 350 | | |
| Ser | Met | Val | Tyr | Gln | Thr | Leu | Glu | Gln | Leu | Arg | Ser | Gln | Thr | Pro | Leu |
| | | 355 | | | | | 360 | | | | | 365 | | | |
| Ser | Leu | Asn | Gln | Pro | Ala | Gly | Ser | Val | Gln | Leu | Lys | Ile | Pro | Gly | Cys |
| | 370 | | | | | 375 | | | | | 380 | | | | |

```
Asn Asp Gln Thr Ala Glu Gly Tyr Cys Pro Leu Ser Thr Phe Thr Arg
385                 390                 395                 400

Val Val Ser Gln Ser Val Glu Pro Gly Cys Gln Leu Gln
                405                 410

<210> SEQ ID NO 20
<211> LENGTH: 483
<212> TYPE: PRT
<213> ORGANISM: B. licheniformis
<220> FEATURE:
<221> NAME/KEY: misc_feature
<223> OTHER INFORMATION: SPEZYME FRED alpha-amylase amino acid sequence

<400> SEQUENCE: 20

Ala Asn Leu Asn Gly Thr Leu Met Gln Tyr Phe Glu Trp Tyr Thr Pro
1               5                   10                  15

Asn Asp Gly Gln His Trp Lys Arg Leu Gln Asn Asp Ser Ala Tyr Leu
            20                  25                  30

Ala Glu His Gly Ile Thr Ala Val Trp Ile Pro Pro Ala Tyr Lys Gly
        35                  40                  45

Thr Ser Gln Ala Asp Val Gly Tyr Gly Ala Tyr Asp Leu Tyr Asp Leu
    50                  55                  60

Gly Glu Phe His Gln Lys Gly Thr Val Arg Thr Lys Tyr Gly Thr Lys
65                  70                  75                  80

Gly Glu Leu Gln Ser Ala Ile Lys Ser Leu His Ser Arg Asp Ile Asn
                85                  90                  95

Val Tyr Gly Asp Val Val Ile Asn His Lys Gly Ala Asp Ala Thr
            100                 105                 110

Glu Asp Val Thr Ala Val Glu Val Asp Pro Ala Asp Arg Asn Arg Val
        115                 120                 125

Ile Ser Gly Glu Tyr Leu Ile Lys Ala Trp Thr His Phe His Phe Pro
    130                 135                 140

Gly Arg Gly Ser Thr Tyr Ser Asp Phe Lys Trp His Trp Tyr His Phe
145                 150                 155                 160

Asp Gly Thr Asp Trp Asp Glu Ser Arg Lys Leu Asn Arg Ile Tyr Lys
                165                 170                 175

Phe Gln Gly Lys Ala Trp Asp Trp Glu Val Ser Ser Glu Asn Gly Asn
            180                 185                 190

Tyr Asp Tyr Leu Met Tyr Ala Asp Ile Asp Tyr Asp His Pro Asp Val
        195                 200                 205

Val Ala Glu Ile Lys Arg Trp Gly Thr Trp Tyr Ala Asn Glu Leu Gln
    210                 215                 220

Leu Asp Gly Phe Arg Leu Asp Ala Val Lys His Ile Lys Phe Ser Phe
225                 230                 235                 240

Leu Arg Asp Trp Val Asn His Val Arg Glu Lys Thr Gly Lys Glu Met
                245                 250                 255

Phe Thr Val Ala Glu Tyr Trp Gln Asn Asp Leu Gly Ala Leu Glu Asn
            260                 265                 270

Tyr Leu Asn Lys Thr Asn Phe Asn His Ser Val Phe Asp Val Pro Leu
        275                 280                 285

His Tyr Gln Phe His Ala Ala Ser Thr Gln Gly Gly Gly Tyr Asp Met
    290                 295                 300

Arg Lys Leu Leu Asn Gly Thr Val Val Ser Lys His Pro Leu Lys Ser
305                 310                 315                 320

Val Thr Phe Val Asp Asn His Asp Thr Gln Pro Gly Gln Ser Leu Glu
                325                 330                 335
```

```
Ser Thr Val Gln Thr Trp Phe Lys Pro Leu Ala Tyr Ala Phe Ile Leu
            340             345             350
Thr Arg Glu Ser Gly Tyr Pro Gln Val Phe Tyr Gly Asp Met Tyr Gly
        355             360             365
Thr Lys Gly Asp Ser Gln Arg Glu Ile Pro Ala Leu Lys His Lys Ile
    370             375             380
Glu Pro Ile Leu Lys Ala Arg Lys Gln Tyr Ala Tyr Gly Ala Gln His
385             390             395             400
Asp Tyr Phe Asp His His Asp Ile Val Gly Trp Thr Arg Glu Gly Asp
            405             410             415
Ser Ser Val Ala Asn Ser Gly Leu Ala Ala Leu Ile Thr Asp Gly Pro
            420             425             430
Gly Gly Ala Lys Arg Met Tyr Val Gly Arg Gln Asn Ala Gly Glu Thr
            435             440             445
Trp His Asp Ile Thr Gly Asn Arg Ser Glu Pro Val Val Ile Asn Ser
        450             455             460
Glu Gly Trp Gly Glu Phe His Val Asn Gly Gly Ser Val Ser Ile Tyr
465             470             475             480
Val Gln Arg
```